(12) United States Patent
Kim et al.

(10) Patent No.: US 7,790,730 B2
(45) Date of Patent: Sep. 7, 2010

(54) IMIDAZO[4,5-D]PYRIMIDINES, THEIR USES AND METHODS OF PREPARATION

(75) Inventors: Choung U. Kim, San Carlos, CA (US); Johan Neyts, Kessel-Lo (BE); David A. Oare, Belmont, CA (US); Gerhard Puerstinger, Badhausstrasse 10/4, A-6080 Igls (AT)

(73) Assignees: Gilead Sciences, Inc., Foster City, CA (US); K.U. Leuven Research & Development, Leuven (BE); Gerhard Puerstinger, Igls (AT)

( * ) Notice: Subject to any disclaimer, the term of this patent is extended or adjusted under 35 U.S.C. 154(b) by 762 days.

(21) Appl. No.: 11/190,751

(22) Filed: Jul. 26, 2005

(65) Prior Publication Data

US 2006/0052602 A1    Mar. 9, 2006

Related U.S. Application Data

(60) Provisional application No. 60/591,726, filed on Jul. 27, 2004.

(51) Int. Cl.
| | |
|---|---|
| C07D 473/02 | (2006.01) |
| A61P 31/14 | (2006.01) |
| A61K 31/52 | (2006.01) |
| C07D 471/04 | (2006.01) |
| A61K 31/4745 | (2006.01) |
| C07D 261/08 | (2006.01) |

(52) U.S. Cl. ............... 514/263.1; 514/263.2; 514/263.3; 514/252.02; 544/264; 544/265; 544/276; 544/277; 544/238

(58) Field of Classification Search ............... 514/263.1, 514/263.2, 263.3, 252.02; 544/264, 265, 544/276, 277, 238
See application file for complete search history.

(56) References Cited

U.S. PATENT DOCUMENTS

| | | | |
|---|---|---|---|
| 4,914,108 A | 4/1990 | Khanna et al. | |
| 4,988,707 A | 1/1991 | Stealey et al. | |
| 4,990,518 A | 2/1991 | Khanna et al. | |
| 5,227,384 A | 7/1993 | Khanna et al. | |
| 5,302,601 A | 4/1994 | Khannal et al. | |
| 5,486,525 A | 1/1996 | Summers et al. | |
| 6,268,373 B1 * | 7/2001 | Cavalla et al. | 514/263.3 |
| 6,319,928 B1 * | 11/2001 | Chasin et al. | 514/263.22 |
| 2004/0038994 A1 * | 2/2004 | Wilson | 514/260.1 |
| 2005/0222198 A1 * | 10/2005 | Bondy et al. | 514/303 |
| 2006/0052602 A1 * | 3/2006 | Kim et al. | 544/264 |
| 2007/0244148 A1 * | 10/2007 | Bondy et al. | 514/303 |

FOREIGN PATENT DOCUMENTS

| | | |
|---|---|---|
| EP | 320992 A * | 6/1989 |
| EP | 1 132 381 | 9/2001 |
| EP | 1 162 196 | 12/2001 |
| EP | 1 386 923 | 2/2004 |
| GB | 2 158 440 | 11/1985 |
| WO | WO 95/02597 | 1/1995 |
| WO | WO 96/12703 | 5/1996 |
| WO | WO 96/15111 A1 | 5/1996 |
| WO | WO 00/20400 | 4/2000 |
| WO | WO 00/20425 | 4/2000 |
| WO | WO 00/73307 | 12/2000 |
| WO | WO 01/95910 | 12/2001 |
| WO | WO-02/04425 | 1/2002 |
| WO | WO 02/067942 | 9/2002 |
| WO | WO 03/007945 | 1/2003 |
| WO | WO 03/010140 | 2/2003 |
| WO | WO 03/014229 | 2/2003 |
| WO | WO 2004/005286 | 1/2004 |
| WO | WO 2004/018468 | 3/2004 |
| WO | WO 2004/033455 | 4/2004 |
| WO | WO 2005/063744 | 7/2005 |
| WO | WO 2005061505 A1 * | 7/2005 |

OTHER PUBLICATIONS

Beasley et al., Australian Journal of Chemistry (1981), 34(5), 1107-16.*
Doree et al, Proceedings of the National Academy of Sciences of the United States of America (1976), 73(5), 1669-73.*

(Continued)

*Primary Examiner*—Mark L Berch

(57) ABSTRACT

The present invention relates to pharmaceutical compositions for the treatment or prevention of viral infections comprising as an active principle at least one compound having the general formula (A):

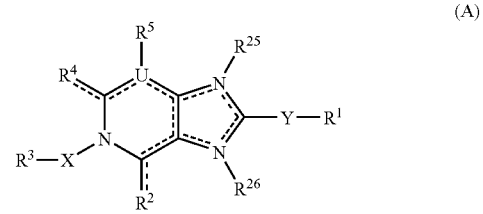

(A)

wherein U is N or C; X is selected from $C_1$-$C_{10}$ alkylene, $C_{2-10}$ alkenylene or $C_{2-10}$ alkynylene, where each may include one or more intrachain heteroatoms selected from O, S, or $NR^{11}$, provided any such heteroatom is not adjacent to the N in the ring; $R^3$ is selected from aryl, aryloxy, arylthio, cycloalkyl, cycloalkenyl, cycloalkynyl, aryl-N($R^{10}$)—, or heterocycle, where each said substituent is optionally substituted with at least one $R^{17}$, provided that for cycloalkenyl the double bond is not adjacent to a nitrogen; and the other substituents are described in the specification.

The invention also relates to processes for the preparation of compounds according to the invention having above mentioned general formula, their pharmaceutically acceptable formulations and their use as a medicine or to treat or prevent viral infections.

63 Claims, No Drawings

OTHER PUBLICATIONS

Montgomery et al., Journal of Organic Chemistry (1962), 27, 195-9.*
Saito, et al Chemical & Pharmaceutical Bulletin (1992), 40(12), 3201-5.*
Niwa et al., Tetrahedron Letters (1991), 32(7), 927-30.*
Nielsen, F. E. et al, Tetrahedron (1982), 38(10), 1435-41.*
Leonard, Nelson J.; Journal of Heterocyclic Chemistry (1966), 3(4), 485-9.*
Itaya, Tetrahedron Letters vol. 39, Issue 26, Jun. 25, 1998, pp. 4695-4696.*
Andresen, Tetrahedron vol. 52, Issue 40, Sep. 1996, pp. 12979-12992.*
Fujii, Tetrahedron Letters vol. 32, Issue 1, Jan. 1, 1991, pp. 97-100.*
Baba et al. "Synergistic Antiviral Effects of Antiherpes Compounds and Human Leukocyte Interferon on Varicella-Zoster Virus in Vitro." 515-517;Antimicro AG & Chemo., 1984.
Chou et al. "Quantitative Analysis of Dose-Effect Relationships: The Combined Effects of Multiple Drugs or Enzyme Inhibitors." 22:27-55;Adv Enzyme Regulation,1984.
Elion et al."Antagonist of Nucleic Acid Derivatives." 208(2):477-488;J Biol Chem.,1954.
Fletcher et al. "Heterocyclic Systems." p. 49-64;Nomenclature of Organic Adv. Ser.,1974.
Jacob III, Peyt" Resolution of ( )-5-Bromonornicotine. Synthesis of (R)- and (S)- Nornicotine of High Enantiomeric Purity." 47:4165-4167; J Org Chem., 1982.
Lochmuller et al. " Chromatographic Resolution of Enantiomers Selective Review." 113:283-302; J Chromatog., 1975.
Okamoto et al. "Optical resolution of dihydropyridine enantiomers by High-performance liquid chromatography using . . . "513:375-378;Journal of Chromatography., 1990.
Rigaudy et al. "Fundamental Heterocyclic Systems"p. 53-76;Nomenclature of Organic Adv. Ser., 1979.
Yutilov et al. "Synthesis and Antiviral Activity of Spinaceamine Derivatives" *Pharmaceutical Chemistry Journal*, 23(1):56-59 (Jan. 1989 ).

* cited by examiner

IMIDAZO[4,5-D]PYRIMIDINES, THEIR USES AND METHODS OF PREPARATION

This application claims the benefit of U.S. Provisional Application Nos. 60/591,726 filed Jul. 27, 2004.

FIELD OF THE INVENTION

The present invention relates to imidazo[4,5-d]pyrimidines, their uses and manufacture. The invention relates specifically to antiviral compounds, in particular such compounds for the treatment of Flaviviridae and Picornaviridae.

BACKGROUND OF THE INVENTION

The family of the Flaviviridae consists of 3 genera, the pestiviruses, the flaviviruses and the hepaciviruses and also contains the hepatitis G virus (HGV/GBV-C) that has not yet been assigned to a genus. Pestiviruses such as the Classical Swine Fever Virus (CSFV), the Bovine Viral Diarrhea Virus (BVDV) and the Border Disease Virus (BDV) cause infections of domestic livestock (respectively pigs, cattle and sheep) and are responsible for significant economic losses world-wide. BVDV, the prototypic representative of the pestivirus genus is ubiquitous and causes a range of clinical manifestations, including abortion, teratogenesis, respiratory problems, chronic wasting disease, immune system dysfunction, and predisposition to secondary viral and bacterial infections and may also cause acute fatal disease. Fetuses of cattle can be infected persistently with BVDV, these animals remain viremic throughout life and serve as a continuous sources for virus spread in herds.

Vaccines are used in some countries with varying degrees of success to control pestivirus disease. In other countries, animal culling and slaughter are used to contain pestivirus disease outbreaks.

The World Health Organization estimates that world-wide 170 million people (3% of the world's population) are chronically infected with HCV (Hepatitis C Virus). These chronic carriers are at risk of developing cirrhosis and/or liver cancer. In studies with a 10 to 20 year follow-up, cirrhosis developed in 20-30% of the patients, 1 to 5% of whom may develop liver cancer during the next ten years. The only treatment option available today is the use of interferon ($\alpha$-2 (or its pegylated form) either alone or combined with ribavirin. However, sustained response is only observed in about 40% of the patients and treatment is associated with serious adverse effects. There is thus an urgent need for potent and selective inhibitors of the replication of HCV in order to treat infections with HCV. Furthermore, the study of specific inhibitors of HCV replication has been hampered by the fact that it is not possible to propagate HCV (efficiently) in cell culture. Since HCV and pestiviruses belong to the same virus family and share many similarities (organization of the genome, analogous gene products and replication cycle), pestiviruses have been adopted as a model and surrogate for HCV. For example BVDV is closely related to hepatitis C virus (HCV) and used as a surrogate virus in drug development for HCV infection.

The compound 3-[((2-dipropylamino)ethyl)thio]-5H-1,2,4-triazino[5,6-b]indole has been reported to selectively inhibit the replication of BVDV and other pestiviruses (Baginski S G et. al., Proc. Natl. Acad. Sci. U.S.A. 2000 Jul. 5; 97(14):7981-6). Currently, there is no antiviral treatment for pestiviral infections.

Coxsackie viruses belong to the group of the enteroviruses, family of the Picornaviridae. They cause a heterogeneous group of infections including herpangina, aseptic meningitis, a common-cold-like syndrome, a non-paralytic poliomyelitis-like syndrome, epidemic pleurodynia (an acute, febrile, infectious disease generally occurring in epidemics), hand-foot-mouth syndrome, pediatric and adult pancreatitis and serious myocarditis.

Currently only pleconaril (3-13,5-dimethyl-4-[[3-methyl-5-isoxazolyl)propyl]phenyl]-5-(trifluoromethyl-1,2,4-oxadiazole)) and enviroxime (2-amino-1-(isopropylsulfonyl)-6-benzimidazole phenyl ketone oxime) have been studied clinically for the treatment of infections with enteroviruses. Pleconaril is a so called "capsid function-inhibitor"; enviroxime prevents the formation of the RNA replicative intermediate. Enviroxime resulted in only modest clinical and virological benefit in some studies and no benefits in others. Clinical response with Pleconaril has been observed in some studies, but the compound has not been marketed.

Reference is made to U.S. Pat. Nos. 4,914,108, 4,990,518, 4,988,707, 5,227,384, 5,302,601 and 5,486,525, EP 113238, WO 96/1192, WO 96/12703, Chemical Abstracts acc no. 1987: 18435 and Chemical Abstracts acc no. 1983: 594812, EP 1162196, WO 95/02597, WO 04/033455; WO 2004/018468; WO 03/014229; WO 02/067942; WO 00/073307 and U.S. 2004/0122228.

A need exists for compounds having activity against the Picornavidae and Flaviviridae, in particular HCV, having improved physicochemical and/or pharmacological properties.

SUMMARY OF THE INVENTION

The compounds of this invention have the general formula (A),

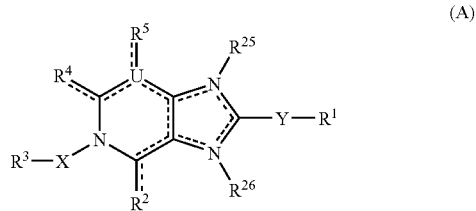

(A)

wherein:
the dotted lines represent optional double bonds, provided that no two double bonds are adjacent to one another, and that the dotted lines represent at least 3, optionally 4 double bonds;

U is N;

$R^1$ is selected from aryl, heterocycle, $C_1$-$C_{10}$ alkoxy, $C_1$-$C_{10}$ thioalkyl, $C_1$-$C_{10}$ alkyl-amino, $C_1$-$C_{10}$ dialkyl-amino, $C_{3-10}$ cycloalkyl, $C_{4-10}$ cycloalkenyl, and $C_{4-10}$ cycloalkynyl, wherein each are optionally substituted with 1 or more $R^6$;

Y is selected from a single bond, O, $S(O)_m$ (where m is an integer from 0 to 2), $NR^{11}$, $C_{1-10}$ alkylene, $C_{2-10}$ alkenylene, and $C_{2-10}$ alkynylene, or $C_{1-10}$ alkylene, $C_{2-20}$ alkenylene or $C_{2-10}$ alkynylene, wherein 1 to 3 methylene groups optionally are independently replaced by 1 to 3 heteroatoms selected from O, S or $NR^{11}$;

$R^2$ and $R^4$ are independently selected from hydrogen, $C_{1-18}$ alkyl, $C_{2-18}$ alkenyl, $C_{2-18}$ alkynyl, $C_{1-18}$ alkoxy, $C_{1-18}$ alkylthio, halogen, —OH, —CN, —NO$_2$, —NR$^7$R$^8$, haloalkyloxy, haloalkyl, —C(=O)R$^9$, —C(=S)R$^9$, SH, aryl, aryloxy, arylthio, arylalkyl, $C_{1-18}$ hydroxyalkyl, $C_{3-10}$ cycloalkyl, $C_{3-10}$ cycloalkyloxy, $C_{3-10}$ cycloalkylthio, $C_{3-10}$ cycloalkenyl, $C_{7-10}$ cycloalkynyl, and heterocycle, provided that when one of $R^{25}$ or $R^{26}$ is present, then either $R^2$ or $R^4$ is selected from =O, =S, or =NR$^{27}$;

X is selected from $C_1$-$C_{10}$ alkylene, $C_{2-10}$ alkenylene or $C_{2-10}$ alkynylene, where each may include one or more heteroatoms selected from O, S, or NR$^{11}$, provided any such heteroatom is not adjacent to the N in the ring;

$R^3$ is selected from aryl, aryloxy, arylthio, cycloalkyl, cycloalkenyl, cycloalkynyl, aryl-N(R$^{10}$)—, or heterocycle, where each said substituent is optionally substituted with at least one $R^{17}$, provided that for cycloalkenyl the double bond is not adjacent to a nitrogen;

$R^5$ independently is absent or is selected from hydrogen, $C_{1-18}$ alkyl, $C_{2-18}$ alkenyl, $C_{2-18}$ alkynyl, $C_{1-18}$ alkoxy, $C_{1-18}$ alkylthio, halogen, —OH, —CN, —NO$_2$, —NR$^7$R$^8$, haloalkyloxy, haloalkyl, —C(=O)R$^9$, —C(=O)OR$^9$, —C(=S)R$^9$, SH, aryl, aryloxy, arylthio, arylalkyl, $C_{1-18}$ hydroxyalkyl, $C_{3-10}$ cycloalkyl, $C_{3-10}$ cycloalkyloxy, $C_{3-10}$ cycloalkylthio, $C_{3-10}$ cycloalkenyl, $C_{7-10}$ cycloalkynyl, and heterocycle;

$R^6$ is selected from hydrogen, $C_{1-18}$ alkyl, $C_{2-18}$ alkenyl, $C_{2-18}$ alkynyl, $C_{1-18}$ alkoxy, $C_{1-18}$ alkylthio, $C_{1-18}$ alkylsulfoxide, $C_{1-18}$ alkylsulfone, $C_{1-18}$ halo-alkyl, $C_{2-18}$ halo-alkenyl, $C_{2-18}$ halo-alkynyl, $C_{1-18}$ halo-alkoxy, $C_{1-18}$ halo-alkylthio, $C_{3-10}$ cycloalkyl, $C_{3-10}$ cycloalkenyl, $C_{7-10}$ cycloalkynyl, halogen, OH, CN, cyanoalkyl, —C(O)OR$^{18}$, NO$_2$, —NR$^7$R$^8$, $C_{1-18}$ haloalkyl, C(=O) R$^{18}$, C(=S)R$^{18}$, SH, aryl, aryloxy, arylthio, arylsulfoxide, arylsulfone, arylsulfonamide, aryl($C_{1-18}$)alkyl, aryl ($C_{1-18}$)alkyloxy, aryl($C_{1-18}$)alkylthio, heterocycle, and $C_{1-18}$ hydroxyalkyl, where each may be optionally substituted with at least 1 $R^{19}$;

$R^7$ and $R^8$ are independently selected from hydrogen, $C_{1-18}$ alkyl, $C_{1-18}$ alkenyl, aryl, $C_{3-10}$ cycloalkyl, $C_{4-10}$ cycloalkenyl, heterocycle, —C(=O)R$^{12}$; —C(=S)R$^{12}$, an amino acid residue linked through a carboxyl group thereof, and the group formed when $R^7$ and $R^8$ are taken together with the nitrogen to form a heterocycle;

$R^9$ and $R^{18}$ are independently selected from hydrogen, OH, $C_{1-18}$ alkyl, $C_{2-18}$ alkenyl, $C_{3-10}$ cycloalkyl, $C_{4-10}$ cycloalkenyl, $C_{1-18}$ alkoxy, —NR$^{15}$R$^{16}$, aryl, an amino acid residue linked through an amino group of the amino acid, CH$_2$OCH(=O)R$^{9a}$, and CH$_2$OC(=O)OR$^{9a}$ where R$^{9a}$ is $C_1$-$C_{12}$ alkyl, $C_6$-$C_{20}$ aryl, $C_6$-$C_{20}$ alkylaryl or $C_6$-$C_{20}$ aralkyl;

$R^{10}$ and $R^{11}$ are independently selected from the group consisting of hydrogen, $C_{1-18}$ alkyl, $C_{2-18}$ alkenyl, $C_{3-10}$ cycloalkyl, $C_{4-10}$ cycloalkenyl, aryl, —C(=O)R$^{12}$, heterocycle, and an amino acid residue;

$R^{12}$ is selected from the group consisting of hydrogen, $C_{1-18}$ alkyl, $C_{2-18}$ alkenyl, aryl, $C_{3-10}$ cycloalkyl, $C_{4-10}$ cycloalkenyl, and an amino acid residue;

$R^{15}$ and $R^{16}$ are independently selected from hydrogen, $C_{1-18}$alkyl, $C_{2-18}$ alkenyl, $C_{2-18}$ alkynyl, aryl, arylalkyl (unsubstituted or substituted with C(O)OR$^{18}$), $C_{3-10}$ cycloalkyl, $C_{4-10}$ cycloalkenyl, and an amino acid residue;

$R^{17}$ is independently selected from the group consisting of (a) hydrogen, $C_{1-18}$ alkyl, $C_{2-18}$ alkenyl, $C_{2-18}$ alkynyl, $C_{1-18}$ alkoxy, $C_{1-18}$ alkylthio, $C_{1-18}$ alkylsulfoxide, $C_{1-18}$ alkylsulfone, $C_{1-18}$ halogenated alkyl, $C_{2-18}$ halogenated alkenyl, $C_{2-18}$ halogenated alkynyl, $C_{1-18}$ halogenated alkoxy, $C_{1-18}$ halogenated alkylthio, $C_{3-10}$ cycloalkyl, $C_{3-10}$ cycloalkenyl, $C_{7-10}$ cycloalkynyl, halogen, OH, CN, CO$_2$H, CO$_2$R$^{18}$, NO$_2$, NR$^7$R$^8$, haloalkyl, C(=O) R$^{18}$, C(=S)R$^{18}$, SH, aryl, aryloxy, arylthio, arylsulfoxide, arylsulfone, arylsulfonamide, arylalkyl, arylalkyloxy, arylalkylthio, heterocycle, and $C_{1-18}$ hydroxyalkyl, where each of said aryl, aryloxy, arylthio, arylsulfoxide, arylsulfone, arylsulfonamide, arylalkyl, arylalkyloxy, arylalkylthio, heterocycle, or $C_{1-18}$ hydroxyalkyl is optionally substituted with 1 or more R$^{19}$, and (b) M-Q- wherein M is a ring optionally substituted with 1 or more R$^{19}$, and Q is a bond or a linking group connecting M to $R^3$ having 1 to 10 atoms selected from C and optionally 1 or more O, N or S atoms and optionally substituted with 1 or more R$^{19}$;

$R^{19}$ is selected from
(a) H;
(b) NO$_2$, SH, NR$^{20}$R$^{21}$, OH, halogen and CN;
(c) Sulfone, sulfonamide and sulfoxide;
(d) $C_{1-18}$ alkyl, $C_{2-18}$ alkenyl and $C_{2-18}$ alkynyl;
(e) $C_{1-18}$ alkyl, $C_{2-18}$ alkenyl and $C_{2-18}$ alkynyl wherein 1 or more methylene are replaced by 1 or more O, S, NR$^{20}$, C(O)NR$^{20}$R$^{21}$, OC(O)R$^{12}$, C(O)OR$^{12}$ or N(R$^{20}$)C(O);
(f) Substituents c), d) or e) substituted further by $C_{3-10}$ cycloalkyl, $C_{4-10}$ cycloalkenyl, $C_{4-10}$ cycloalkynyl, aryl or heterocycle;
(g) $C_{3-10}$ cycloalkyl, $C_{4-10}$ cycloalkenyl, $C_{4-10}$ cycloalkynyl, aryl and heterocycle, or said groups substituted with $C_{1-6}$ alkyl, C(O)OR$^{12}$=O, halogen, CN, C(O)NR$^{20}$R$^{21}$, C(O)R$^{18}$ or OC(O)R$^{18}$;
(h) C(O)R$^{18}$, C(O)OR$^{18}$, OC(O)R$^{18}$, C(S)R$^{18}$ and C(O)N (R$^{12}$)$_2$;
(i) Substituents d) or e) substituted with =O, CN, halogen, C(O)R$^{18}$, C(O)NR$^{20}$R$^{21}$, OC(O)R$^{18}$, heterocycle, and heterocycle substituted with $C_1$-$C_6$ alkyl, C(O)OR$^{12}$, =O, CN, halogen, OC(O)R$^{18}$ or C(O)NR$^{20}$R$^{21}$;
(j) Substituents c) substituted further with $C_{1-18}$ alkyl; and
(k) Substituents f) or g) substituted further with $C_{1-18}$ alkyl, =O, NR$^{20}$R$^{21}$, CN, $C_{1-18}$ alkoxy, heterocycle, $C_{1-18}$ haloalkyl, heterocyclealkyl or halogen;

$R^{20}$ and $R^{21}$ are independently selected from hydrogen, $C_{1-18}$ alkyl, $C_{2-18}$ alkenyl, $C_{2-18}$ alkynyl, aryl, heterocycle, $C_{3-10}$ cycloalkyl, $C_{4-10}$ cycloalkenyl, —C(=O) R$^{12}$, and —C(=S)R$^{12}$;

$R^{25}$ and $R^{26}$ are independently not present or are selected from hydrogen, $C_{1-18}$ alkyl, $C_{3-10}$cycloalkyl, aryl, heterocycle, where each is optionally independently substituted with 1 to 4 of $C_{1-6}$ alkyl, $C_{1-6}$ alkoxy, halo, CH$_2$OH, benzyloxy, and OH;

$R^{27}$ is selected from hydrogen, $C_{1-18}$ alkyl, $C_{3-10}$ cycloalkyl, ($C_{3-10}$ cycloalkyl)-$C_{1-6}$ alkyl, aryl, and arylC$_{1-18}$ alkyl; and salts, tautomers, polymorphs, isomers and solvates thereof.

In a further embodiment of the invention the compounds of the formulas of this invention are optionally combined with pharmacologically acceptable excipients.

In a further embodiment of the invention the compounds of the formulas of this invention are administered in therapeutically effective amounts to subjects (humans or animals) in need of antiviral therapy, in particular for inhibiting the infection, growth or replication of Flaviviridae and Picornaviridae, especially BVDV, HCV and Coxsackie virus.

The invention further relates to a method of screening antiviral compounds which comprises providing a compound of formula (A) and determining the anti-viral activity of said compound.

Also within the scope of the invention is a metabolite of the compounds of the formulas of this invention made by the process of administering a compound of formula (A) to a subject and recovering the metabolite from the subject.

The invention also comprises a method for structure-activity determination of analogues of compounds of WO 04/005286 having the general structure

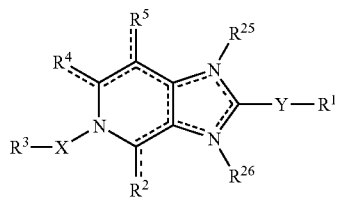

wherein
the R, X and Y groups are defined in WO 04/005286, comprising
(A) preparing an analogue of a compound falling within the scope of WO 2004/005286 wherein $C_7$ is replaced by N; and
(B) determining the anti-HCV activity of the compound of step (A).

DETAILED DESCRIPTION OF THE INVENTION

Definitions

"Alkyl" means saturated hydrocarbon moiety where the moiety may be acyclic, cyclic or a combination of acyclic and cyclic portions. The acyclic portion may contain 1 to 3 carbon atoms, and each ring may contain 3 to 6 carbon atoms (for example, 3-methylcyclohexyl). Within this definition, the term "cycloalkyl" refers to the saturated hydrocarbon moieties that are cyclic. Examples of "alkyl" include methyl, ethyl, 1-propyl, 2-propyl, 1-butyl, 2-methyl-1-propyl(i-Bu), 2-butyl (s-Bu) 2-methyl-2-propyl (t-Bu), 1-pentyl (n-pentyl), 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, cyclopropyl, cyclobutyl, cyclopentyl and cyclohexyl, cyclopropyl, cyclobutyl, cyclopentyl, cycloheptyl, cyclooctyl and the like, or a $C_{7-10}$ polycyclic saturated hydrocarbon radical having from 7 to 10 carbon atoms such as, for, instance, norbornyl, fenchyl, trimethyltricycloheptyl or adamantyl.

"Alkenyl" means a hydrocarbon moiety with at least one site of double bond unsaturation where the moiety may be acyclic, cyclic or a combination of acyclic and cyclic portions. The acyclic portion may contain 1 to 3 carbon atoms, and each cyclic portion may contain 3 to 6 carbon atoms. A site of double bond unsaturation may be in a acyclic portion, a cyclic portion. In the instance of a moiety having a combination of acyclic and cyclic portions, there may be a site of double bond unsaturation in each of the portions. Within this definition, the term "cycloalkenyl" refers to the double bond unsaturated hydrocarbon moieties that are cyclic. Examples the term "alkenyl" include, but are not limited to, ethylene or vinyl (—CH=CH$_2$), allyl (—CH$_2$CH=CH$_2$), cyclopentenyl (—C$_5$H$_7$), 5-hexenyl (—CH$_2$CH$_2$CH$_2$CH$_2$CH=CH$_2$), 1-cyclopent-1-enyl, 1-cyclopent-2-enyl, 1-cyclopent-3-enyl, 1-cyclohex-1-enyl, 1-cyclohex-2-enyl, and 1-cyclohex-3-enyl. The double bond optionally is in the cis or trans configuration.

"Alkynyl" means a hydrocarbon moiety with a least one site of triple bond unsaturation where the moiety may be acyclic, cyclic or a combination of acyclic and cyclic portions. The acyclic portion may contain 1 to 3 carbon atoms, and each cyclic portion may contain 7 or more carbon atoms. Within this definition, the term "cycloalkynl" refers to triple bond unsaturated hydrocarbon moieties that are cyclic. Examples of the term "alkynyl" include, but are not limited to, —CCH, —CH$_2$CCH, —CH$_2$CC-cyclohexyl, or —CH$_2$-cycloheptynyl.

The suffix "-ene" used in connection with alkyl, alkenyl and alkynyl groups refers to such groups with at least 2 sites of substitution. Such polyvalent hydrocarbon radicals include, but are not limited to, methylene (—CH$_2$—) 1,2-ethylene (—CH$_2$CH$_2$—), 1,3-propylene (—CH$_2$CH$_2$CH$_2$—), 1,4-butylene (—CH$_2$CH$_2$CH$_2$CH$_2$—), 1,2-ethylene (—CH=CH—), —CC—, propargyl (—CH$_2$CC—), and 4-pentynyl (—CH$_2$CH$_2$CH$_2$CCH—). Optionally, alkylene, alkenylene and alkynylene are substituted with O, S or N, generally meaning that O, S or N replace a carbon atom and the valence appropriate number of carbon substituents (generally 1 or 2H). N in this case is generally $R^{11}$.

"Aryl" means an aromatic hydrocarbon containing 1 or more rings, generally 1, 2 or 3, with 4 to 6 carbon atoms in each, ordinarily 5 or 6 carbon atoms.

"Arylalkyl," "arylalkenyl" and "arylalkynyl" means an alkyl, alkenyl or alkynyl radical, respectively, in which one of the hydrogen atoms, typically a terminal or sp3 carbon atom, is replaced with an aryl radical. Typical arylalkyl groups include, but are not limited to, benzyl, 2-phenylethan-1-yl, 2-phenylethen-1-yl, naphthylmethyl, 2-naphthylethan-1-yl, 2-naphthylethen-1-yl, naphthobenzyl, 2-naphthophenylethan-1-yl and the like.

As noted, carbocycles optionally are found as single rings or multiple ring systems. Ordinarily the hydrocarbons of the compounds of the formulas of this invention are single rings. Monocyclic carbocycles generally have 3 to 6 ring atoms, still more typically 5 or 6 ring atoms. Bicyclic carbocycles typically have 7 to 12 ring atoms, e.g. arranged as a bicyclo [4,5], [5,5], [5,6] or [6,6] system, or 9 or 10 ring atoms arranged as a bicyclo [5,6] or [6,6] system.

If the number of carbon atoms is unspecified for a hydrocarbon, typically the number of carbon atoms will range from 1 to 18, except that the number of carbons typically will range from 2 to 18 for unsaturated hydrocarbons and from 6 to 10 for aryl.

"Heterocycle" or "heterocycle" means any 4, 5, 6, 7, 8 or 9 membered single or fused ring system containing one or more heteroatoms selected from the group consisting of O, N or S. Heterocycles optionally are entirely aromatic, entirely saturated, or contain 1 or more intra-ring sites of unsaturation, typically double bonds. Multiple heterocyclic rings (one or more of which contains a heteroatom) are bridged or spiro. Generally, the heterocyclic rings will be aromatic, and usually they are single rings. Examples of heterocycles include oxazacyloalkyl, morpholinyl, dioxacycloalkyl, thiacycloalkenyl, pyridyl, dihydroypyridyl, tetrahydropyridyl (piperidyl), thiazolyl, tetrahydrothiophenyl, furanyl, thienyl, pyrrolyl, pyranyl, pyrazolyl, pyrazolidinyl, pyrazolinyl, imidazolyl, tetrazolyl, benzofuranyl, thianaphthalenyl, indolyl, indolenyl, quinolinyl, isoquinolinyl, benzimidazolyl, piperidinyl, piperazinyl, pyrrolidinyl, 2-pyrrolidonyl, pyrrolinyl, tetrahydrofuranyl, bis-tetrahydrofuranyl, tetrahydropyranyl, bis-tetrahydropyranyl, tetrahydroquinolinyl, tetrahydroisoquinolinyl, decahydroquinolinyl, octahydroisoquinolinyl, azocinyl, triazinyl, 6H-1,2,5-thiadiazinyl, 2H,6H-1,5,2-dithiazinyl, thianthrenyl, pyranyl, isobenzofuranyl, chromenyl, xanthenyl, phenoxathinyl, 2H-pyrrolyl, isothiazolyl, isothiazoledinyl, isoxazolyl, oxazolinyl, pyrazinyl, pyridazinyl, pyrimidinyl, pyrrolidinyl, pyrrolinyl, indolizinyl, isoindolyl, 3H-indolyl, 1H-indazoly, purinyl, 4H-quinolizinyl, isoquinolyl, quinolyl, phthalazinyl, naphthyridinyl, quinoxalinyl, quinazolinyl, cinnolinyl, pteridinyl, 4aH-carbazolyl, carbazolyl, β-carbolinyl, phenanthridinyl, acridinyl, pyrimidinyl, phenanthrolinyl, phenazinyl, phenothiazinyl, furazanyl, phenoxazinyl, isochromanyl, chromanyl, imidazolidinyl, imidazolinyl, pyrazolidinyl, pyrazolinyl, piperazinyl, indolinyl, isoindolinyl, quinuclidinyl, oxazolidinyl, benzotriazolyl, benzisoxazolyl, oxindolyl, benzoxazolinyl, benzothienyl, benzothiazolyl and isatinoyl. Other suitable heterocycles are exemplified in Rigaudy et. al., Nomenclature of Organic Chemistry, Sections A-H (1979) at pp. 53-76 and Fletcher et. al., Nomenclature of Organic Compounds, Adv. Chem. Ser. 126 (1974) at pp 49-64.

The location on the heterocycle which provides the point of attachment(s) to the rest of the compound of this invention is not critical, but those skilled in the art will recognize substitution sites that are optimal for compound stability and/or ease of synthesis. Carbon bonded heterocycles typically are bonded at position 2, 3, 4, 5, or 6 of a pyridine, position 3, 4, 5, or 6 of a pyridazine, position 2, 4, 5, or 6 of a pyrimidine, position 2, 3, 5, or 6 of a pyrazine, position 2, 3, 4, or 5 of a furan, tetrahydrofuran, thiofuran, thiophene, pyrrole or tetrahydropyrrole, position 2, 4, or 5 of an oxazole, imidazole or thiazole, position 3, 4, or 5 of an isoxazole, pyrazole, or isothiazole, position 2 or 3 of an aziridine, position 2, 3, or 4 of an azetidine, position 2, 3, 4, 5, 6, 7, or 8 of a quinoline or position 1, 3, 4, 5, 6, 7, or 8 of an isoquinoline. Still more typically, carbon bonded heterocycles include 2-pyridyl, 3-pyridyl, 4-pyridyl, 5-pyridyl, 6-pyridyl, 3-pyridazinyl, 4-pyridazinyl, 5-pyridazinyl, 6-pyridazinyl, 2-pyrimidinyl, 4-pyrimidinyl, 5-pyrimidinyl, 6-pyrimidinyl, 2-pyrazinyl, 3-pyrazinyl, 5-pyrazinyl, 6-pyrazinyl, 2-thiazolyl, 4-thiazolyl, or 5-thiazolyl.

Nitrogen containing heterocycles are bonded at nitrogen or a carbon, typically a carbon atom. These include, for example, position 1 of aziridine, 1-aziridyl, 1-azetedyl, 1-pyrrolyl, 1-imidazolyl, 1-pyrazolyl, 1-piperidinyl, 2-pyrroline, 3-pyrroline, 2-imidazoline, 3-imidazoline, 9-carbazole, 4-morpholine, 9-alpha or β-carboline, 2-isoindole, 2-pyrazoline and 3-pyrazoline, and by analogy, azetidine, pyrrole, pyrrolidine piperidine, piperazine, indole, pyrazoline, indoline, imidazole, imidazolidine, 1H-indazole and isoindoline. These and other N-containing heterocycles are well-known to those skilled in the art, and their linkage sites are a matter of discretion.

Sulfur containing heterocycles are bonded through carbon or sulfur. They include oxidized states such as —S(=O) (=O). In general, they are linked in the compounds of the formulas of this invention analogous to N-containing heterocycles.

"Alkoxy", "cycloalkoxy", "aryloxy", "arylalkyloxy", "oxy heterocycle", "thioalkyl", "thiocycloalkyl", "arylthio", and "arylalkylthio" means substituents wherein an alkyl, cycloalkyl, aryl, or arylalkyl, respectively, are attached to an oxygen atom or a sulfur atom through a single bond, such as but not limited to methoxy, ethoxy, propoxy, butoxy, thioethyl, thiomethyl, phenyloxy, benzyloxy, mercaptobenzyl and the like.

"Halogen" means any atom selected from the group consisting of fluorine, chlorine, bromine and iodine.

Any substituent designation that is found in more than one site in a compound of this invention shall be independently selected.

When a group is stated to be substituted with "one or more" of another group, this typically means 1 to 3 substituents, ordinarily 1, 2 or 3 substitutents.

Those of skill in the art will also recognize that the compounds of the invention may exist in many different protonation states, depending on, among other things, the pH of their environment. While the structural formulae provided herein depict the compounds in only one of several possible protonation states, it will be understood that these structures are illustrative only, and that the invention is not limited to any particular protonation state—any and all protonated forms of the compounds are intended to fall within the scope of the invention.

Amino Acids

"Amino-acid" refers to a radical derived from a molecule having the chemical formula $H_2N$—$CHR^{28}$—$COOH$, wherein $R^{28}$ is a side group of a naturally-occurring or known synthetic amino-acid. The amino acids optionally are substituted with hydrocarbon typically of 1 to 8 carbons at one or more carboxyl or amino groups, whether those groups are on the side chain or are free after linking the amino acid to the remainder of the compound of this invention.

Optionally the amino acid residue is a hydrophobic residue such as mono- or di-alkyl or aryl amino acids, cycloalkylamino acids and the like. Optionally, the residue does not contain a sulfhydryl or guanidino substituent.

Naturally-occurring amino acid residues are those residues found naturally in plants, animals or microbes, especially proteins thereof. Polypeptides most typically will be substantially composed of such naturally-occurring amino acid residues. These amino acids are glycine, alanine, valine, leucine, isoleucine, serine, threonine, cysteine, methionine, glutamic acid, aspartic acid, lysine, hydroxylysine, arginine, histidine, phenylalanine, tyrosine, tryptophan, proline, asparagine, glutamine and hydroxyproline. Additionally, unnatural amino acids, for example, valanine, phenylglycine and homoarginine are also included.

Generally, only one of any site in the parental molecule is substituted with an amino acid, although it is within the scope of this invention to introduce amino acids at more than one permitted site. In general, the alpha-amino or alpha-carboxyl group of the amino acid are bonded to the remainder of the molecule, i.e., carboxyl or amino groups in the amino acid side chains generally are not used to form amide bonds with the parental compound (although these groups may need to be protected during synthesis of the conjugates).

The amino acid esters optionally are hydrolyzable in vivo or in vitro under acidic (pH<3) or basic (pH>10) conditions. Optionally, they are substantially stable in the gastrointestinal tract of humans but are hydrolyzed enzymatically in blood or in intracellular environments.

$R^{28}$ usually is $C_1$-$C_6$ alkyl or $C_1$-$C_6$ alkyl substituted with amino, carboxyl, amide, carboxyl (as well as esters, as noted above), hydroxyl, $C_6$-$C_7$ aryl, guanidinyl, imidazolyl, indolyl, sulfhydryl, sulfoxide, and/or alkylphosphate. $R^{28}$ also is taken together with the amino acid alpha nitrogen to form a proline residue. However, $R^{28}$ is generally the side group of the naturally-occurring amino acid disclosed above, for example H, —$CH_3$, —$CH(CH_3)_2$, —$CH_2$—$CH(CH_3)_2$, —$CHCH_3$—$CH_2$—$CH_3$, —$CH_2$—$C_6H_5$, —$CH_2CH_2$—S—$CH_3$, —$CH_2OH$, —$CH(OH)$—$CH_3$, —$CH_2$—SH, —$CH_2$—$C_6H_4OH$, —$CH_2$—CO—$NH_2$, —$CH_2$—$CH_2$—CO—$NH_2$, —$CH_2$—COOH, —$CH_2$—$CH_2$—COOH, —$(CH_2)_4$—$NH_2$ and —$(CH2)_3$—NH—$C(NH_2)$—$NH_2$. $R^{28}$ also includes 1-guanidinoprop-3-yl, benzyl, 4-hydroxybenzyl, imidazol-4-yl, indol-3-yl, methoxyphenyl and ethoxyphenyl.

Subgeneric Embodiments $R^1$ is generally aryl or aromatic heterocyle (usually containing 1 or 2 O, S or N atoms, typically O or S) substituted with 1, 2 or 3 $R^6$ wherein $R^6$ usually is halogen, $C_{1-18}$ alkoxy; or $C_{1-18}$ haloalkyl. Typically, $R^1$ is 6 to 10 C carbocycle having 1 or 2 rings (most ordinarily phenyl) substituted with 1, 2 or 3 halogens, usually fluoro.

Y generally is a single bond, O, $C_{1-6}$ alkylene, $C_{2-6}$ alkenylene, $C_{2-6}$ alkynylene or one of said groups containing 1 to 3, usually 1, heteroatoms selected from O, S or $NR^{11}$. Examples include $-O(CH_2)_{1-5}-$, $-(CH_2)_{1-4}-O-(CH_2)_{1-4}-$, $-S-(CH_2)_{1-5}-$, $-(CH_2)_{1-4}-S-(CH_2)_{1-4}-$, $-NR^{11}-(CH_2)_{1-5}-$, $-(CH_2)_{1-4}-NR^{11}-(CH_2)_{1-4}$ or $C_{3-10}$ cycloalkylidene. Typically, Y is $-OCH_2-$, $-CH_2O-$, $C_{1-2}$ alkylene, $C_{2-3}$ alkenylene, $C_{2-3}$ alkynylene, O or a bond, but usually a bond.

In general, $YR^1$ is not any one of H, an unsubstituted $C_{3-10}$ cycloalkyl or $C_1$-$C_6$ alkyl. Typically $YR^1$ is halo or halomethyl-substituted (typically trihalomethyl) phenyl (and usually 1 to 2 substituents in ortho or meta).

X usually is alkylene, alkynylene or alkenylene, typically alkylene, or said hydrocarbons having an intrachain heteroatom, typically O or S. Examples include $-CH_2-$, $-CH(CH_3)-$, $-CH_2-CH_2-$, $-CH_2-CH_2-CH_2-$, $-CH_2-CH_2-CH_2-CH_2$, $-(CH_2)_{2-4}-O-(CH_2)_{2-4}-$, $-(CH_2)_{2-4}-S-(CH_2)_{2-4}-$, $-(CH_2)_{2-4}-NR^{10}-(CH_2)_{2-4}-$, $C_{3-10}$ cycloalkylidene, $C_{2-6}$ alkenylene (such as $-CH=CH-CH_2-$) and $C_{2-6}$ alkynylene. Usually, X is methylene.

$R^3$ generally is aryl or a heterocycle, typically an aromatic heterocycle. The heterocycle generally will contain 1, 2 or 3 N, S or O atoms in the ring, usually is linked to X through a ring carbon atom and typically contains 4 to 6, usually 5, total ring atoms. The $R^3$ aryl or heterocycle ordinarily is substituted with 1, 2 or 3, usually 1, $R^{17}$. $R^3$ optionally is not indolyl.

When $R^3$ is substituted with $R^{17}$ then $R^{17}$ typically is aryl or a heterocycle further substituted with 1 or more, usually 1, 2 or 3, $R^{19}$.

$R^{17}$ is M-Q in some embodiments of the invention. M is a ring. This means any cyclic organic structure, whether carbocyclic or heterocycle, and whether saturated, unsaturated or aromatic or single or fused ring systems. M is chosen from rings that are structurally stable in biological systems. In general, M is a aryl or aromatic heterocycle where heterocycle is defined above.

Q is a spacer group or bond, and is not critical. Typically it is not cyclic and contains from 0 to 6 atoms, generally H, C, $NR^{11}$, O or S, usually C, H and O. A typical embodiment is alkyl having 1 to 6 carbons, normal or secondary, optionally with O or $NR^{11}$ replacing 1 methylene group. Generally Q is 1 to 6 atoms, usually 1 to 3. Q typically is not substituted with $R^{19}$, but if it is then typically it is substituted with one $R^{19}$. $R^{19}$ as substituted on Q usually is alkoxy, halogen, nitro or cyano.

$R^{17}$ typically is selected from the group consisting of $C_{3-10}$ cycloalkyl, $C_{3-10}$ cycloalkenyl, $C_{7-10}$ cycloalkynyl, halogen, aryl, aryloxy, arylthio, arylsulfoxide, arylsulfone, arylsulfonamide, arylalkyl; arylalkyloxy (optionally a benzyloxy); arylalkylthio (optionally a benzylthio); a heterocycle; $C_{1-18}$ hydroxyalkyl, but typically is an aryl or a heterocycle, and where each of said aryl, aryloxy, arylthio, arylsulfoxide, arylsulfone, arylsulfonamide, arylalkyl, arylalkyloxy, arylalkylthio, or heterocycle is optionally substituted with 1 or more $R^{19}$. $R^{17}$ generally is positioned distally to X. Optionally, $R^{17}$ is not $C(O)R^{18}$.

$R^9$ and $R^{18}$ typically are H, OH or alkyl. $R^{18}$ optionally is not $NR^{15}R^{16}$.

$R^5$ typically is not present.

$R^6$ generally is halogen. Optionally, $R^6$ is not $C(O)R^{18}$.

$R^7$, $R^8$, $R^{10}$, $R^{11}$, $R^{13}$, $R^{14}$, $R^{15}$, $R^{16}$, $R^{20}$, $R^{21}$, $R^{23}$ and $R^{24}$ typically are independently H or $C_{1-18}$alkyl.

$R^{12}$ and $R^{22}$ typically are independently OH or alkyl.

$R^{19}$ usually is H; $C_{1-18}$ alkyl; $C_{2-18}$ alkenyl; $C_{2-18}$ alkynyl; $C_{1-18}$alkoxy; alkenyloxy; alkynyloxy; $C_{1-18}$ alkylthio; $C_{3-10}$ cycloalkyl; $C_{4-10}$ cycloalkenyl; $C_{4-10}$ cycloalkynyl; halogen; OH; CN; cyanoalkyl; $NO_2$; $NR^{20}R^{21}$; haloalkyl; haloalkyloxy; $C(=O)R^{18}$; $C(=O)OR^{18}$; OalkenylC$(=O)R^{18}$; $-$OalkylC$(=O)NR^{20}R^{21}$; aryl; heterocycle; $-$OalkylOC$(=O)R^{18}$; $C(=O)N(C_{1-6}$ alkyl), $N(H)S(O)(O)(C_{1-6}$ alkyl); arylalkyloxy; aryloxy; arylalkyloxy; and arylalkyl; each of which is unsubstituted or substituted with 1 or more $=O$; $NR^{20}R^{21}$; CN; alkoxy; heterocycle; haloalkyl- or alkyl-substituted heterocycle; heterocycle linked to $R^{17}$ by alkyl; alkoxyalkoxy or halogen. $R^{18}$ as a subtituent in $R^{19}$ is generally not H. $R^{19}$ typically is independently halogen, $N(R^{20}R^{21})$, unsubstituted or heterocycle (O-containing)—substituted $C_1$-$C_{18}$ alkyl or alkynyl where methylene is substituted with 1-3 oxygen atoms, or is halo-substituted alkyl or alkoxy.

$R^{25}$ and $R^{26}$ usually are not present but, if they are, then typically they are cyclopentyl or cyclohexyl. If the compound is substituted at $R^{25}$ or $R^{26}$, either $R^2$ or $R^4$ is selected from $=O$, $=S$, and $=NR^{27}$, usually $=O$.

M typically is an aromatic ring, usually single or two fused rings, and containing 4 to 10 atoms. Usually, M is hydrocarbon, but also optionally comprises 1 to 3 N, O and/or S heteroatoms.

Substituents optionally are designated with or without bonds. Regardless of bond indications, if a substituent is polyvalent (based on its position in the structure referred to), then any and all possible orientations of the substituent are intended.

Haloalkyl or haloalkyloxy typically are $-CF_3$ or $-OCF_3$.

In certain embodiments of the compound of formula (A) (a) $YR^1$ is not H; (b) $R^2$ is not OH, SH, $=O$ or $=S$; (c) $R^4$ is not $=O$ or $=S$; (d) $YR^1$ contains at least one aryl; (e) X is $CH_2$; (f) $R^3$ contains at least one aryl; (g) if Y is a bond and $R^1$ is an aryl, this aryl is not phenyl substituted with OH and optionally substituted with methyl, methoxy, nitro, dimethylamino, Cl, Br, or F; (h) if Y is a bond and $R^1$ is aryl which is para substituted with OH and optionally further substituted with methyl, methoxy, nitro, diethylamino, Cl, Br or F and X is an alkylene, then $R^3$ is not a heterocycle containing N; (i) if Y is a bond or $(CH_2)_{1-6}$, $R^1$ is H, X is $CH_2$ and $R^3$ is phenyl with 1$R^{17}$, wherein $R^{17}$ is $C(=O)R^{18}$, then $R^{18}$ is selected from H; OH; $C_{1-18}$ alkyl; $C_{2-18}$ alkenyl; $C_{1-18}$ alkoxy; $NR^{15}R^{16}$; aryl, or an amino acid residue linked through an amino group thereof; (j) $R^{18}$ is not a $C_{3-10}$ cycloalkyl or $C_{4-10}$ cycloalkenyl; (k) if Y is a bond or $(CH_2)_{1-6}$, then $R^1$ is an aryl unsubstituted or substituted with one or more $R^6$, heterocycle unsubstituted or substituted with one or more $R^6$, $C_{3-10}$ cycloalkyl unsubstituted or substituted with one or more $R^6$ and $C_{4-10}$ cycloalkenyl unsubstituted or substituted with one or more $R^6$; (l) $-YR^1$ is not H or $C_{1-6}$ alkyl; (m) if Y is a bond or $(CH_2)_{1-6}$, $R^1$ is H, and $R^3$ is a 5 membered heterocycle with one $R^{17}$, wherein $R^{17}$ is $C(=O)R^{18}$ and $R^{18}$ is $NR^{15}R^{16}$, then $R^{15}$ and $R^{16}$ are not a $C_{1-18}$alkyl or a cycloalkyl; (n) if Y is a bond or $(CH_2)_{1-6}$, and $R^1$ is H, and $R^3$ is a 5 membered heterocycle with one $R^{17}$, wherein $R^{17}$ is $C(=O)R^{18}$ then $R^{18}$ is selected from H; OH; $C_{1-18}$ alkyl; $C_{2-18}$ alkenyl; $C_{3-10}$ cycloalkyl; $C_{4-10}$ cycloalkenyl; $C_{1-18}$ alkoxy; aryl or an amino acid residue linked through an amino group thereof; (o)$R^{18}$ is not $NR^{15}R^{16}$; (p) if Y is a bond or $(CH_2)_{1-6}$, $R^1$ is H, X is —$CH_2$— and $R^3$ is phenyl substituted with one $R^{17}$, then $R^{17}$ is independently selected from the group hydrogen; $C_{1-18}$ alkyl; $C_{2-18}$ alkenyl; $C_{2-18}$ alkynyl; $C_{1-18}$ alkoxy; $C_{1-18}$ alkylthio; $C_{3-10}$ cycloalkyl, $C_{3-10}$ cycloalkenyl or $C_{3-10}$ cycloalkynyl; halogen; OH; CN; $NO_2$; $NR^7R^8$; $OCF_3$; haloalkyl; $C(=S)R^{18}$; SH; aryl; aryloxy; arylthio; arylalkyl; arylalkyloxy (optionally a oxybenzyl); arylalkylthio (optionally a benzylthio); 5 or 6 membered heterocycle, oxyheterocycle or thioheterocycle; $C_{1-18}$ hydroxyalkyl; and each of said aryl, aryloxy, arylthio, arylalkyl, arylalkyloxy (optionally a oxybenzyl), arylalkylthio (optionally a benzylthio), 5 or 6 membered heterocycle, oxyheterocycle or thioheterocycle, $C_{1-18}$ hydroxyalkyl is optionally substituted with 1 or more $R^{19}$; (q) $R^{17}$ is not $(C=O)R^{18}$; (r) if Y is a bond or $(CH_2)_{1-6}$, and $R^1$ is H, and $R^3$ is a 5 membered heterocycle with one $R^{17}$, wherein $R^{17}$ is $C(=O)R^{18}$, then $R^{18}$ is selected from H; OH; $C_{1-18}$ alkyl; aryl, $NR^{15}R^{16}$; (s) $R^{18}$ is not $C_{1-18}$ alkoxy; (t) if Y is a bond or $(CH_2)_{1-6}$, and $R^1$ is $H^1$ and $R^3$ is a 5 membered heterocycle with one $R^{17}$, wherein $R^{17}$ is $C(=O)R^{18}$, then $R^{18}$ is selected from OH; $C_{1-18}$ alkyl; $C_{1-18}$ alkoxy; aryl, or $NR^{15}R^{16}$; (t) $R^{16}$ is not H; (u) if Y is a bond, $R^1$ is hydrogen, X is an alkyl and $R^3$ is an aryl thio substituted with 3 $R^{17}$, and 1 $R^{17}$ is OH in para, then the remaining $R^{17}$ are independently selected from the group consisting of hydrogen; $C_{2-18}$ alkenyl; $C_{2-18}$ alkynyl; $C_{1-18}$ alkoxy; $C_{1-18}$ alkylthio; $C_{3-10}$ cycloalkyl, $C_{3-10}$ cycloalkenyl or $C_{3-10}$ cycloalkynyl; halogen; OH; CN; $NO_2$; $NR^7R^8$; $OCF_3$; haloalkyl; $C(=O)R^9$; $C(=S)R^9$; SH; aryl; aryloxy; arylthio; arylalkyl; arylalkyloxy (optionally a oxybenzyl); arylalkylthio (optionally a benzylthio); 5 or 6 membered heterocycle, oxyheterocycle or thioheterocycle; $C_{1-18}$ hydroxyalkyl; and each of said aryl, aryloxy, arylthio, arylalkyl, arylalkyloxy (optionally a oxybenzyl), arylalkylthio (optionally a benzylthio), 5 or 6 membered heterocycle, oxyheterocycle or thioheterocycle, $C_{1-18}$ hydroxyalkyl is optionally substituted with 1 or more $R^{19}$; (v) $R^{17}$ is not a $C_{1-18}$ alkyl; (w1) if Y is a bond, $R^1$ is a hydrogen, X is —$(CH_2—CH_2)$—, then $R^3$ is selected from aryl; aryloxy; aryl-$NR^{10}$—; 5 or 6 membered heterocycle, oxyheterocycle or thioheterocycle; and each of said aryl, aryloxy, aryl-$NR^{10}$—, 5 or 6 membered heterocycle, oxyheterocycle or thioheterocycle is optionally substituted with one or more $R^{17}$; $C_{3-10}$ cycloalkyl, oxycycloalkyl or thiocycloalkyl; $C_{4-10}$ cycloalkenyl with the proviso that the double bond cannot be adjacent to a nitrogen; H with the proviso that if X is an alkylene, an alkenylene or an alkynylene, then X comprises at least 5 carbon atoms; (w2) $R^3$ is not an arylthio; (x) if X is —$(CH_2CH_2)$—S, $R^3$ is not an aryl; (y) if Y is a bond, $R^1$ is H, X is an alkylene and $R^3$ is phenoxy, $R^{17}$ is independently selected from the group hydrogen; $C_{1-18}$ alkyl; $C_{2-18}$ alkenyl; $C_{2-18}$ alkynyl; $C_{1-18}$ alkoxy; $C_{1-18}$ alkylthio; $C_{3-10}$ cycloalkyl, $C_{3-10}$ cycloalkenyl or $C_{3-10}$ cycloalkynyl; halogen; OH; CN; $NO_2$; $NR^7R^8$; $OCF_3$; haloalkyl; $C(=O)R^9$; $C(=S)R^9$; SH; aryl; arylthio; arylalkyl (except benzyl); arylalkyloxy (except oxybenzyl); arylalkylthio (optionally a benzylthio); 5 or 6 membered heterocycle, oxyheterocycle or thioheterocycle; $C_{1-18}$ hydroxyalkyl; and each of said aryl, aryloxy, arylthio, arylalkyl, arylalkyloxy (optionally a oxybenzyl), arylalkylthio (optionally a benzylthio), 5 or 6 membered heterocycle, oxyheterocycle or thioheterocycle or $C_{1-18}$ hydroxyalkyl is optionally substituted with 1 or more $R^{19}$; (z) if $R^3$ is phenoxy, $R^{17}$ is not benzyl, phenoxy or oxybenzyl; (aa) if $XR^3$ is fluorobenzyl, $R^2$, $R^3$, $R^4$ are $R^1=H$ and Y is $NR^{11}$, $R^{11}$ is selected from H; $C_{1-18}$ alkyl; $C_{1-18}$ alkenyl; $C_{3-10}$ cycloalkyl; $C_{4-10}$ cycloalkenyl; aryl; 5-6 membered heterocycle or an amino acid residue linked through a carboxyl group thereof; (bb) $R^{11}$ is not methyl or $C(=O)R^{12}$; (cc) if X is $CH_2$ and $R^3$ is a phenyl substituted in para with Cl, and Y is $CH_2$, then $R^1$ is not piperazinyl; (dd) if X is $CH_2$ and $R^3$ is a phenyl substituted in para with Cl, and Y is $CH_2$, then $R^1$ heterocycle is aromatic; (ee) if $R^5$ is an aryl, aryloxy or benzyl group, $R^1$ is not H or $C_{3-10}$ alkyl; (ff) if $R^1$ is H or $C_{3-10}$ alkyl, then $R^5$ is absent or is selected from hydrogen, $C_{1-18}$ alkyl; $C_{2-18}$ alkenyl; $C_{2-18}$ alkynyl; $C_{1-18}$ alkoxy; $C_{1-18}$ alkylthio; halogen; OH; CN; $NO_2$; $NR^7R^8$; $OCF_3$; haloalkyl; $C(=O)R^9$; $C(=S)R^9$; SH; arylthio; arylalkyl (except benzyl); $C_{1-18}$ hydroxyalkyl; $C_{3-10}$ cycloalkyl; $C_{3-10}$ cycloalkyloxy; $C_{3-10}$ cycloalkylthio $C_{3-10}$ cycloalkenyl; $C_{3-10}$ cycloalkynyl; 5 or 6 membered heterocycle, oxyheterocycle or thioheterocycle; (gg) $R^5$ is not aryl, aryloxy or benzyl; (hh) $YR^1$ is not hydrogen, unsubstituted $C_{3-10}$ cycloalkyl, or $C_{1-6}$alkyl; (ii) $YR^1$ is not phenyl para substituted with OH; (jj) if $R^1$ is not H, Y is not $NR^{11}$ with $R^{11}$ is $C_{1-6}$ alkyl or methyl; (kk) $YR^1$ is not monomethylamino; (ll) if $R^1$ is a phenyl substituted with one $R^6$, then $R^6$ is $C(=O)R^{18}$ and $R^{18}$ is t-butoxy; (mm) $R^1$ is not piperidinyl and is not piperazinyl subsituted with methyl; (nn) $YR^1$ is not one of the substituents designated $R^{13}$ in column 5, lines 22-38 of U.S. Pat. No. 5,486,525 or its family members; (oo) $R^2$ and/or $R^5$ are none of the substituents collectively designated $R^{14}$ and $R^{15}$ in column 5, lines 38-53 of U.S. Pat. No. 5,486,525 or its family members; (pp) $XR^3$ is not the substructure —$(CH_2)_n$-Het-$C(O)$—$N(R^1)(R^2)$ using the group designations set forth on column 1, line 41 to column 2 line 24 of U.S. Pat. No. 4,990,518 and the comparable disclosure in any member of the patent family of U.S. Pat. No. 4,990,518; (qq) $XR^3$ is not the substructure —$(CH_2)_n$—Y—$C(O)$—$N(R^1)(R^2)$ using the group designations set forth on column 1, line 49 to column 2 line 38 of U.S. Pat. No. 5,302,601 and the comparable disclosure in any member of the patent family of U.S. Pat. No. 5,302,601; (rr) $R^2$ and $R^4$ are not both =O or =S; and/or (alone or in any combination) (ss) $R^5$ contains none of the substituents designated as <<Ar>> in WO 00/39127 (incorporated expressly herein by reference), in particular aryl, aryl phenoxy, or benzyl; (tt) $YR^1$ optionally is not a non-aromatic hereocyclic ring containing 5 or 6 total ring atoms and 1 or 2 N atoms; (uu) $YR^1$ optionally is not a non-aromatic heterocyclic ring containing 1 or 2 N atoms wherein one of the N atoms is linked to the imidazole ring; (vv) $YR^1$ optionally is not a 5-membered non-aromatic heterocyclic ring which contains 1 N atom and is substituted with amino; (ww) $R^{26}$ optionally is not normal or secondary alkyl, or benzyl.

The exclusions or embodiments herein are not to be interpreted as teaching or suggesting any preferability or lack thereof for any use of the compounds herein, but instead are merely subgeneric designations.

Optionally, the compounds of this invention also exclude all methylene homologues of heretofore known compounds.

According to a particular aspect, the present invention relates to compounds of the formula (A) wherein $R^1$ is a phenyl optionally substituted with a benzyloxy, and wherein $R^{19}$ at meta is phenyl optionally substituted with a halogen, (particularly chloro) in para, and $R^{19}$ at ortho is H, nitro, amino, mono- or di($C_{1-6}$ alkyl)-substituted amino, NHC(O)($C_{1-6}$ alkyl); methoxysulfonamide or $C(O)R^{22}$, wherein $R^{22}$ is $NR^{23}R^{24}$ as defined below. Optionally $R^{23}$ and $R^{24}$ are $C_{1-6}$ alkyl taken together to form a hydroxy-substituted 6-membered saturated N-heterocycle.

An embodiment of the present invention relates to compounds of formula (A) of this invention, pharmaceutically acceptable compositions, salts, tautomers, and isomers thereof and their antiviral uses, wherein:

U is N;

$R^1$ is selected from phenyl substituted with 0-3 $R^6$; 5 or 6 membered heterocycle containing 1-3 heteroatoms selected from the group O, N, and S, substituted with 0-2 $R^6$; 1-naphthyl substituted with 0-3 $R^6$; 2-naphthyl substituted with 0-3 $R^6$; $C_{3-7}$ cycloalkyl; $C_{4-10}$ cycloalkenyl;

$R^2$, $R^4$ and $R^5$ are independently selected from hydrogen; straight or branched $C_{1-6}$ alkoxy; straight or branched $C_{1-6}$ alkyl; F; Cl; Br; I; OH; CN; $NO_2$; $NR^7R^8$; $OCF_3$; $CF_3$; $C(=O)R^9$; phenyl; phenoxy; benzyl; hydroxymethyl, or in the case of $R^5$ optionally is unsubstituted;

X is selected from the group —$CH_2$—; —$CH(CH_3)$—; —$CH_2$—$CH_2$—$CH_2$—; —$OCH_2$—$CH_2$—; —$CH=CH$—$CH_2$—;

$R^3$ is selected from phenyl substituted with 0-3 $R^{17}$; (benzoannellated) 5 or 6 membered aromatic heterocycle containing 1-3 heteroatoms selected from the group O, N, and S, substituted with 0-2 $R^{17}$; 1-naphthyl substituted with 0-3 $R^{17}$; 2-naphthyl substituted with 0-3 $R^{17}$; $C_{3-7}$ cycloalkyl; $C_{4-7}$ cycloalkenyl with the proviso that the double bond cannot be adjacent to a nitrogen;

$R^6$ and $R^{17}$ are independently selected from the group H; straight or branched $C_{1-6}$ alkoxy; straight or branched $C_{1-6}$ alkyl; F; Cl; Br; I; OH; CN; $NO_2$; $NR^{13}R^{14}$; $OCF_3$; $CF_3$; $C(=O)R^{18}$; phenyl; phenoxy; benzyl; hydroxymethyl;

$R^7$ and $R^8$ are independently selected from H; straight or branched $C_{1-6}$ alkyl; phenyl; $C(=O)R^{12}$; alternatively, $R^7$ and $R^8$, together with the nitrogen to which they are attached, combine to form a 5-6 membered ring;

$R^9$ and $R^{18}$ are independently selected from H; OH; straight or branched $C_{1-6}$ alkyl; straight or branched $C_{1-6}$ alkoxy; $NR^{15}R^{16}$; phenyl;

$R^{12}$ is selected from the group H; $C_{1-6}$ straight or branched alkyl; phenyl;

$R^{15}$ and $R^{16}$ are independently selected from the group H; $C_{1-6}$ straight or branched alkyl; phenyl; and Y is a bond.

One embodiment of a second aspect of the present invention relates to compounds according to the general formula (A), pharmaceutically acceptable compositions, salts, tautomers, polymorphs and isomers thereof, and their antiviral uses, wherein:

U is N;

$R^1$ is selected from hydrogen; aryl unsubstituted or substituted with one or more $R^6$, heterocycle unsubstituted or substituted with one or more $R^6$, $C_{3-10}$ cycloalkyl unsubstituted or substituted with one or more $R^6$ and $C_{4-10}$ cycloalkenyl unsubstituted or substituted with one or more $R^6$;

Y is selected from the group consisting of a single bond, 0; $S(O)_m$ (where m is an integer from 0 to 2); $NR^{11}$; and a divalent, saturated or unsaturated, substituted or unsubstituted $C_1$-$C_{10}$ hydrocarbon group optionally including one or more heteroatoms in the main chain, said heteroatoms being selected from the groups consisting of O, S, and N; such as $C_{1-6}$ alkylene, $C_{2-6}$ alkenylene, $C_{2-6}$ alkynylene, —$O(CH_2)_{1-5}$—, —$(CH_2)_{1-4}$—O—$(CH_2)_{1-4}$—, —S—$(CH_2)_{1-5}$—, —$(CH_2)_{1-4}$—S—$(CH_2)_{1-4}$—, —$NR^{11}$—$(CH_2)_{1-5}$—, —$(CH_2)_{1-4}$—$NR^{11}$—$(CH_2)_{1-4}$— and $C_{3-10}$ cycloalkylidene;

Each $R^2$ and $R^4$ is independently selected from the group consisting of hydrogen $C_{1-18}$ alkyl; $C_{2-18}$ alkenyl; $C_{2-18}$ alkynyl; $C_{1-18}$ alkoxy; $C_{1-18}$ alkylthio; halogen; OH; CN; $NO_2$; $NR^7R^8$; $OCF_3$; haloalkyl; $C(=O)R^9$; $C(=S)$ $R^9$; SH; aryl; aryloxy; arylthio; arylalkyl; $C_{1-18}$ hydroxyalkyl; $C_{3-10}$ cycloalkyl; $C_{3-10}$ cycloalkyloxy; $C_{3-10}$ cycloalkylthio; $C_{3-10}$ cycloalkenyl; $C_{3-10}$ cycloalkynyl; 5 or 6 membered heterocycle, oxyheterocycle or thioheterocycle;

X is selected from the group consisting of a divalent, saturated or unsaturated, substituted or unsubstituted $C_1$-$C_{10}$ hydrocarbon group optionally including one or more heteroatoms in the main chain (provided that the heteroatom is not linked to N of the nucleus), said heteroatoms being selected from the group consisting of O, S, and N; such as $C_{1-6}$ alkylene, (for example —$CH_2$—, —$CH(CH_3)$—, —$CH_2$—$CH_2$—, —$CH_2$—$CH_2$—$CH_2$—$CH_2$—$CH_2$—$CH_2$—$CH_2$—), —$(CH_2)_{2-4}$—O—$(CH_2)_{2-4}$—, —$(CH_2)_{2-4}$—S—$(CH_2)_{2-4}$—, —$(CH_2)_{2-4}$—$NR^{10}$—$(CH_2)_{2-4}$—, $C_{3-10}$ cycloalkylidene, $C_{2-6}$ alkenylene (such as —$CH=CH$—$CH_2$—), $C_{2-6}$ alkynylene;

$R^3$ is selected from the group consisting of aryl; aryloxy; arylthio; aryl-$NR^{10}$—; 5 or 6 membered heterocycle, oxyheterocycle or thioheterocycle; and each of said aryl, aryloxy, arylthio, aryl-$NR^{10}$—, 5 or 6 membered heterocycle, oxyheterocycle or thioheterocycle is optionally substituted with one or more $R^{17}$; $C_{3-10}$ cycloalkyl, oxycycloalkyl or thiocycloalkyl; $C_{4-10}$ cycloalkenyl with the proviso that the double bond cannot be adjacent to a nitrogen; H with the proviso that if X is an alkylene, an alkenylene or an alkynylene, then X comprises at least 5 carbon atoms;

$R^5$ is independently absent or selected from the group consisting of hydrogen; $C_{1-18}$ alkyl; $C_{2-18}$ alkenyl; $C_{2-18}$ alkynyl; $C_{1-18}$ alkoxy; $C_{1-18}$ alkylthio; halogen; OH; CN; $NO_2$; $NR^7R^8$; $OCF_3$; haloalkyl; $C(=O)R^9$; $C(=S)$ $R^9$; SH; aryl; aryloxy; arylthio; arylalkyl; $C_{1-18}$ hydroxyalkyl; $C_{3-10}$ cycloalkyl; $C_{3-10}$ cycloalkyloxy; $C_{3-10}$ cycloalkylthio $C_{3-10}$ cycloalkenyl; $C_{3-10}$ cycloalkynyl; 5 or 6 membered heterocycle, oxyheterocycle or thioheterocycle;

Each $R^6$ and $R^{17}$ is independently selected from the group consisting of hydrogen; $C_{1-18}$ alkyl; $C_{2-18}$ alkenyl; $C_{2-18}$ alkynyl; $C_{1-18}$ alkoxy; $C_{1-18}$ alkylthio; $C_{3-10}$ cycloalkyl, $C_{3-10}$ cycloalkenyl or $C_{3-10}$ cycloalkynyl; halogen; OH; CN; $NO_2$; $NR^7R^8$; $OCF_3$; haloalkyl; $C(=O)R^9$; $C(=S)$ $R^9$; SH; aryl; aryloxy; arylthio; arylalkyl; arylalkyloxy (optionally a oxybenzyl); arylalkylthio (optionally a benzylthio); 5 or 6 membered heterocycle, oxyheterocycle or thioheterocycle; $C_{1-18}$ hydroxyalkyl; and each of said aryl, aryloxy, arylthio, arylalkyl, arylalkyloxy (optionally a oxybenzyl), arylalkylthio (optionally a benzylthio), 5 or 6 membered heterocycle, oxyheterocycle or thioheterocycle, $C_{1-18}$ hydroxyalkyl is optionally substituted with 1 or more $R^{19}$.

Each $R^7$ and $R^8$ is independently selected from the group consisting of H; $C_{1-18}$ alkyl; $C_{1-18}$ alkenyl; aryl; $C_{3-10}$ cycloalkyl; $C_{4-10}$ cycloalkenyl; 5-6 membered heterocycle; $C(=O)R^{12}$; $C(=S)R^{12}$; an amino acid residue linked through a carboxyl group thereof; alternatively, $R^7$ and $R^8$, together with the nitrogen to which they are attached, combine to form a 5-6 membered heterocycle;

Each $R^9$ and $R^{18}$ is independently selected from the group consisting of H; OH; $C_{1-18}$ alkyl; $C_{2-18}$ alkenyl; $C_{3-10}$ cycloalkyl; $C_{4-10}$ cycloalkenyl; $C_{1-18}$ alkoxy; $NR^{15}R^{16}$; aryl an amino acid residue linked through an amino group thereof;

Each $R^{10}$ and $R^{11}$ is independently selected from the group the group consisting of H; $C_{1-18}$ alkyl; $C_{1-18}$ alkenyl; $C_{3-10}$ cycloalkyl; $C_{4-10}$ cycloalkenyl; aryl; $C(=O)R^{12}$;

5-6 membered heterocycle; an amino acid residue linked through a carboxyl group thereof;

$R^{12}$ is independently selected from the group consisting of H; $C_{1-18}$ alkyl; $C_{2-18}$ alkenyl; aryl; $C_{3-10}$ cycloalkyl; $C_{4-10}$ cycloalkenyl; an amino acid residue linked through an amino group thereof;

Each $R^{15}$ and $R^{16}$ is independently selected from the group consisting of H; $C_{1-18}$ alkyl; $C_{2-18}$ alkenyl; $C_{2-18}$ alkynyl; aryl; $C_{3-10}$ cycloalkyl; $C_{4-10}$ cycloalkenyl; an amino acid residue linked through a carboxyl group thereof;

$R^{19}$ is independently selected from the group consisting of H; $C_{1-18}$alkyl, preferably $C_{1-6}$ alkyl; $C_{2-18}$ alkenyl; $C_{2-18}$ alkynyl; $C_{1-18}$ alkoxy, preferably $C_{1-6}$ alkoxy; $C_{1-18}$ alkylthio; $C_{3-10}$ cycloalkyl; $C_{4-10}$ cycloalkenyl; $C_{4-10}$ cycloalkynyl; halogen; OH; CN; $NO_2$; $NR^{20}R^{21}$; $OCF_3$; haloalkyl; $C(=O)R^{22}$; $C(=S)R^{22}$; SH; $C(=O)N(C_{1-6}$ alkyl), $N(H)S(O)(O)(C_{1-6}$ alkyl); aryl; aryloxy; arylthio; arylalkyl; and each of said aryl, aryloxy, arylthio, arylalkyl substituted with 1 or more halogens, particularly a phenyl substituted with 1-2 halogens; hydroxyalkyl; 5 or 6 membered heterocycle, oxyheterocycle or thioheterocycle each unsubstituted or substituted with 1 or more halogens;

Each $R^{20}$ and $R^{21}$ is independently selected from the group consisting of H; $C_{1-18}$ alkyl, preferably $C_{1-6}$ alkyl; $C_{2-18}$ alkenyl; $C_{2-18}$ alkynyl; aryl; $C_{3-10}$ cycloalkyl; $C_{4-10}$ cycloalkenyl; $C(=O)R^{12}$, $C(=S)R^{12}$;

$R^{22}$ is independently selected from H; OH; $C_{1-18}$ alkyl; $C_{2-18}$ alkenyl; $C_{1-18}$ alkoxy; $NR^{23}R^{24}$; aryl; $C_{3-10}$ cycloalkyl; $C_{4-10}$ cycloalkenyl;

Each $R^{23}$ and $R^{24}$ is independently selected from the group the group consisting of H; $C_{1-18}$ alkyl, preferably $C_{2-3}$ alkyl, wherein $C_{2-3}$ alkyl taken together with N of $R^{22}$ can form a saturated heterocycle, which heterocycle is optionally substituted with OH or aryl or an amino acid residue.

An embodiment relating to a third aspect of the present invention relates to compounds according to the general formula (A), pharmaceutically acceptable compositions, salts, tautomers, polymorphs and isomers thereof, and their antiviral uses, wherein:

U is N;

$R^1$ is selected from hydrogen; phenyl unsubstituted or substituted with 1-3 $R^6$; 5 or 6 membered heterocycle, optionally benzo-added, containing 1-3 heteroatoms selected from the group O, N, and S, unsubstituted or substituted with 1-2 $R^6$; 1-naphthyl unsubstituted or substituted with 1-3 $R^6$; 2-naphthyl unsubstituted or substituted with 1-3 $R^6$; $C_{3-10}$ cycloalkyl, particularly $C_{3-7}$ cycloalkyl; $C_{5-7}$ cycloalkenyl with the proviso that the double bond cannot be adjacent to a nitrogen;

Y is selected from the group $-(CH_2)_{0-6}-$; O; S; $NR^{11}$; $-CH(CH_3)-$; $-OCH_2-$; $-CH_2O-$; $-OCH_2-CH_2-$; $-CH_2-CH_2O-$; $-CH_2-O-CH_2-$; $-(CH_2)_{0-5}-S-$; $-S-(CH_2)_{0-5}-$; $-(CH_2)_{0-2}-S-(CH_2)_{0-2}-$; $-NR^{11}-(CH_2)_{0-5}-$; $-(CH_2)_{0-5}-NR^{11}-$; $-CH_2-NR^{11}-CH_2-$; $-C(CH_3)_2-$; (cis or trans) $-CH_2-CH=CH-$; (cis or trans)- $CH=CH-CH_2-$;

Each $R^2$, $R^4$ and $R^5$ is independently selected from hydrogen; straight or branched $C_{1-18}$ alkoxy, particularly $C_{1-6}$ alkoxy; straight or branched $C_{1-18}$ alkyl particularly $C_{1-6}$alkyl; F; Cl; Br; I; OH; CN; $NO_2$; $NR^7R^8$; $OCF_3$; $CF_3$; $C(=O)R^9$; phenyl; phenoxy; benzyl; hydroxymethyl or, in the case of R5, optionally is absent;

X is selected from the group $-CH_2-$; $-CH(CH_3)-$; $-CH_2-CH_2-$; $-CH_2-CH_2-CH_2-$; $-CH_2-CH_2-CH_2-$; $-OCH_2-CH_2-$; $-SCH_2-CH_2-$; $-NR^{10}-CH_2-CH_2-$; $C_{3-7}$ cycloalkylidene; $-C(CH_3)_2-$; $-CH_2-CH(CH_3)-CH_2-$; $-CH(CH_3)-CH_2-CH_2-$; $-CH_2-CH_2-CH(CH_3)-$; $-CH=CH-CH_2-$;

$R^3$ is selected from unsubstituted or phenyl substituted with 1-3 $R^{17}$; 5 or 6 membered heterocycle, containing 1-3 heteroatoms selected from the group O, N, and S, unsubstituted or substituted with 1-2 $R^{17}$; 1-naphthyl unsubstituted or substituted with 1-3 $R^{17}$; 2-naphthyl unsubstituted or substituted with 1-3 $R^{17}$; $C_{3-10}$ cycloalkyl, particularly $C_{3-7}$ cycloalkyl; $C_{5-7}$ cycloalkenyl with the proviso that the double bond cannot be adjacent to a nitrogen;

Each $R^6$ and $R^{17}$ is independently selected from the group H; straight or branched $C_{1-6}$ alkoxy; straight or branched $C_{1-6}$ alkyl; F; Cl; Br; I; OH; CN; $NO_2$; $NR^{13}R^{14}$; $OCF_3$; $CF_3$; $C(=O)R^{18}$; unsubstituted phenyl or phenyl substituted with 1-3 $R^{19}$; 5 or 6 membered heterocycles, optionally benzo-added, containing 1-3 heteroatoms selected from O, N and S, unsubstituted or substitued with 1 or 2 $R^{19}$; 2-naphthyl unsubstituted or substituted with 1-3 $R^{19}$; $C_{3-7}$cycloalkyl; $C_{5-7}$ cycloalkenyl, phenoxy; benzyl; hydroxymethyl;

Each $R^7$ and $R^8$ is independently selected from H; straight or branched $C_{1-18}$ alkyl, preferably $C_{1-6}$ alkyl; phenyl; $C(=O)R^{12}$; alternatively, $R^7$ and $R^8$, together with the nitrogen to which they are attached, combine to form a 5-6 membered ring;

Each $R^9$ and $R^{18}$ is independently selected from H; OH; straight or branched $C_{1-18}$ alkyl, preferably $C_{1-6}$ alkyl; straight or branched $C_{1-18}$ alkoxy, preferably $C_{1-6}$ alkoxy; $NR^{15}R^{16}$; phenyl;

Each $R^{10}$ and $R^{11}$ is independently selected from the group H; $C_{1-18}$alkyl, preferably $C_{1-6}$ straight or branched alkyl; phenyl;

Each $R^{12}$ is selected from the group H; $C_{1-18}$ alkyl, preferably $C_{1-6}$ straight or branched alkyl; phenyl;

Each $R^{13}$ and $R^{14}$ is independently selected from H; straight or branched $C_{1-18}$ alkyl, preferably $C_{1-6}$alkyl; phenyl; $C(=O)R^{12}$;

Each $R^{15}$ and $R^{16}$ is independently selected from the group H; $C_{1-6}$ straight or branched alkyl; phenyl;

$R^{19}$ is selected from the group H; straight or branched $C_{1-6}$ alkoxy; straight or branched $C_{1-6}$ alkyl; F; Cl, Br; OH; NO2; $NR^{20}R^{21}$; $OCF_3$, $C(=O)R^{22}$; phenyl; phenoxy; benzyl; hydroxymethyl;

Each $R^{20}$ and $R^{21}$ is independently selected from H; straight or branched $C_{1-18}$ alkyl, preferably $C_{1-6}$alkyl; phenyl; $C(=O)R^{12}$;

$R^{22}$ is selected from H; OH; straight or branched $C_{1-6}$ alkyl; straight or branched $C_{1-18}$ alkoxy, preferably $C_{1-6}$ alkoxy; $NR^{23}R^{24}$; phenyl;

Each $R^{23}$ and $R^{24}$ is independently selected from the group H; $C_{1-18}$ alkyl, preferably $C_{1-6}$ straight or branched alkyl; phenyl.

An embodiment of a fourth aspect of the present invention relates to compounds of formula (A1) wherein $R^1$ is directly linked to the imidazo[4,5-d]pyrimidine ring structure, pharmaceutically acceptable compositions, salts, tautomers, polymorphs and isomers thereof and their use in a treatment of viral infection or to manufacture a medicament to treat viral infections, wherein:

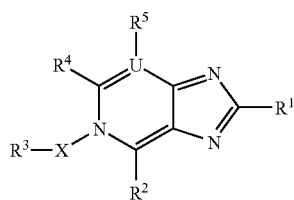

(A1)

U is N;
R¹ is selected from phenyl substituted with 0-3 R⁶; 5 or 6 membered heterocycle containing 1-3 heteroatoms selected from the group O, N, and S, substituted with 0-2 R⁶; 1-naphthyl substituted with 0-3 R⁶; 2-naphthyl substituted with 0-3 R⁶; $C_{3-7}$ cycloalkyl; $C_{4-10}$ cycloalkenyl;
R², R⁴ and R⁵ are independently selected from hydrogen; straight or branched $C_{1-6}$ alkoxy; straight or branched $C_{1-6}$ alkyl; F; Cl; Br; I; OH; CN; NO₂; NR⁷R⁸; OCF₃; CF₃; C(=O)R⁹; phenyl; phenoxy; benzyl; hydroxymethyl or, in the case of R5, optionally is absent;
X is selected from the group —CH₂—; —CH(CH₃)—; —CH₂—CH₂—; —CH₂—CH₂—CH₂—; —CH₂—CH₂—CH₂—CH₂; —OCH₂—CH₂—; —SCH₂—CH₂—; —NR¹⁰—CH₂—CH₂—; $C_{3-7}$ cycloalkylidene; —C(CH₃)₂—; —CH₂—CH(CH₃)—CH₂—; —CH(CH₃)—CH₂—CH₂—; —CH₂—CH₂—CH(CH₃)—; —CH=CH—CH₂—;
R³ is selected from phenyl substituted with 0-3 R¹⁷; (benzoannellated) 5 or 6 membered aromatic heterocycle containing 1-3 heteroatoms selected from the group O, N, and S, substituted with 0-2 R¹⁷; 1-naphthyl substituted with 0-3 R¹⁷; 2-naphthyl substituted with 0-3 R¹⁷; $C_{3-7}$ cycloalkyl; $C_{4-10}$ cycloalkenyl with the proviso that the double bond cannot be adjacent to a nitrogen;
R⁶ and R¹⁷ are independently selected from the group H; straight or branched $C_{1-6}$ alkoxy; straight or branched $C_{1-6}$ alkyl; F; Cl; Br; I; OH; CN; NO₂; NR¹³R¹⁴; OCF₃; CF₃; C(=O)R¹⁸; phenyl; phenoxy; benzyl; hydroxymethyl;
R⁷ and R⁸ are independently selected from H; straight or branched $C_{1-6}$ alkyl; phenyl; C(=O)R¹² or R⁷ and R⁸, together with the nitrogen to which they are attached, combine to form a 5-6 membered ring;
R⁹ and R¹⁸ are independently selected from H; OH; straight or branched $C_{1-6}$ alkyl; straight or branched $C_{1-6}$ alkoxy; NR¹⁵R¹⁶; phenyl;
R¹⁰ is selected from the group H; $C_{1-6}$ straight or branched alkyl; phenyl;
R¹² is selected from the group H; $C_{1-6}$ straight or branched alkyl; phenyl;
R¹³ and R¹⁴ are independently selected from H; straight or branched $C_{1-6}$ alkyl; phenyl; C(=O)R¹²;
R¹⁵ and R¹⁶ are independently selected from the group H; $C_{1-6}$ straight or branched alkyl; phenyl.

An embodiment of a fifth aspect of the present invention relates to compounds of formula (A1), pharmaceutically acceptable compositions, salts, tautomers, polymorphs and isomers and their use in a treatment of viral infection or to manufacture a medicament to treat viral infection, wherein:
U is N;
R¹ is selected from phenyl unsubstituted or substituted with 1-3 R⁶; 5 or 6 membered heterocycle containing 1-3 heteroatoms selected from the group O, N, and S, unsubstituted or substituted with 1-2 R⁶; 1-naphthyl unsubstituted or substituted with 1-3 R⁶; 2-naphthyl unsubstituted or substituted with 1-3 R⁶; $C_{3-7}$ cycloalkyl; $C_{5-7}$ cycloalkenyl;
R² and R⁴ are hydrogen;
R⁵ is absent;
X is selected from the group —CH₂—; —CH(CH₃)—; —CH₂—CH₂—CH₂—; —OCH₂—CH₂—; —CH=CH—CH₂—;
R³ is selected from phenyl unsubstituted or substituted with 1-3 R¹⁷; (benzoannellated) 5 or 6 membered aromatic heterocycle containing 1-3 heteroatoms selected from the group O, N, and S, unsubstituted or substituted with 1-2 R¹⁷; 1-naphthyl unsubstituted or substituted with 1-3 R¹⁷; 2-naphthyl substituted with 0-3 R¹⁷; $C_{3-7}$ cycloalkyl; $C_{1-7}$ cycloalkenyl with the proviso that the double bond cannot be adjacent to a nitrogen;
Each R⁶ and R¹⁷ is independently selected from the group H; straight or branched $C_{1-6}$ alkoxy; straight or branched $C_{1-6}$ alkyl; F; Cl; Br; I; OH; CN; NO₂; NR¹³R¹⁴; OCF₃; CF₃; C(=O)R⁹; phenyl; phenoxy; benzyl; hydroxymethyl;
R⁹ is selected from H; OH; straight or branched $C_{1-6}$ alkyl; straight or branched $C_{1-6}$ alkoxy; NR¹⁵R¹⁶; phenyl;
R¹² is selected from the group H; $C_{1-6}$ straight or branched alkyl; phenyl;
Each R¹³ and R¹⁴ is independently selected from H; straight or branched $C_{1-6}$ alkyl; phenyl; C(=O)R¹²; and
Each R¹⁵ and R¹⁶ is independendly selected from the group H; $C_{1-6}$ straight or branched alkyl; phenyl;

An embodiment of present invention in its sixth aspect comprises the compounds of formula (A1), pharmaceutically acceptable compositions salts, tautomers, and isomers thereof and their use in a treatment of viral infection or to manufacture a medicament to treat viral infection, wherein:
U is N;
R¹ is selected from phenyl unsubstituted or substituted with 1-3 R⁶; 5 or 6 membered heterocycle containing 1-3 heteroatoms selected from the group O, N, and S, unsubstituted or substituted with 1-2 R⁶; 1-naphthyl unsubstituted or substituted with 1-3 R⁶; 2-naphthyl unsubstituted or substituted with 1-3 R⁶;
R² and R⁴ are hydrogen;
R⁵ is absent;
X is selected from —CH₂—; —CH(CH₃)—; —CH₂—CH₂—CH₂—; —OCH₂—CH₂—; —CH=CH—CH₂—;
R³ is selected from phenyl unsubstituted or substituted with 1-3 R¹⁷; 5 or 6 membered aromatic heterocycle containing 1-3 heteroatoms selected from the group O, N, and S, unsubstituted or substituted with 1-3 R¹⁷; 1-naphthyl unsubstituted or substituted with 1-3 R¹⁷; 2-naphthyl unsubstituted or substituted with 1-3 R¹⁷;
Each R⁶ and R¹⁷ is independently selected from the group H; straight or branched $C_{1-6}$ alkoxy; straight or branched $C_{1-6}$ alkyl; F; Cl; Br; I; OH; CN; NO₂; NR¹³R¹⁴; OCF₃; CF₃; C(=O)R⁹; phenyl; phenoxy; benzyl; hydroxymethyl;
R⁹ is selected from H; OH; straight or branched $C_{1-6}$ alkyl; straight or branched $C_{1-6}$ alkoxy; NR¹⁵R¹⁶; phenyl;
R¹² is selected from the group H; $C_{1-6}$ straight or branched alkyl; phenyl;
Each R¹³ and R¹⁴ is independently selected from H; straight or branched $C_{1-6}$ alkyl; phenyl; C(=O)R¹²; and
Each R¹⁵ and R¹⁶ is independently selected from the group H; $C_{1-6}$ straight or branched alkyl; and phenyl.

An embodiment of present invention in its seventh aspect comprises compounds of formula (A1), pharmaceutically acceptable compositions, salts, tautomers, and isomers thereof and their use in a treatment of viral infection or to manufacture a medicament to treat viral infection, wherein:
U is N;
R$^1$ is selected from phenyl unsubstituted or substituted with 1-3 R$^6$; 5 or 6 membered heterocycle containing 1-3 heteroatoms selected from the group O, N, and S, unsubstituted or substituted with 1-2 R$^6$; 1-naphthyl unsubstituted or substituted with 1-3 R$^6$; 2-naphthyl unsubstituted or substituted with 1-3 R$^6$;
R$^2$ and R$^4$ are hydrogen;
R$^5$ is absent;
X is selected from —CH$_2$—; —CH(CH$_3$)—; —CH$_2$—CH$_2$—CH$_2$—; —OCH$_2$—CH$_2$—; —CH═CH—CH$_2$—;
R$^3$ is selected from phenyl unsubstituted or substituted with 1-3 R$^{17}$; 5 or 6 membered aromatic heterocycle containing 1-3 heteroatoms selected from the group O, N, and S, unsubstituted or substituted with 1-2 R$^{17}$; 1-naphthyl substituted with 0-3 R$^{17}$; 2-naphthyl unsubstituted or substituted with 1-3 R$^{17}$;
Each R$^6$ and R$^{17}$ is independently selected from hydrogen; straight or branched C$_{1-6}$ alkoxy; straight or branched C$_{1-6}$ alkyl; F; Cl; Br; I; OH; CN; NO$_2$; NR$^{13}$R$^{14}$; OCF$_3$; CF$_3$; C(═O)R$^9$; phenyl; phenoxy; benzyl; hydroxymethyl;
R$^9$ is selected from H; OH; straight or branched C$_{1-6}$ alkyl; straight or branched C$_{1-6}$ alkoxy; NR$^{15}$R$^{16}$; phenyl;
R$^{12}$ is selected from the group H; C$_{1-6}$ straight or branched alkyl; phenyl;
Each R$^{13}$ and R$^{14}$ is independently selected from H; straight or branched C$_{1-6}$ alkyl; phenyl; C(═O)R$^{12}$; and
Each R$^{15}$ and R$^{16}$ is independently selected from the group H; C$_{1-6}$ straight or branched alkyl; and phenyl.

An embodiment of the present invention in its eighth aspect relates to compounds of the formula (A2), pharmaceutically acceptable compositions, salts, tautomers, polymorphs and isomers thereof and their use in a treatment of viral infection or to manufacture a medicament to treat viral infection

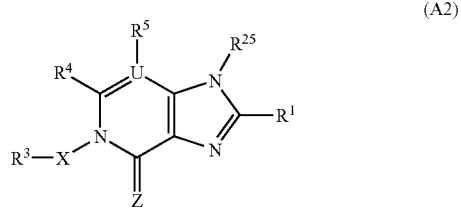

(A2)

wherein
U is N;
R$^1$ is selected from hydrogen; aryl unsubstituted or substituted with one or more R$^6$, heterocycle unsubstituted or substituted with one or more R$^6$, C$_{3-10}$ cycloalkyl unsubstituted or substituted with one or more R$^6$ and C$_{4-10}$ cycloalkenyl unsubstituted or substituted with one or more R$^6$;
X is selected from the group consisting of a divalent, saturated or unsaturated, substituted or unsubstituted C$_1$-C$_{10}$ hydrocarbon group optionally including one or more heteroatoms in the main chain (provided that the heteroatom is not linked to N of the nucleus), said heteroatoms being selected from the group consisting of O, S, and N; such as C$_{1-6}$ alkylene, (for example —CH$_2$—, —CH(CH$_3$)—, —CH$_2$—CH$_2$—, —CH$_2$—CH$_2$—CH$_2$—, —CH$_2$—CH$_2$—CH$_2$—CH$_2$), —(CH$_2$)$_{2-4}$—O—(CH$_2$)$_{2-4}$—, —(CH$_2$)$_{2-4}$—S—(CH$_2$)$_{2-4}$—, —(CH$_2$)$_{2-4}$—NR$^{10}$—(CH$_2$)$_{2-4}$—, C$_{3-10}$ cycloalkylidene, C$_{2-6}$ alkenylene (such as —CH═CH—CH$_2$—), C$_{2-6}$ alkynylene;
R$^3$ is selected from the group consisting of aryl; aryloxy; arylthio; aryl-NR$^{10}$—; 5 or 6 membered heterocycle, oxyheterocycle or thioheterocycle; and each of said aryl, aryloxy, arylthio, aryl-NR$^{10}$—, 5 or 6 membered heterocycle, oxyheterocycle or thioheterocycle is optionally substituted with one or more R$^{17}$; C$_{3-10}$ cycloalkyl, oxycycloalkyl or thiocycloalkyl; C$_{4-10}$ cycloalkenyl with the proviso that the double bond cannot be adjacent to a nitrogen; H with the proviso that if X is an alkylene, an alkenylene or an alkynylene, then X comprises at least 5 carbon atoms;
R$^4$ is independently selected from the group consisting of hydrogen C$_{1-18}$ alkyl; C$_{2-18}$ alkenyl; C$_{2-18}$ alkynyl; C$_{1-18}$ alkoxy; C$_{1-18}$ alkylthio; halogen; OH; CN; NO$_2$; NR$^7$R$^8$; OCF$_3$; haloalkyl; C(═O)R$^9$; C(═S)R$^9$; SH; aryl; aryloxy; arylthio; arylalkyl; C$_{1-18}$ hydroxyalkyl; C$_{3-10}$ cycloalkyl; C$_{3-10}$ cycloalkyloxy; C$_{3-10}$ cycloalkylthio; C$_{3-10}$ cycloalkenyl; C$_{3-10}$ cycloalkynyl; 5 or 6 membered heterocycle, oxyheterocycle or thioheterocycle; optionally R$^4$ is not —OH, —SH, ═O or ═S;
R$^5$ is independently absent or selected from the group consisting of hydrogen; C$_{1-18}$ alkyl; C$_{2-18}$ alkenyl; C$_{2-18}$ alkynyl; C$_{1-18}$ alkoxy; C$_{1-18}$ alkylthio; halogen; OH; CN; NO$_2$; NR$^7$R$^8$; OCF$_3$; haloalkyl; C(═O)R$^9$; C(═S)R$^9$; SH; aryl; aryloxy; arylthio; arylalkyl; C$_{1-18}$ hydroxyalkyl; C$_{3-10}$ cycloalkyl; C$_{3-10}$ cycloalkyloxy; C$_{3-10}$ cycloalkylthio C$_{3-10}$ cycloalkenyl; C$_{3-10}$ cycloalkynyl; 5 or 6 membered heterocycle, oxyheterocycle or thioheterocycle;
Each R$^6$ and R$^{17}$ is independently selected from the group consisting of hydrogen; C$_{1-18}$ alkyl; C$_{2-18}$ alkenyl; C$_{2-18}$ alkynyl; C$_{1-18}$ alkoxy; C$_{1-18}$ alkylthio; C$_{3-10}$ cycloalkyl, C$_{3-10}$ cycloalkenyl or C$_{3-10}$ cycloalkynyl; halogen; OH; CN; NO$_2$; NR$^7$R$^8$; OCF$_3$; haloalkyl; C(═O)R$^9$; C(═S) R$^9$; SH; aryl; aryloxy; arylthio; arylalkyl; arylalkyloxy (optionally a oxybenzyl); arylalkylthio (optionally a benzylthio); 5 or 6 membered heterocycle, oxyheterocycle or thioheterocycle; C$_{1-18}$ hydroxyalkyl; and each of said aryl, aryloxy, arylthio, arylalkyl, arylalkyloxy (optionally a oxybenzyl), arylalkylthio (optionally a benzylthio), 5 or 6 membered heterocycle, oxyheterocycle or thioheterocycle, C$_{1-18}$ hydroxyalkyl is optionally substituted with 1 or more R$^{19}$;
Each R$^7$ and R$^8$ is independently selected from the group consisting of H; C$_{1-18}$ alkyl; C$_{1-18}$ alkenyl; aryl; C$_{3-10}$ cycloalkyl; C$_{4-10}$ cycloalkenyl; 5-6 membered heterocycle; C(═O)R$^{12}$; C(═S)R$^{12}$; an amino acid residue linked through a carboxyl group thereof; alternatively, R$^7$ and R$^8$, together with the nitrogen to which they are attached, combine to form a 5-6 membered heterocycle;
Each R$^9$ and R$^{18}$ is independently selected from the group consisting of H; OH; C$_{1-18}$ alkyl; C$_{2-18}$ alkenyl; C$_{3-10}$ cycloalkyl; C$_{4-10}$ cycloalkenyl; C$_{1-18}$ alkoxy; NR$^{15}$R$^{16}$; aryl an amino acid residue linked through an amino group thereof;
Each R$^{10}$ and R$^{11}$ is independently selected from the group the group consisting of H; C$_{1-18}$ alkyl; C$_{1-18}$ alkenyl; C$_{3-10}$ cycloalkyl; C$_{4-10}$ cycloalkenyl; aryl; C(═O)R$^{12}$; 5-6 membered heterocycle; an amino acid residue linked through a carboxyl group thereof;
R$^{12}$ is independently selected from the group consisting of H; C$_{1-18}$ alkyl; C$_{2-18}$ alkenyl; aryl; C$_{3-10}$ cycloalkyl;

$C_{4-10}$ cycloalkenyl; an amino acid residue linked through an amino group thereof;

Each $R^{13}$ and $R^{14}$ is independently selected from the group consisting of H; $C_{1-18}$alkyl; $C_{2-18}$ alkenyl; aryl; $C_{3-10}$ cycloalkyl; $C_{4-10}$ cycloalkenyl; $C(=O)R^{12}$; $C(=S)R^{12}$; an amino acid residue linked through a carboxyl group thereof;

Each $R^{15}$ and $R^{16}$ is independently selected from the group consisting of H; $C_{1-18}$alkyl; $C_{2-18}$ alkenyl; $C_{2-18}$ alkynyl; aryl; $C_{3-10}$ cycloalkyl; $C_{4-10}$ cycloalkenyl; an amino acid residue linked through a carboxyl group thereof;

$R^{19}$ is independently selected from the group consisting of H; $C_{1-18}$ alkyl, preferably $C_{1-6}$ alkyl; $C_{2-18}$ alkenyl; $C_{2-18}$ alkynyl; $C_{1-18}$ alkoxy, preferably $C_{1-6}$ alkoxy; $C_{1-18}$ alkylthio; $C_{3-10}$ cycloalkyl; $C_{4-10}$ cycloalkenyl; $C_{4-10}$ cycloalkynyl; halogen; OH; CN; $NO_2$; $NR^{20}R^{21}$; $OCF_3$; haloalkyl; $C(=O)R^{22}$; $C(=S)R^{22}$; SH; $C(=O)N(C_{1-6}$ alkyl), $N(H)S(O)(O)(C_{1-6}$ alkyl); aryl; aryloxy; arylthio; arylalkyl; and each of said aryl, aryloxy, arylthio, arylalkyl substituted with 1 or more halogens, particularly a phenyl substituted with 1-2 halogens; hydroxyalkyl; 5 or 6 membered heterocycle, oxyheterocycle or thioheterocycle each unsubstituted or substituted with 1 or more halogens;

Each $R^{20}$ and $R^{21}$ is independently selected from the group consisting of H; $C_{1-18}$ alkyl, preferably $C_{1-6}$ alkyl; $C_{2-18}$ alkenyl; $C_{2-18}$ alkynyl; aryl; $C_{3-10}$ cycloalkyl; $C_{4-10}$ cycloalkenyl; $C(=O)R^{12}$, $C(=S)R^{12}$;

$R^{22}$ is independently selected from H; OH; $C_{1-18}$alkyl; $C_{2-18}$alkenyl; $C_{1-18}$ alkoxy; $NR^{23}R^{24}$; aryl; $C_{3-10}$ cycloalkyl; $C_{4-10}$ cycloalkenyl;

Each $R^{23}$ and $R^{24}$ is independently selected from the group the group consisting of H; $C_{1-18}$ alkyl, preferably $C_{2-3}$ alkyl, wherein $C_{2-3}$ alkyl taken together with N of $R^{22}$ can form a saturated heterocycle, which heterocycle is optionally substituted with OH or aryl or an amino acid residue;

Z is selected from (=O), (=S), and (=$NR^{27}$);

$R^{25}$ is selected from the group consisting of of H, $C_{1-18}$ alkyl, preferably $C_{1-4}$ alkyl; $C_{3-10}$cycloalkyl, such as $C_{5-10}$bicycloalkyl; $C_{3-10}$cycloalkenyl; $(C_{3-8}$cycloalkyl)-$C_{1-3}$alkyl; aryl, such as phenyl; 5 or 6 membered heterocycle, such as pyridyl; alkylaryl, such as benzyl; and each of said $C_{1-18}$ alkyl, preferably $C_{1-4}$ alkyl, $C_{3-10}$ cycloalkyl, $C_{3-10}$ cycloalkenyl, $(C_{3-8}$ cycloalkyl)-$C_{1-3}$ alkyl, $C_{5-10}$bicycloalkyl, adamantyl, phenyl, pyridyl and benzyl is optionally substituted with 1-4 of each of $C_{1-6}$ alkyl, $C_{1-6}$ alkoxy, halo, $CH_2OH$, oxybenzyl, and OH; and heterocycle having 3 to 7 carbon atoms, preferably a saturated heterocycle wherein the heteroatoms are S, S(O), or $S(O)_2$ separated from the imidazopyridyl ring nitrogen atom by at least 2 heterocycle carbon atoms; and $R^{27}$ is selected from the group consisting of H, $C_{1-18}$ alkyl, $C_{3-10}$ cycloalkyl, $(C_{3-10}$cycloalkyl)-$C_{1-6}$ alkyl; aryl; arylalkyl, such as benzyl.

An embodiment of the present invention in its ninth aspect relates to compounds of the formula (A3), pharmaceutically acceptable compositions, salts, tautomers, polymorphs and isomers thereof and their use in a treatment of viral infection or to manufacture a medicament to treat viral infection

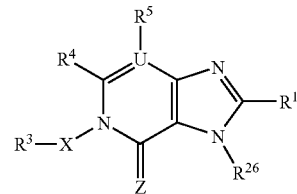

(A3)

wherein

U is N;

$R^1$ is selected from hydrogen; aryl unsubstituted or substituted with one or more $R^6$, heterocycle unsubstituted or substituted with one or more $R^6$, $C_{3-10}$ cycloalkyl unsubstituted or substituted with one or more $R^6$ and $C_{4-10}$ cycloalkenyl unsubstituted or substituted with one or more $R^6$;

X is selected from the group consisting of a divalent, saturated or unsaturated, substituted or unsubstituted $C_1$-$C_{10}$ hydrocarbon group optionally including one or more heteroatoms in the main chain (provided that the heteroatom is not linked to N of the nucleus), said heteroatoms being selected from the group consisting of O, S, and N; such as $C_{1-6}$ alkylene, (for example —$CH_2$—, —$CH(CH_3)$—, —$CH_2$—$CH_2$—, —$CH_2$—$CH_2$—$CH_2$—, —$CH_2$—$CH_2$—$CH_2$—$CH_2$), —$(CH_2)_{2-4}$—O—$(CH_2)_{2-4}$—, —$(CH_2)_{2-4}$—S—$(CH_2)_{2-4}$—, —$(CH_2)_{2-4}$—$NR^{10}$—$(CH_2)_{2-4}$—, $C_{3-10}$ cycloalkylidene, $C_{2-6}$ alkenylene (such as —CH=CH—$CH_2$—), $C_{2-6}$ alkynylene;

$R^3$ is selected from the group consisting of aryl; aryloxy; arylthio; aryl-$NR^{10}$—; 5 or 6 membered heterocycle, oxyheterocycle or thioheterocycle; and each of said aryl, aryloxy, arylthio, aryl-$NR^{10}$—, 5 or 6 membered heterocycle, oxyheterocycle or thioheterocycle is optionally substituted with one or more $R^{17}$; $C_{3-10}$ cycloalkyl, oxycycloalkyl or thiocycloalkyl; $C_{4-10}$ cycloalkenyl with the proviso that the double bond cannot be adjacent to a nitrogen; H with the proviso that if X is an alkylene, an alkenylene or an alkynylene, then X comprises at least 5 carbon atoms;

$R^4$ is independently selected from the group consisting of hydrogen $C_{1-18}$ alkyl; $C_{2-18}$ alkenyl; $C_{2-18}$ alkynyl; $C_{1-18}$ alkoxy; $C_{1-18}$ alkylthio; halogen; OH; CN; $NO_2$; $NR^7R^8$; $OCF_3$; haloalkyl; $C(=O)R^9$; $C(=S)R^9$; SH; aryl; aryloxy; arylthio; arylalkyl; $C_{1-18}$ hydroxyalkyl; $C_{3-10}$ cycloalkyl; $C_{3-10}$ cycloalkyloxy; $C_{3-10}$ cycloalkylthio; $C_{3-10}$ cycloalkenyl; $C_{3-10}$ cycloalkynyl; 5 or 6 membered heterocycle, oxyheterocycle or thioheterocycle; optionally, $R^4$ is not OH, SH, thio or oxo;

$R^5$ is independently absent or selected from the group consisting of hydrogen; $C_{1-18}$ alkyl; $C_{2-18}$ alkenyl; $C_{2-18}$ alkynyl; $C_{1-18}$ alkoxy; $C_{1-18}$ alkylthio; halogen; OH; CN; $NO_2$; $NR^7R^8$; $OCF_3$; haloalkyl; $C(=O)R^9$; $C(=S)R^9$; SH; aryl; aryloxy; arylthio; arylalkyl; $C_{1-18}$ hydroxyalkyl; $C_{3-10}$ cycloalkyl; $C_{3-10}$ cycloalkyloxy; $C_{3-10}$ cycloalkylthio $C_{3-10}$ cycloalkenyl; $C_{3-10}$ cycloalkynyl; 5 or 6 membered heterocycle, oxyheterocycle or thioheterocycle;

Each $R^6$ and $R^{17}$ is independently selected from the group consisting of hydrogen; $C_{1-18}$ alkyl; $C_{2-18}$ alkenyl; $C_{2-18}$ alkynyl; $C_{1-18}$ alkoxy; $C_{1-18}$ alkylthio; $C_{3-10}$ cycloalkyl, $C_{3-10}$ cycloalkenyl or $C_{3-10}$ cycloalkynyl; halogen; OH; CN; $NO_2$; $NR^7R^8$; $OCF_3$; haloalkyl; $C(=O)R^9$; C(=S)

$R^9$; SH; aryl; aryloxy; arylthio; arylalkyl; arylalkyloxy (optionally a oxybenzyl); arylalkylthio (optionally a benzylthio); 5 or 6 membered heterocycle, oxyheterocycle or thioheterocycle; $C_{1-18}$ hydroxyalkyl; and each of said aryl, aryloxy, arylthio, arylalkyl, arylalkyloxy (optionally a oxybenzyl), arylalkylthio (optionally a benzylthio), 5 or 6 membered heterocycle, oxyheterocycle or thioheterocycle, $C_{1-18}$ hydroxyalkyl is optionally substituted with 1 or more $R^{19}$;

Each $R^7$ and $R^8$ is independently selected from the group consisting of H; $C_{1-18}$ alkyl; $C_{1-18}$ alkenyl; aryl; $C_{3-10}$ cycloalkyl; $C_{4-10}$ cycloalkenyl; 5-6 membered heterocycle; $C(=O)R^{12}$; $C(=S)R^{12}$; an amino acid residue linked through a carboxyl group thereof; alternatively, $R^7$ and $R^8$, together with the nitrogen to which they are attached, combine to form a 5-6 membered heterocycle;

Each $R^9$ and $R^{18}$ is independently selected from the group consisting of H; OH; $C_{1-18}$ alkyl; $C_{2-18}$ alkenyl; $C_{3-10}$ cycloalkyl; $C_{4-10}$ cycloalkenyl; $C_{1-18}$ alkoxy; $NR^{15}R^{16}$; aryl an amino acid residue linked through an amino group thereof;

Each $R^{10}$ and $R^{11}$ is independently selected from the group the group consisting of H; $C_{1-18}$ alkyl; $C_{1-18}$ alkenyl; $C_{3-10}$ cycloalkyl; $C_{4-10}$ cycloalkenyl; aryl; $C(=O)R^{12}$; 5-6 membered heterocycle; an amino acid residue linked through a carboxyl group thereof;

$R^{12}$ is independently selected from the group consisting of H; $C_{1-18}$ alkyl $C_{2-18}$ alkenyl; aryl; $C_{3-10}$ cycloalkyl; $C_{4-10}$ cycloalkenyl; an amino acid residue linked through an amino group thereof;

Each $R^{15}$ and $R^{16}$ is independently selected from the group consisting of H; $C_{1-18}$ alkyl; $C_{2-18}$ alkenyl; $C_{2-18}$ alkynyl; aryl; $C_{3-10}$ cycloalkyl; $C_{4-10}$ cycloalkenyl; an amino acid residue linked through a carboxyl group thereof;

$R^{19}$ is independently selected from the group consisting of H; $C_{1-18}$alkyl, preferably $C_{1-6}$ alkyl; $C_{2-18}$ alkenyl; $C_{2-18}$ alkynyl; $C_{1-18}$ alkoxy, preferably $C_{1-6}$ alkoxy; $C_{1-18}$ alkylthio; $C_{3-10}$ cycloalkyl; $C_{4-10}$ cycloalkenyl; $C_{4-10}$ cycloalkynyl; halogen; OH; CN; $NO_2$; $NR^{20}R^{21}$; $OCF_3$; haloalkyl; $C(=O)R^{22}$; $C(=S)R^{22}$; SH; $C(=O)N(C_{1-6}$ alkyl), $N(H)S(O)(O)(C_{1-6}$ alkyl); aryl; aryloxy; arylthio; arylalkyl; and each of said aryl, aryloxy, arylthio, arylalkyl substituted with 1 or more halogens, particularly a phenyl substituted with 1-2 halogens; hydroxyalkyl; 5 or 6 membered heterocycle, oxyheterocycle or thioheterocycle each unsubstituted or substituted with 1 or more halogens;

Each $R^{20}$ and $R^{21}$ is independently selected from the group consisting of H; $C_{1-18}$ alkyl, preferably $C_{1-6}$ alkyl; $C_{2-18}$ alkenyl; $C_{2-18}$ alkynyl; aryl; $C_{3-10}$ cycloalkyl; $C_{4-10}$ cycloalkenyl; $C(=O)R^{12}$, $C(=S)R^{12}$;

$R^{22}$ is independently selected from H; OH; $C_{1-18}$alkyl; $C_{2-18}$alkenyl; $C_{1-18}$ alkoxy; $NR^{23}R^{24}$; aryl; $C_{3-10}$ cycloalkyl; $C_{4-10}$ cycloalkenyl;

Each $R^{23}$ and $R^{24}$ is independently selected from the group the group consisting of H; $C_{1-18}$ alkyl, preferably $C_{2-3}$ alkyl, wherein $C_{2-3}$ alkyl taken together with N of $R^{22}$ can form a saturated heterocycle, which heterocycle is optionally substituted with OH or aryl or an amino acid residue;

Z is selected from (=O), (=S), and (=$NR^{27}$);

$R^{26}$ is selected from the group consisting of of H, $C_{1-18}$ alkyl, preferably $C_{1-4}$ alkyl; $C_{3-10}$cycloalkyl, such as $C_{5-10}$bicycloalkyl; $C_{3-10}$cycloalkenyl; $(C_{3-8}$cycloalkyl)-$C_{1-3}$alkyl; aryl, such as phenyl; 5 or 6 membered heterocycle, such as pyridyl; alkylaryl, such as benzyl; and each of said $C_{1-18}$ alkyl, preferably $C_{1-4}$ alkyl, $C_{3-10}$ cycloalkyl, $C_{3-10}$cycloalkenyl, $(C_{3-8}$ cycloalkyl)-$C_{1-3}$ alkyl, $C_{5-10}$bicycloalkyl, adamantyl, phenyl, pyridyl and benzyl is optionally substituted with 1-4 of each of $C_{1-6}$ alkyl, $C_{1-6}$ alkoxy, halo, $CH_2OH$, oxybenzyl, and OH; and heterocycle having 3 to 7 carbon atoms, preferably a saturated heterocycle wherein the heteroatoms are S, S(O), or $S(O)_2$ separated from the imidazopyridyl ring nitrogen atom by at least 2 heterocycle carbon atoms; and $R^{27}$ is selected from the group consisting of H, $C_{1-18}$ alkyl, $C_{3-10}$ cycloalkyl, $(C_{3-10}$cycloalkyl)-$C_{1-6}$alkyl; aryl; arylalkyl, such as benzyl.

An embodiment of the present invention in its tenth aspect relates to compounds of the formula (A2), pharmaceutically acceptable compositions, salts, tautomers, polymorphs and isomers thereof and their use in a treatment of viral infection or to manufacture a medicament to treat viral infection

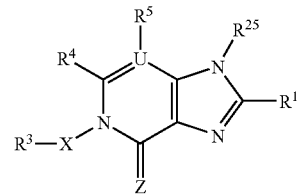

(A2)

wherein

U is N;

$R^1$ is selected from hydrogen; aryl unsubstituted or substituted with one or more $R^6$, heterocycle unsubstituted or substituted with one or more $R^6$, $C_{3-10}$ cycloalkyl unsubstituted or substituted with one or more $R^6$ and $C_{4-10}$ cycloalkenyl unsubstituted or substituted with one or more $R^6$;

X is selected from the group consisting of a divalent, saturated or unsaturated, substituted or unsubstituted $C_1$-$C_{10}$ hydrocarbon group optionally including one or more heteroatoms in the main chain (provided that the heteroatom is not linked to N of the nucleus), said heteroatoms being selected from the group consisting of O, S, and N; such as $C_{1-6}$ alkylene, (for example —$CH_2$—, —$CH(CH_3)$—, —$CH_2$—$CH_2$—, —$CH_2$—$CH_2$—$CH_2$—, —$CH_2$—$CH_2$—$CH_2$—$CH_2$—), —$(CH_2)_{2-4}$—O—$(CH_2)_{2-4}$—, —$(CH_2)_{2-4}$—S—$(CH_2)_{2-4}$—, —$(CH_2)_{2-4}$—$NR^{10}$—$(CH_2)_{2-4}$—, $C_{3-10}$ cycloalkylidene, $C_{2-6}$ alkenylene (such as —CH=CH—$CH_2$—), $C_{2-6}$ alkynylene;

$R^2$ is selected from the group consisting of hydrogen $C_{1-18}$ alkyl; $C_{2-18}$ alkenyl; $C_{2-18}$ alkynyl; $C_{1-18}$ alkoxy; $C_{1-18}$ alkylthio; halogen; OH; CN; $NO_2$; $NR^7R^8$; $OCF_3$; haloalkyl; $C(=O)R^9$; $C(=S)R^9$; SH; aryl; aryloxy; arylthio; arylalkyl; $C_{1-18}$ hydroxyalkyl; $C_{3-10}$ cycloalkyl; $C_{3-10}$ cycloalkyloxy; $C_{3-10}$ cycloalkylthio; $C_{3-10}$ cycloalkenyl; $C_{3-10}$ cycloalkynyl; 5 or 6 membered heterocycle, oxyheterocycle or thioheterocycle;

$R^3$ is selected from the group consisting of aryl; aryloxy; arylthio; aryl-$NR^{10}$—; 5 or 6 membered heterocycle, oxyheterocycle or thioheterocycle; and each of said aryl, aryloxy, arylthio, aryl-$NR^{10}$—, 5 or 6 membered heterocycle, oxyheterocycle or thioheterocycle is optionally substituted with one or more $R^{17}$; $C_{3-10}$ cycloalkyl, oxycycloalkyl or thiocycloalkyl; $C_{4-10}$ cycloalkenyl with the proviso that the double bond cannot be adjacent to a nitrogen; H with the proviso that if X is an alkylene, an alkenylene or an alkynylene, then X comprises at least 5 carbon atoms;

$R^5$ is independently absent or selected from the group consisting of hydrogen; $C_{1-18}$ alkyl; $C_{2-18}$ alkenyl; $C_{2-18}$ alkynyl; $C_{1-18}$ alkoxy; $C_{1-18}$ alkylthio; halogen; OH; CN; $NO_2$; $NR^7R^8$; $OCF_3$; haloalkyl; $C(=O)R^9$; $C(=S)R^9$; SH; aryl; aryloxy; arylthio; arylalkyl; $C_{1-18}$ hydroxyalkyl; $C_{3-10}$ cycloalkyl; $C_{3-10}$ cycloalkyloxy; $C_{3-10}$ cycloalkylthio $C_{3-10}$ cycloalkenyl; $C_{3-10}$ cycloalkynyl; 5 or 6 membered heterocycle, oxyheterocycle or thioheterocycle;

Each $R^6$ and $R^{17}$ is independently selected from the group consisting of hydrogen; $C_{1-18}$ alkyl; $C_{2-18}$ alkenyl; $C_{2-18}$ alkynyl; $C_{1-18}$ alkoxy; $C_{1-18}$ alkylthio; $C_{3-10}$ cycloalkyl, $C_{3-10}$ cycloalkenyl or $C_{3-10}$ cycloalkynyl; halogen; OH; CN; $NO_2$; $NR^7R^8$; $OCF_3$; haloalkyl; $C(=O)R^9$; $C(=S)R^9$; SH; aryl; aryloxy; arylthio; arylalkyl; arylalkyloxy (optionally a oxybenzyl); arylalkylthio (optionally a benzylthio); 5 or 6 membered heterocycle, oxyheterocycle or thioheterocycle; $C_{1-18}$ hydroxyalkyl; and each of said aryl, aryloxy, arylthio, arylalkyl, arylalkyloxy (optionally a oxybenzyl), arylalkylthio (optionally a benzylthio), 5 or 6 membered heterocycle, oxyheterocycle or thioheterocycle, $C_{1-18}$ hydroxyalkyl is optionally substituted with 1 or more $R^{19}$;

Each $R^7$ and $R^8$ is independently selected from the group consisting of H; $C_{1-18}$ alkyl; $C_{1-18}$ alkenyl; aryl; $C_{3-10}$ cycloalkyl; $C_{4-10}$ cycloalkenyl; 5-6 membered heterocycle; $C(=O)R^{12}$; $C(=S)R^{12}$; an amino acid residue linked through a carboxyl group thereof; alternatively, $R^7$ and $R^8$, together with the nitrogen to which they are attached, combine to form a 5-6 membered heterocycle;

Each $R^9$ and $R^{18}$ is independently selected from the group consisting of H; OH; $C_{1-18}$ alkyl; $C_{2-18}$ alkenyl; $C_{3-10}$ cycloalkyl; $C_{4-10}$ cycloalkenyl; $C_{1-18}$ alkoxy; $NR^{15}R^{16}$; aryl an amino acid residue linked through an amino group thereof;

Each $R^{10}$ and $R^{11}$ is independently selected from the group the group consisting of H; $C_{1-18}$ alkyl; $C_{1-18}$ alkenyl; $C_{3-10}$ cycloalkyl; $C_{4-10}$ cycloalkenyl; aryl; $C(=O)R^{12}$; 5-6 membered heterocycle; an amino acid residue linked through a carboxyl group thereof;

$R^{12}$ is independently selected from the group consisting of H; $C_{1-18}$ alkyl; $C_{2-18}$ alkenyl; aryl; $C_{3-10}$ cycloalkyl; $C_{4-10}$ cycloalkenyl; an amino acid residue linked through an amino group thereof;

Each $R^{15}$ and $R^{16}$ is independently selected from the group consisting of H; $C_{1-18}$ alkyl; $C_{2-18}$ alkenyl; $C_{2-18}$ alkynyl; aryl; $C_{3-10}$ cycloalkyl; $C_{4-10}$ cycloalkenyl; an amino acid residue linked through a carboxyl group thereof;

$R^{19}$ is independently selected from the group consisting of H; $C_{1-18}$ alkyl, preferably $C_{1-6}$alkyl; $C_{2-18}$ alkenyl; $C_{2-18}$ alkynyl; $C_{1-18}$alkoxy, preferably $C_{1-6}$alkoxy; $C_{1-18}$ alkylthio; $C_{3-10}$ cycloalkyl; $C_{4-10}$ cycloalkenyl; $C_{4-10}$ cycloalkynyl; halogen; OH; CN; $NO_2$; $NR^{20}R^{21}$; $OCF_3$; haloalkyl; $C(=O)R^{22}$; $C(=S)R^{22}$; SH; $C(=O)N(C_{1-6}$ alkyl), $N(H)S(O)(O)(C_{1-6}$ alkyl); aryl; aryloxy; arylthio; arylalkyl; and each of said aryl, aryloxy, arylthio, arylalkyl substituted with 1 or more halogens, particularly a phenyl substituted with 1-2 halogens; hydroxyalkyl; 5 or 6 membered heterocycle, oxyheterocycle or thioheterocycle each unsubstituted or substituted with 1 or more halogens;

Each $R^{20}$ and $R^{21}$ is independently selected from the group consisting of H; $C_{1-18}$ alkyl, preferably $C_{1-6}$ alkyl; $C_{2-18}$ alkenyl; $C_{2-18}$ alkynyl; aryl; $C_{3-10}$ cycloalkyl; $C_{4-10}$ cycloalkenyl; $C(=O)R^{12}$, $C(=S)R^{12}$;

$R^{22}$ is independently selected from H; OH; $C_{1-18}$alkyl; $C_{2-18}$alkenyl; $C_{1-18}$ alkoxy; $NR^{23}R^{24}$; aryl; $C_{3-10}$ cycloalkyl; $C_{4-10}$ cycloalkenyl;

Each $R^{23}$ and $R^{24}$ is independently selected from the group the group consisting of H; $C_{1-18}$ alkyl, preferably $C_{2-3}$ alkyl, wherein $C_{2-3}$ alkyl taken together with N of $R^{22}$ can form a saturated heterocycle, which heterocycle is optionally substituted with OH or aryl or an amino acid residue;

Z is selected from (=O), (=S), and (=$NR^{27}$);

$R^{25}$ is selected from the group consisting of of H, $C_{1-18}$ alkyl, preferably $C_{1-4}$ alkyl; $C_{3-10}$cycloalkyl, such as $C_{5-10}$bicycloalkyl; $C_{3-10}$cycloalkenyl; ($C_{3-8}$cycloalkyl)-$C_{1-3}$alkyl; aryl, such as phenyl; 5 or 6 membered heterocycle, such as pyridyl; alkylaryl, such as benzyl; and each of said $C_{1-18}$ alkyl, preferably $C_{1-4}$ alkyl, $C_{3-10}$-cycloalkyl, $C_{3-10}$ cycloalkenyl, ($C_{3-8}$cycloalkyl)-$C_{1-3}$ alkyl, $C_{5-10}$bicycloalkyl, adamantyl, phenyl, pyridyl and benzyl is optionally substituted with 1-4 of each of $C_{1-6}$ alkyl, $C_{1-6}$ alkoxy, halo, $CH_2OH$, oxybenzyl, and OH; and heterocycle having 3 to 7 carbon atoms, preferably a saturated heterocycle wherein the heteroatoms are S, S(O), or $S(O)_2$ separated from the imidazopyridyl ring nitrogen atom by at least 2 heterocycle carbon atoms; and $R^{27}$ is selected from the group consisting of H, $C_{1-18}$ alkyl, $C_{3-10}$ cycloalkyl, ($C_{3-10}$cycloalkyl)-$C_{1-6}$alkyl; aryl; arylalkyl, such as benzyl;

An embodiment of the present invention in its eleventh aspect relates to compounds of the formula (A3), pharmaceutically acceptable compositions, salts, tautomers, polymorphs and isomers thereof and their use in a treatment of viral infection or to manufacture a medicament to treat viral infection

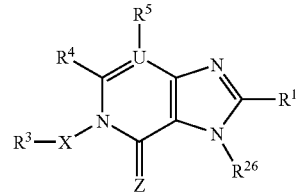

(A3)

wherein:

U is N;

$R^1$ is selected from hydrogen; aryl unsubstituted or substituted with one or more $R^6$, heterocycle unsubstituted or substituted with one or more $R^6$, $C_{3-10}$ cycloalkyl unsubstituted or substituted with one or more $R^6$ and $C_{4-10}$ cycloalkenyl unsubstituted or substituted with one or more $R^6$;

X is selected from the group consisting of a divalent, saturated or unsaturated, substituted or unsubstituted $C_1$-$C_{10}$ hydrocarbon group optionally including one or more heteroatoms in the main chain (provided that the heteroatom is not linked to N of the nucleus), said heteroatoms being selected from the group consisting of O, S, and N; such as $C_{1-6}$ alkylene, (for example —$H_2$—, —$CH(CH_3)$—, —$CH_2$—$CH_2$—, —$CH_2$—$CH_2$—$CH_2$—, —$CH_2$—$CH_2$—$CH_2$—$CH_2$), —$(CH_2)_{2-4}$—O—$(CH_2)_{2-4}$—, —$(CH_2)_{2-4}$—S—$(CH_2)_{2-4}$—, —(CH$_2$)$_{2-4}$—NR$^{10}$—(CH$_2$)$_{2-4}$—, C$_{3-10}$ cycloalkylidene, C$_{2-6}$ alkenylene (such as —CH=CH—CH$_2$—), C$_{2-6}$ alkynylene;

R$^2$ is independently selected from the group consisting of hydrogen C$_{1-18}$ alkyl; C$_{2-18}$ alkenyl; C$_{2-18}$ alkynyl; C$_{1-18}$ alkoxy; C$_{1-18}$ alkylthio; halogen; OH; CN; NO$_2$; NR$^7$R$^8$; OCF$_3$; haloalkyl; C(=O)R$^9$; C(=S)R$^9$; SH; aryl; aryloxy; arylthio; arylalkyl; C$_{1-18}$ hydroxyalkyl; C$_{3-10}$ cycloalkyl; C$_{3-10}$ cycloalkyloxy; C$_{3-10}$ cycloalkylthio; C$_{3-10}$ cycloalkenyl; C$_{3-10}$ cycloalkynyl; 5 or 6 membered heterocycle, oxyheterocycle or thioheterocycle;

R$^3$ is selected from the group consisting of aryl; aryloxy; arylthio; aryl-NR$^{10}$—; 5 or 6 membered heterocycle, oxyheterocycle or thioheterocycle; and each of said aryl, aryloxy, arylthio, aryl-NR$^{10}$—, 5 or 6 membered heterocycle, oxyheterocycle or thioheterocycle is optionally substituted with one or more R$^{17}$; C$_{3-10}$ cycloalkyl, oxycycloalkyl or thiocycloalkyl; C$_{4-10}$ cycloalkenyl with the proviso that the double bond cannot be adjacent to a nitrogen; H with the proviso that if X is an alkylene, an alkenylene or an alkynylene, then X comprises at least 5 carbon atoms;

R$^5$ is independently absent or selected from the group consisting of hydrogen; C$_{1-18}$ alkyl; C$_{2-18}$ alkenyl; C$_{2-18}$ alkynyl; C$_{1-18}$ alkoxy; C$_{1-18}$ alkylthio; halogen; OH; CN; NO$_2$; NR$^7$R$^8$; OCF$_3$; haloalkyl; C(=O)R$^9$; C(=S)R$^9$; SH; aryl; aryloxy; arylthio; arylalkyl; C$_{1-18}$ hydroxyalkyl; C$_{3-10}$ cycloalkyl; C$_{3-10}$ cycloalkyloxy; C$_{3-10}$ cycloalkylthio C$_{3-10}$ cycloalkenyl; C$_{3-10}$ cycloalkynyl; 5 or 6 membered heterocycle, oxyheterocycle or thioheterocycle;

Each R$^6$ and R$^{17}$ is independently selected from the group consisting of hydrogen; C$_{1-18}$ alkyl; C$_{2-18}$ alkenyl; C$_{2-18}$ alkynyl; C$_{1-18}$ alkoxy; C$_{1-18}$ alkylthio; C$_{3-10}$ cycloalkyl, C$_{3-10}$ cycloalkenyl or C$_{3-10}$ cycloalkynyl; halogen; OH; CN; NO$_2$; NR$^7$R$^8$; OCF$_3$; haloalkyl; C(=O)R$^9$; C(=S)R$^9$; SH; aryl; aryloxy; arylthio; arylalkyl; arylalkyloxy (optionally a oxybenzyl); arylalkylthio (optionally a benzylthio); 5 or 6 membered heterocycle, oxyheterocycle or thioheterocycle; C$_{1-18}$ hydroxyalkyl; and each of said aryl, aryloxy, arylthio, arylalkyl, arylalkyloxy (optionally a oxybenzyl), arylalkylthio (optionally a benzylthio), 5 or 6 membered heterocycle, oxyheterocycle or thioheterocycle, C$_{1-18}$ hydroxyalkyl is optionally substituted with 1 or more R$^{19}$;

Each R$^7$ and R$^8$ is independently selected from the group consisting of H; C$_{1-18}$ alkyl; C$_{1-18}$alkenyl; aryl; C$_{3-10}$ cycloalkyl; C$_{4-10}$ cycloalkenyl; 5-6 membered heterocycle; C(=O)R$^{12}$; C(=S)R$^{12}$; an amino acid residue linked through a carboxyl group thereof; alternatively, R$^7$ and R$^8$, together with the nitrogen to which they are attached, combine to form a 5-6 membered heterocycle;

Each R$^9$ and R$^{18}$ is independently selected from the group consisting of H; OH; C$_{1-18}$ alkyl; C$_{2-18}$ alkenyl; C$_{3-10}$ cycloalkyl; C$_{4-10}$ cycloalkenyl; C$_{1-18}$ alkoxy; NR$^{15}$R$^{16}$; aryl an amino acid residue linked through an amino group thereof;

Each R$^{10}$ and R$^{11}$ is independently selected from the group the group consisting of H; C$_{1-18}$ alkyl; C$_{1-18}$ alkenyl; C$_{3-10}$ cycloalkyl; C$_{4-10}$ cycloalkenyl; aryl; C(=O)R$^{12}$; 5-6 membered heterocycle; an amino acid residue linked through a carboxyl group thereof;

R$^{12}$ is independently selected from the group consisting of H; C$_{1-18}$ alkyl; C$_{2-18}$ alkenyl; aryl; C$_{3-10}$ cycloalkyl; C$_{4-10}$ cycloalkenyl; an amino acid residue linked through an amino group thereof;

Each R$^{15}$ and R$^{16}$ is independently selected from the group consisting of H; C$_{1-18}$ alkyl; C$_{2-18}$ alkenyl; C$_{2-18}$ alkynyl; aryl; C$_{3-10}$ cycloalkyl; C$_{4-10}$ cycloalkenyl; an amino acid residue linked through a carboxyl group thereof;

R$^{19}$ is independently selected from the group consisting of H; C$_{1-18}$alkyl, preferably C$_{1-6}$alkyl; C$_{2-18}$ alkenyl; C$_{2-18}$ alkynyl; C$_{1-18}$alkoxy, preferably C$_{1-6}$alkoxy; C$_{1-18}$ alkylthio; C$_{3-10}$ cycloalkyl; C$_{4-10}$ cycloalkenyl; C$_{4-10}$ cycloalkynyl; halogen; OH; CN; NO$_2$; NR$^{20}$R$^{21}$; OCF$_3$; haloalkyl; C(=O)R$^{22}$; C(=S)R$^{22}$; SH; C(=O)N(C$_{1-6}$ alkyl), N(H)S(O)(O)(C$_{1-6}$ alkyl); aryl; aryloxy; arylthio; arylalkyl; and each of said aryl, aryloxy, arylthio, arylalkyl substituted with 1 or more halogens, particularly a phenyl substituted with 1-2 halogens; hydroxyalkyl; 5 or 6 membered heterocycle, oxyheterocycle or thioheterocycle each unsubstituted or substituted with 1 or more halogens;

Each R$^{20}$ and R$^{21}$ is independently selected from the group consisting of H; C$_{1-18}$alkyl, preferably C$_{1-6}$alkyl; C$_{2-18}$ alkenyl; C$_{2-18}$ alkynyl; aryl; C$_{3-10}$ cycloalkyl; C$_{4-10}$ cycloalkenyl; C(=O)R$^{12}$, C(=S)R$^{12}$;

R$^{22}$ is independently selected from H; OH; C$_{1-18}$ alkyl; C$_{2-18}$ alkenyl; C$_{1-18}$ alkoxy; NR$^{23}$R$^{24}$; aryl; C$_{3-10}$ cycloalkyl; C$_{4-10}$ cycloalkenyl;

Each R$^{23}$ and R$^{24}$ is independently selected from the group the group consisting of H; C$_{1-18}$ alkyl, preferably C$_{2-3}$ alkyl, wherein C$_{2-3}$ alkyl taken together with N of R$^{22}$ can form a saturated heterocycle, which heterocycle is optionally substituted with OH or aryl or an amino acid residue;

Z is selected from (=O), (=S), and (=NR$^{27}$);

R$^{26}$ is selected from the group consisting of of H, C$_{1-18}$ alkyl, preferably C$_{1-4}$ alkyl; C$_{3-10}$cycloalkyl, such as C$_{5-10}$bicycloalkyl; C$_{3-10}$cycloalkenyl; (C$_{3-8}$cycloalkyl)-C$_{1-3}$alkyl; aryl, such as phenyl; 5 or 6 membered heterocycle, such as pyridyl; alkylaryl, such as benzyl; and each of said C$_{1-18}$ alkyl, preferably C$_{1-4}$ alkyl, C$_{3-10}$ cycloalkyl, C$_{3-10}$cycloalkenyl, (C$_{3-8}$ cycloalkyl)-C$_{1-3}$ alkyl, C$_{5-10}$bicycloalkyl, adamantyl, phenyl, pyridyl and benzyl is optionally substituted with 1-4 of each of C$_{1-6}$ alkyl, C$_{1-6}$ alkoxy, halo, CH$_2$OH, oxybenzyl, and OH; and heterocycle having 3 to 7 carbon atoms, preferably a saturated heterocycle wherein the heteroatoms are S, S(O), or S(O)$_2$ separated from the imidazopyridyl ring nitrogen atom by at least 2 heterocycle carbon atoms; and R$^{27}$ is selected from the group consisting of H, C$_{1-18}$ alkyl, C$_{3-10}$ cycloalkyl, (C$_{3-10}$cycloalkyl)-C$_{1-6}$ alkyl; aryl; arylalkyl, such as benzyl.

An embodiment of this invention in its twelfth aspect relates to compounds of the general formula (B), pharmaceutically acceptable compositions, and the antiviral use thereof.

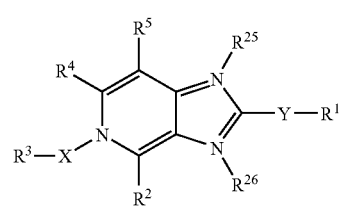

(B)

wherein:
  $R^1$ is selected from aryl, heterocycle, $C_{3-10}$ cycloalkyl, $C_{4-10}$ cycloalkenyl, and $C_{4-10}$ cycloalkynyl, wherein each are optionally substituted with 1 or 2 $R^6$;
  Y is a bond;
  $R^2$ and $R^4$ are independently selected from hydrogen, $C_{1-18}$ alkyl, $C_{2-18}$ alkenyl, $C_{2-18}$ alkynyl, $C_{1-18}$ alkoxy, $C_{1-18}$ alkylthio, halogen, —OH, —CN, —NO$_2$, —NR$^7$R$^8$, haloalkyloxy, haloalkyl, —C(=O)R$^9$, —C(=S)R$^9$, SH, aryl, aryloxy, arylthio, arylalkyl, $C_{1-18}$ hydroxyalkyl, $C_{3-10}$ cycloalkyl, $C_{3-10}$ cycloalkyloxy, $C_{3-10}$ cycloalkylthio, $C_{3-10}$ cycloalkenyl, $C_{7-10}$ cycloalkynyl, or heterocycle, provided that when one of $R^{25}$ or $R^{26}$ is present, then either $R^2$ or $R^4$ is selected from (=O), (=S), and =NR$^{27}$; provided that $R^2$ is not OH, SH, thio or oxo;
  X is selected from $C_1$-$C_3$ alkylene, $C_{2-3}$ alkenylene or $C_{2-3}$ alkynylene;
  $R^3$ is selected from aryl, aryloxy, arylthio, cycloalkyl, cycloalkenyl, cycloalkynyl, aryl-N($R^{10}$)—, or heterocycle, where each is optionally substituted with at least one $R^{17}$, provided that for cycloalkenyl the double bond is not adjacent to a nitrogen;
  R5 indpendently is absent or is selected from hydrogen, $C_{1-18}$ alkyl, $C_{2-18}$ alkenyl, $C_{2-18}$ alkynyl, $C_{1-18}$ alkoxy, $C_{1-18}$ alkylthio, halogen, —OH, —CN, —NO$_2$, —NR$^7$R$^8$, haloalkyloxy, haloalkyl, —C(=O)R$^9$, —C(=O)OR$^9$, —C(=S)R$^9$, SH, aryl, aryloxy, arylthio, arylalkyl, $C_{1-18}$ hydroxyalkyl, $C_{3-10}$ cycloalkyl, $C_{3-10}$ cycloalkyloxy, $C_{3-10}$ cycloalkylthio, $C_{3-10}$ cycloalkenyl, $C_{7-10}$ cycloalkynyl, or heterocycle;
  $R^6$ is selected from hydrogen, $C_{1-18}$ alkyl, $C_{2-18}$ alkenyl, $C_{2-18}$ alkynyl, $C_{1-18}$ alkoxy, $C_{1-18}$ alkylthio, $C_{1-18}$ alkylsulfoxide, $C_{1-18}$ alkylsulfone, $C_{1-18}$ halo-alkyl, $C_{2-18}$ halo-alkenyl, $C_{2-18}$ halo-alkynyl, $C_{1-18}$ halo-alkoxy, $C_{1-18}$ halo-alkylthio, $C_{3-10}$ cycloalkyl, $C_{3-10}$ cycloalkenyl, $C_{7-10}$ cycloalkynyl, halogen, OH, CN, cyanoalkyl, —CO$_2$R$^{18}$, NO$_2$, —NR$^7$R$^8$, $C_{1-18}$ haloalkyl, C(=O)R$^{18}$, C(=S)R$^{18}$, SH, aryl, aryloxy, arylthio, arylsulfoxide, arylsulfone, arylsulfonamide, aryl($C_{1-18}$)alkyl, aryl($C_{1-18}$)alkyloxy, aryl($C_{1-18}$)alkylthio, heterocycle, $C_{1-18}$ hydroxyalkyl, where each may be optionally substituted with at least 1 $R^{19}$;
  $R^7$ and $R^8$ are independently selected from hydrogen, $C_{1-18}$ alkyl, $C_{1-18}$ alkenyl, aryl, $C_{3-10}$ cycloalkyl, $C_{4-10}$ cycloalkenyl, heterocycle, —C(=O)R$^{12}$; —C(=S)R$^{12}$, an amino acid residue linked through a carboxyl group thereof, or where $R^7$ and $R^8$ together with the nitrogen form a heterocycle;
  $R^9$ and $R^{18}$ are independently selected from hydrogen, OH, $C_{1-18}$ alkyl, $C_{2-18}$ alkenyl, $C_{3-10}$ cycloalkyl, $C_{4-10}$ cycloalkenyl, $C_{1-18}$ alkoxy, —NR$^{15}$R$^{16}$, aryl, an amino acid residue linked through an amino group of the amino acid, CH$_2$OCH(=O)R$^{9a}$, or CH$_2$C(=O)OR$^{9a}$ where $R^{9a}$ is $C_1$-$C_{12}$ alkyl, $C_6$-$C_{20}$ aryl, $C_6$-$C_{20}$ alkylaryl or $C_6$-$C_{20}$ aralkyl;
  $R^{10}$ and $R^{11}$ are independently selected from the group consisting of hydrogen, $C_{1-18}$ alkyl, $C_{2-18}$ alkenyl, $C_{3-10}$ cycloalkyl, $C_{4-10}$ cycloalkenyl, aryl, —C(=O)R$^{12}$, heterocycle, or an amino acid residue;
  $R^{12}$ is selected from the group consisting of hydrogen, $C_{1-18}$ alkyl, $C_{2-18}$ alkenyl, aryl, $C_{3-10}$ cycloalkyl, $C_{4-10}$ cycloalkenyl, or an amino acid residue;
  $R^{15}$ and $R^{16}$ are independently selected from hydrogen, $C_{1-18}$ alkyl, $C_{2-18}$ alkenyl, $C_{2-18}$ alkynyl, aryl, $C_{3-10}$ cycloalkyl, $C_{4-10}$ cycloalkenyl, or an amino acid residue;
  $R^{17}$ is independently M-Q- wherein M is a ring optionally substituted with 1 or more $R^{19}$, and Q is a bond or a linking group connecting M to $R^3$ having 1 to 10 atoms selected from C and optionally 1 or more O, N or S atoms and optionally substituted with 1 or more $R^{19}$;
  $R^{19}$ is selected from hydrogen, $C_{1-18}$ alkyl, $C_{2-18}$ alkenyl, $C_{2-18}$ alkynyl, $C_{1-18}$ alkoxy, $C_{2-18}$ alkenyloxy, $C_{2-18}$ alkynyloxy, $C_{1-18}$ alkylthio, $C_{3-10}$ cycloalkyl, $C_{4-10}$ cycloalkenyl, $C_{4-10}$ cycloalkynyl, halogen, —OH, —CN, cyanoalkyl, —NO$_2$, —NR$^{20}$R$^{21}$, $C_{1-18}$ haloalkyl, $C_{1-18}$ haloalkyloxy, —C(=O)R$^{18}$, —C(=O)OR$^{18}$, —OalkenylC(=O)OR$^{18}$, —OalkylC(=O)NR$^{20}$R$^{21}$, —OalkylOC(=O)R$^{18}$, —C(=S)R$^{18}$, SH, —C(=O)N($C_{1-6}$alkyl), —N(H)S(O)(O)($C_{1-6}$ alkyl), aryl, heterocycle, $C_{1-18}$alkylsulfone, arylsulfoxide, arylsulfonamide, aryl($C_{1-18}$)alkyloxy, aryloxy, aryl($C_{1-18}$ alkyl)oxy, arylthio, aryl($C_{1-18}$) alkylthio or aryl($C_{1-18}$)alkyl, where each may be optionally substituted with 1 or more =O, NR$^{20}$R$^{21}$, CN, $C_{1-18}$ alkoxy, heterocycle, $C_{1-18}$ haloalkyl, heterocycle alkyl, heterocycle connected to $R^{17}$ by alkyl, alkoxyalkoxy or halogen;
  $R^{20}$ and $R^{21}$ are independently selected from hydrogen, $C_{1-18}$ alkyl, $C_{2-18}$ alkenyl, $C_{2-18}$ alkynyl, aryl, $C_{3-10}$ cycloalkyl, $C_{4-10}$ cycloalkenyl, —C(=O)R$^{12}$, or —C(=S)R$^{12}$;
  $R^{25}$ and $R^{26}$ are independently not present or are selected from hydrogen, $C_{1-18}$ alkyl, $C_{3-10}$cycloalkyl, aryl and heterocycle, where each is optionally independently substituted with 1 to 4 of $C_{1-6}$ alkyl, $C_{1-6}$ alkoxy, halo, CH$_2$OH, benzyloxy, and OH; and
  $R^{27}$ is selected from hydrogen, $C_{1-18}$ alkyl, $C_{3-10}$ cycloalkyl, ($C_{3-10}$cycloalkyl)-$C_{1-6}$ alkyl, aryl, and aryl $C_{1-18}$ alkyl, and
  salts, tautomers, polymorphs, isomers and solvates thereof.

The various embodiments above represent subgeneric groups of compounds. However, it will be understood that the compounds of this invention also comprise other subgeneric classes in which various substitutent groups are mixed and matched from any of the foregoing subgeneric groups, i.e., additional classes of compounds falling within the scope of this invention optionally will contain $R^{19}$ from the main embodiment (claim 1) but also a narrower Y group (e.g., Y=bond) from another disclosed embodiment, in any combination or permutation.

Utilities

The compounds of this invention, or the metabolites produced from these compounds in vivo, have a large number of uses. They are useful in immunology, chromatography, diagnostics and therapeutics, among other fields.

The compounds of the formulas of this invention are conjugated to immunogenic polypeptides as a reagent for eliciting antibodies capable of binding specifically to the polypeptide, to the compounds or to their metabolic products which retain immunologically recognized epitopes (sites of antibody binding). These immunogenic compositions therefore are useful as intermediates in the preparation of antibodies for use in diagnostics, quality control, or the like, or in assays for the compounds of the formulas of this invention or their novel metabolic products. The compounds are useful for raising antibodies against otherwise non-immunogenic polypeptides, in that the compounds serve as haptenic sites stimulating an immune response which cross-reacts with the unmodified conjugated protein.

Conjugates of the compounds of the formulas of this invention with immunogenic polypeptides such as albumin or keyhole limpet hemocyanin generally are useful as immunogens. The polypeptides are conjugated at the same sites denoted for amino acids. The metabolic products described above may retain a substantial degree of immunological cross reactivity with the compounds of the invention. Thus, the antibodies of this invention will be capable of binding to the unprotected compounds of the invention without binding to the protected compounds. Alternatively the metabolic products will be capable of binding to the protected compounds and/or the metabolitic products without binding to the protected compounds of the invention, or will be capable of binding specifically to any one or all three. The antibodies desirably will not substantially cross-react with naturally-occurring materials. Substantial cross-reactivity is reactivity under specific assay conditions for specific analytes sufficient to interfere with the assay results.

The immunogens of this invention contain the compound of this invention presenting the desired epitope in association with an immunogenic substance. Within the context of the invention such association means covalent bonding to form an immunogenic conjugate (when applicable) or a mixture of non-covalently bonded materials, or a combination of the above. Immunogenic substances include adjuvants such as Freund's adjuvant, immunogenic proteins such as viral, bacterial, yeast, plant and animal polypeptides, in particular keyhole limpet hemocyanin, serum albumin, bovine thyroglobulin or soybean trypsin inhibitor, and immunogenic polysaccharides. Typically, the compound having the structure of the desired epitope is covalently conjugated to an immunogenic polypeptide or polysaccharide by the use of a polyfunctional (ordinarily bifunctional) cross-linking agent. Methods for the manufacture of hapten immunogens are conventional per se, and any of the methods used heretofore for conjugating haptens to immunogenic polypeptides or the like are suitably employed here as well, taking into account the functional groups on the precursors or hydrolytic products which are available for cross-linking and the likelihood of producing antibodies specific to the epitope in question as opposed to the immunogenic substance.

Typically the polypeptide is conjugated to a site on the compound of the invention distant from the epitope to be recognized.

The conjugates are prepared in conventional fashion. For example, the cross-linking agents N-hydroxysuccinimide, succinic anhydride or alkN=C=Nalk are useful in preparing the conjugates of this invention. The conjugates comprise a compound of the invention attached by a bond or a linking group of 1-100, typically, 1-25, more typically 1-10 carbon atoms to the immunogenic substance. The conjugates are separated from starting materials and by products using chromatography or the like, and then are sterile filtered and vialed for storage.

Animals are typically immunized against the immunogenic conjugates or derivatives and antisera or monoclonal antibodies prepared in conventional fashion.

The compounds of this invention are useful as linkers, spacers or affinity (typically hydrophobic) moieties in preparing affinity absorption matrices. The compounds of the invention optionally are bound covalently to an insoluble matrix and used for affinity chromatography separations, depending on the nature of the groups of the compounds, for example compounds with pendant aryl groups are useful in making hydrophobic affinity columns.

They also are useful as linkers and spacers in preparing immobilized enzymes for process control, or in making immunoassay reagents. The compounds herein contain functional groups that are suitable as sites for cross-linking desired substances. For example, it is conventional to link affinity reagents such as hormones, peptides, antibodies, drugs, and the like to insoluble substrates. These insolubized reagents are employed in known fashion to absorb binding partners for the affinity reagents from manufactured preparations, diagnostic samples and other impure mixtures. Similarly, immobilized enzymes are used to perform catalytic conversions with facile recovery of enzyme. Bifunctional compounds are commonly used to link analytes to detectable groups in preparing diagnostic reagents.

The compounds of this invention are labeled with detectable moieties such biotin, radioisotopes, enzymes and the like for diagnostic purposes. Suitable techniques for accomplishing the labeling of the compounds of the formulas of this invention are well known and will be apparent to the artisan from consideration of this specification as a whole. For example, one suitable site for labeling is $R^{17}$ or $R^{19}$.

More typically, however, the compounds of the invention are employed for the treatment or prophylaxis of viral infections such as yellow fever virus, Dengue virus, hepatitis B virus, hepatitis G virus, Classical Swine Fever virus or the Border Disease Virus, but more particularly Flaviviral or Picornaviral infections, in particular, HCV and BVDV.

The therapeutic compound(s) of this invention are administered to a subject mammal (including a human) by any means well known in the art, i.e. orally, intranasally, subcutaneously, intramuscularly, intradermally, intravenously, intra-arterially, parenterally or by catheterization. The therapeutically effective amount of the compound(s) is a Flaviviral or Picornaviral growth inhibiting amount. More preferably, it is a Flaviviral or Picornaviral replication inhibiting amount or a Flaviviral or Picornaviral enzyme inhibiting amount of the compounds of the formulas of this invention. This is believed to correspond to an amount which ensures a plasma level of between about 1 µg/ml and 100 mg/ml, optionally of 10 mg/ml. This optionally is achieved by administration of a dosage of in the range of 0.001 mg to 60 mg, preferably 0.01 mg to 10 mg, preferably 0.1 mg to 1 mg per day per kg bodyweight for humans. These are starting points for determining the optimal dosage of the compound of this invention. The actual amount will depend upon many factors known to the artisan, including bioavailability of the compound, whether it contains a prodrug functionality, its metabolism and distribution in the subject and its potency, among others. It typically is necessary to determine the proper dosing in the clinical setting, and this is well within the skill of the ordinary artisan. The therapeutically effective amount of the compound(s) of this invention optionally are divided into several sub-units per day or are administered at daily or more than one day intervals, depending upon the pathologic condition to be treated, the patient's condition and the nature of the compound of this invention.

As is conventional in the art, the evaluation of a synergistic effect in a drug combination may be made by analyzing the quantification of the interactions between individual drugs, using the median effect principle described by Chou et al. in *Adv. Enzyme Reg.* (1984) 22:27 or tests such as, but not limited to, the isobologram method, as previously described by Elion et al. in *J. Biol. Chem.* (1954) 208:477-488 and by Baba et al. in *Antimicrob. Agents Chemother.* (1984) 25:515-517, using $EC_{50}$ for calculating the fractional inhibitory concentration.

Suitable anti-viral agents for inclusion in combination antiviral compositions or for coadministration in a course of therapy include, for instance, interferon alpha, ribavirin, a compound falling within the scope of disclosure of EP 1162196, WO 03/010141, WO 03/007945, WO04/005286 and WO 03/010140, a compound falling within the scope of disclosure of WO 00/204425, and other patents or patent applications within their patent families, in amounts of 1 to 99.9% by weight compound of this invention, preferably from 1 to 99% by weight, more preferably from 5 to 95% by weight as can be readily determined by one skilled in the art. Such co-administered agents need not be formulated in the same dosage form as the compound of the invention. They optionally are simply administered to the subject in the course of treatment along with a course of treatment with a compound of formula (A).

The present invention further provides veterinary compositions comprising at least one active ingredient as above defined together with a veterinary carrier therefore, for example in the treatment of BVDV. Veterinary carriers are materials useful for the purpose of administering the composition and are excipients which are otherwise inert or acceptable in the veterinary art and are compatible with the compound of this invention. These veterinary compositions may be administered orally, parenterally or by any other desired route.

The compounds of the invention optionally are bound covalently to an insoluble matrix and used for affinity chromatography (separations, depending on the nature of the groups of the compounds, for example compounds with pendant aryl are useful in hydrophobic affinity separations.

The compounds of the invention are employed for the treatment or prophylaxis of viral infections, more particularly Flaviviral or Picornaviral infections, in particular, HCV and BVDV. When using one or more derivatives of the formula (A) as defined herein:

the active ingredients of the compound(s) may be administered to the mammal (including a human) to be treated by any means well known in the art, i.e. orally, intranasally, subcutaneously, intramuscularly, intradermally, intravenously, intra-arterially, parenterally or by catheterization.

the therapeutically effective amount of the preparation of the compound(s), especially for the treatment of viral infections in humans and other mammals, preferably is a Flaviviral or Picornaviral enzyme inhibiting amount. More preferably, it is a Flaviviral or Picornaviral replication inhibiting amount or a Flaviviral or Picornaviral enzyme inhibiting amount of the derivative(s) of formula (A) as defined herein corresponds to an amount which ensures a plasma level of between 1 µg/ml and 100 mg/ml, optionally of 10 mg/ml. This can be achieved by administration of a dosage of in the range of 0.001 mg to 20 mg, preferably 0.01 mg to 5 mg, preferably 0.1 mg to 1 mg per day per kg bodyweight for humans. Depending upon the pathologic condition to be treated and the patient's condition, the said effective amount may be divided into several sub-units per day or may be administered at more than one day intervals.

The present invention further relates to a method for preventing or treating a viral infections in a subject or patient by administering to the patient in need thereof a therapeutically effective amount imidazo[4,5-d]pyrimidine derivatives of the present invention. The therapeutically effective amount of the preparation of the compound(s), especially for the treatment of viral infections in humans and other mammals, preferably is a Flaviviral or Picornaviral enzyme inhibiting amount. More preferably, it is a Flaviviral or Picornaviral replication inhibiting amount or a Flaviviral or Picornaviral enzyme inhibiting amount of the derivative(s) of formula (A) as defined herein. Suitable dosage is usually in the range of 0.001 mg to 60 mg, optionally 0.01 mg to 10 mg, optionally 0.1 mg to 1 mg per day per kg bodyweight for humans. Depending upon the pathologic condition to be treated and the patient's condition, the said effective amount may be divided into several sub-units per day or may be administered at more than one day intervals.

This principle may be applied to a combination of different antiviral drugs of the invention or to a combination of the antiviral drugs of the invention with other drugs that exhibit anti-BVDV or anti-HCV activity.

The invention thus relates to a pharmaceutical composition or combined preparation having synergistic effects against a viral infection and containing: Either:

A) a combination of two or more of the imidazo[4,5-d] pyrimidine derivatives of the present invention, and B) optionally one or more pharmaceutical excipients or pharmaceutically acceptable carriers, for simultaneous, separate or sequential use in the treatment or prevention of a viral infection, or C) one or more anti-viral agents, and D) at least one of the imidazo[4,5-d]pyrimidine derivatives of the present invention, and E) optionally one or more pharmaceutical excipients or pharmaceutically acceptable carriers, for simultaneous, separate or sequential use in the treatment or prevention of a viral infection.

Suitable anti-viral agents for inclusion into the synergistic antiviral compositions or combined preparations of this invention include, for instance, interferon-alfa (either pegylated or not), ribavirin and other selective inhibitors of the replication of BVDV or HCV.

The pharmaceutical composition or combined preparation with synergistic activity against viral infection according to this invention may contain the imidazo[4,5-d]pyrimidine derivatives of the present invention over a broad content range depending on the contemplated use and the expected effect of the preparation. Generally, the content of the imidazo[4,5-d] pyrimidine derivatives of the present invention of the combined preparation is within the range of 0.1 to 99.9% by weight, preferably from 1 to 99% by weight, more preferably from 5 to 95% by weight.

According to a particular embodiment of the invention, the compounds of the invention may be employed in combination with other therapeutic agents for the treatment or prophylaxis of Flaviviral or Picornaviral infections, optionally, HCV and BVDV. The invention therefore relates to the use of a composition comprising:

(a) one or more compounds of the formulas of this invention, and (b) one or more Flaviviral or Picornaviral enzyme inhibitors as biologically active agents in respective proportions such as to provide a synergistic effect against a viral infection, particularly a Flaviviral or Picornaviral infection in a mammal, for instance in the form of a combined preparation for simultaneous, separate or sequential use in viral infection therapy, such as of HCV, BVDV and Coxsackie virus. Examples of such further therapeutic agents for use in combinations include agents that are effective for the treatment or prophylaxis of these infections, including interferon alpha, ribavirin, a compound faling within the scope of disclosure EP 1162196, WO 03/010141, WO 03/007945, WO04/ 005286 and WO 03/010140, a compound falling within the scope of disclosure WO 00/204425, and other patents or patent applications within their patent families or all the foregoing filings and/or an inhibitor of Flaviviral protease and/or one or more additional Flavivirus polymerase inhibitors. When using a combined preparation of (a) and (b):

the active ingredients (a) and (b) may be administered to the mammal (including a human) to be treated by any means well known in the art, i.e. orally, intranasally, subcutaneously, intramuscularly, intradermally, intravenously, intra-arterially, parenterally or by catheterization.

the therapeutically effective amount of the combined preparation of (a) and (b), especially for the treatment of viral infections in humans and other mammals, particularly is a Flaviviral or Picornaviral enzyme inhibiting amount. More particularly, it is a Flaviviral or Picornaviral replication inhibiting amount of derivative (a) and a Flaviviral or Picornaviral enzyme inhibiting amount of inhibitor (b). Still more particularly when the said Flaviviral or Picornaviral enzyme inhibitor (b) is a polymerase inhibitor, its effective amount is a polymerase inhibiting amount. When the said Flaviviral or Picornaviral enzyme inhibitor (b) is a protease inhibitor, its effective amount is a protease inhibiting amount.

ingredients (a) and (b) may be administered simultaneously but it is also beneficial to administer them separately or sequentially, for instance within a relatively short period of time (e.g. within about 24 hours) in order to achieve their functional fusion in the body to be treated.

The invention also relates to the compounds of the formulas of this invention being used for inhibition of the proliferation of other viruses than BVDV, HCV or Coxsackie virus, particularly for the inhibition of other flaviviruses or picornaviruses, with in particular yellow fever virus, Dengue virus, hepatitis B virus, hepatitis G virus, Classical Swine Fever virus or the Border Disease Virus, and also for the inhibition of HIV and other retroviruses or lentiviruses.

More generally, the invention relates to the compounds of the formulas of this invention being useful as agents having biological activity (particularly antiviral activity) or as diagnostic agents. Any of the uses mentioned with respect to the present invention may be restricted to a non-medical use, a non-therapeutic use, a non-diagnostic use, or exclusively an in vitro use, or a use related to cells remote from an animal.

Salts and Solvates

The term "pharmaceutically acceptable salts" as used herein means the therapeutically active non-toxic salt forms formed by the compounds of the compounds of this invention. Such salts may include those derived by combination of appropriate cations such as alkali and alkaline earth metal ions or ammonium and quaternary amino ions with an acid anion moiety, typically a carboxylic acid.

The compounds of the invention may bear multiple positive or negative charges. The net charge of the compounds of the invention may be either positive or negative. Any associated counter ions are typically dictated by the synthesis and/or isolation methods by which the compounds are obtained. Typical counter ions include, but are not limited to ammonium, sodium, potassium, lithium, halides, acetate, trifluoroacetate, etc., and mixtures thereof. It will be understood that the identity of any associated counter ion is not a critical feature of the invention, and that the invention encompasses the compounds in association with any type of counter ion. Moreover, as the compounds can exist in a variety of different forms, the invention is intended to encompass not only forms of the compounds that are in association with counter ions (e.g., dry salts), but also forms that are not in association with counter ions (e.g., aqueous or organic solutions).

The compounds of this invention include the solvates formed with the compounds of this invention and their salts, such as for example hydrates, alcoholates and the like. The compositions herein comprise compounds of the invention in their un-ionized, as well as zwitterionic form, and combinations with stoichiometric amounts of water as in hydrates.

Also included within the scope of this invention are the salts of the compounds of this invention with one or more amino acids as described above. The amino acid typically is one bearing a side chain with a basic or acidic group, e.g., lysine, arginine or glutamic acid, or a neutral group such as glycine, serine, threonine, alanine, isoleucine, or leucine.

Salts of acids or bases which are not physiologically acceptable may also find use, for example, in the preparation or purification of a compound of this invention. All salts, whether or not derived form a physiologically acceptable acid or base, are within the scope of the present invention.

The compounds of this invention optionally comprise salts of the compounds herein, especially pharmaceutically acceptable non-toxic salts containing, for example, Na+, Li+, K+, Ca+2 and Mg+2. Such salts may include those derived by combination of appropriate cations such as alkali and alkaline earth metal ions or ammonium and quaternary amino ions with an acid anion moiety, typically a carboxylic acid. The compounds of the invention may bear multiple positive or negative charges. The net charge of the compounds of the invention may be either positive or negative. Any associated counter ions are typically dictated by the synthesis and/or isolation methods by which the compounds are obtained. Typical counter ions include, but are not limited to ammonium, sodium, potassium, lithium, halides, acetate, trifluoroacetate, etc., and mixtures thereof. It will be understood that the identity of any associated counter ion is not a critical feature of the invention, and that the invention encompasses the compounds in association with any type of counter ion. Moreover, as the compounds can exist in a variety of different forms, the invention is intended to encompass not only forms of the compounds that are in association with counter ions (e.g., dry salts), but also forms that are not in association with counter ions (e.g., aqueous or organic solutions).

Metal salts typically are prepared by reacting the metal hydroxide with a compound of this invention. Examples of metal salts which are prepared in this way are salts containing Li+, Na+, Ca+2 and Mg+2 and K+. A less soluble metal salt can be precipitated from the solution of a more soluble salt by addition of the suitable metal compound. In addition, salts may be formed from acid addition of certain organic and inorganic acids to basic centers, typically amines, or to acidic groups. Examples of such appropriate acids include, for instance, inorganic acids such as hydrohalogen acids, e.g. hydrochloric or hydrobromic acid, sulfuric acid, nitric acid, phosphoric acid and the like; or organic acids such as, for example, acetic, propanoic, hydroxyacetic, benzoic, 2-hydroxypropanoic, 2-oxopropanoic, lactic, fumaric, tartaric, pyruvic, maleic, malonic, malic, salicylic (i.e. 2-hydroxybenzoic), p-aminosalicylic, isethionic, lactobionic, succinic oxalic and citric acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids, $C_1$-$C_6$ alkylsulfonic, benzenesulfonic, p-toluenesulfonic, cyclohexanesulfamic, and the like. Exemplary salts include mesylate and HCl.

Also included within the scope of this invention are the salts of the parental compounds with one or more amino acids, especially the naturally-occurring amino acids found as protein components. The amino acid typically is one bearing a side chain with a basic or acidic group, e.g., lysine, arginine or glutamic acid, or a neutral group such as glycine, serine, threonine, alanine, isoleucine, or leucine.

The compounds of the invention also include physiologically acceptable salts thereof. Examples of physiologically acceptable salts of the compounds of the invention include salts derived from an appropriate base, such as an alkali metal (for example, sodium), an alkaline earth (for example, magnesium), ammonium and NX4+ (wherein X is $C_1$-$C_4$ alkyl). Physiologically acceptable salts of an hydrogen atom or an amino group include salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids. Physiologically acceptable salts of a compound containing a hydroxy group include the anion of said compound in combination with a suitable cation such as Na+ and NX4+ (wherein X typically is independently selected from H or a $C_1$-$C_4$ alkyl group). However, salts of acids or bases which are not physiologically acceptable may also find use, for example, in the preparation or purification of a physiologically acceptable compound. All salts, whether or not derived form a physiologically acceptable acid or base, are within the scope of the present invention.

Isomers

The term "isomers" as used herein means all possible isomeric forms, including tautomeric and stereochemical forms, which the compounds of the formulas of this invention may possess, but not including position isomers. Typically, the structures shown herein exemplify only one tautomeric or resonance form of the compounds, but the corresponding alternative configurations are contemplated as well. Unless otherwise stated, the chemical designation of compounds denotes the mixture of all possible stereochemically isomeric forms, said mixtures containing all diastereomers and enantiomers (since the compounds of the formulas of this invention may have one or more chiral centers), as well as the stereochemically pure or enriched isomers. More particularly, stereogenic centers may have either the R- or S-configuration, and double or triple bonds optionally are in either the cis- or trans-configuration.

Enriched isomeric forms of a compound of this invention are defined as a single isomer substantially free of the compound's other enantiomers or diastereomers. In particular, the term "stereoisomerically enriched" or "chirally enriched" relates to compounds having a single stereoisomeric proportion of at least about 80% (i.e. at least 90% of one isomer and at most 10% of the other possible isomers), preferably at least 90%, more preferably at least 94% and most preferably at least 97%. The terms "enantiomerically pure" and "diastereomerically pure" contain undetectable levels of any other isomer.

Separation of stereoisomers is accomplished by standard methods known to those in the art. One enantiomer of a compound of the invention can be separated substantially free of its opposing enantiomer by a method such as formation of diastereomers using optically active resolving agents ("Stereochemistry of Carbon Compounds," (1962) by E. L. Eliel, McGraw Hill; Lochmuller, C. H., (1975) J. Chromatogr., 113:(3) 283-302). Separation of isomers in a mixture can be accomplished by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure enantiomers, or (3) enantiomers can be separated directly under chiral conditions. Under method (1), diastereomeric salts can be formed by reaction of enantiomerically pure chiral bases such as brucine, quinine, ephedrine, strychnine, a-methyl-b-phenylethylamine (amphetamine), and the like with asymmetric compounds bearing an acidic functionality, such as carboxylic acid and sulfonic acid.

The diastereomeric salts optionally are induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts. Alternatively, by method (2), the substrate to be resolved may be reacted with one enantiomer of a chiral compound to form a diastereomeric pair (Eliel, E. and Wilen, S. (1994). Stereochemistry of Organic Compounds, John Wiley & Sons, Inc., p. 322). Diastereomeric compounds can be formed by reacting asymmetric compounds with enantiomerically pure chiral derivatizing reagents, such as menthyl derivatives, followed by separation of the diastereomers and hydrolysis to yield the free, enantiomerically enriched xanthene. A method of determining optical purity involves making chiral esters, such as a menthyl ester or Mosher ester, a-methoxy-a-(trifluoromethyl)phenyl acetate (Jacob III. (1982) J. Org. Chem. 47:4165), of the racemic mixture, and analyzing the NMR spectrum for the presence of the two atropisomeric diastereomers. Stable diastereomers can be separated and isolated by normal- and reverse-phase chromatography following methods for separation of atropisomeric naphthyl-isoquinolines (Hoye, T., WO 96/15111). Under method (3), a racemic mixture of two asymmetric enantiomers is separated by chromatography using a chiral stationary phase. Suitable chiral stationary phases are, for example, polysaccharides, in particular cellulose or amylose derivatives. Commercially available polysaccharide based chiral stationary phases are ChiralCel™ CA, OA, OB5, OC5, OD, OF, OG, OJ and OK, and Chiralpak™ AD, AS, OP(+) and OT(+). Appropriate eluents or mobile phases for use in combination with said polysaccharide chiral stationary phases are hexane and the like, modified with an alcohol such as ethanol, isopropanol and the like. ("Chiral Liquid Chromatography" (1989) W. J. Lough, Ed. Chapman and Hall, New York; Okamoto, (1990). "Optical resolution of dihydropyridine enantiomers by Highperformance liquid chromatography using phenylcarbamates of polysaccharides as a chiral stationary phase", J. of Chromatogr. 513:375-378).

As used herein and unless otherwise stated, the term "enantiomer" means each individual optically active form of a compound of the invention, having an optical purity or enantiomeric excess (as determined by methods standard in the art) of at least 80% (i.e. at least 90% of one enantiomer and at most 10% of the other enantiomer), preferably at least 90% and more preferably at least 98%.

The term "isomers" as used herein means all possible isomeric forms, including tautomeric and sterochemical forms, which the compounds of the formulas of this invention may possess, but not including position isomers. Typically, the structures shown herein exemplify only one tautomeric or resonance form of the compounds, but the corresponding alternative configurations are contemplated as well. Unless otherwise stated, the chemical designation of compounds denotes the mixture of all possible stereochemically isomeric forms, said mixtures containing all diastereomers and enantiomers (since the compounds of the formulas of this invention may have at least one chiral center) of the basic molecular structure, as wel as the stereochemically pure or enriched compounds. More particularly, stereogenic centers may have either the R- or S-configuration, and multiple bonds may have either cis- or trans-configuration.

Pure isomeric forms of the said compounds are defined as isomers substantially free of other enantiomeric or diastereomeric forms of the same basic molecular structure. In particular, the term "stereoisomerically pure" or "chirally pure" relates to compounds having a stereoisomeric excess of at least about 80% (i.e. at least 90% of one isomer and at most 10% of the other possible isomers), preferably at least 90%, more preferably at least 94% and most preferably at least 97%. The terms "enantionierically pure" and "diastereomerically pure" should be understood in a similar way, having regard to the enantiomeric excess, respectively the diastereomeric excess, of the mixture in question.

Separation of stereoisomers is accomplished by standard methods known to those in the art. One enantiomer of a compound of the invention can be separated substantially free of its opposing enantiomer by a method such as formation of diastereomers using optically active resolving agents ("Stereochemistry of Carbon Compounds," (1962) by E. L. Eliel, McGraw Hill; Lochmuller, C. H., (1975) J. Chromatogr., 113:(3) 283-302). Separation of isomers in a mixture can be accomplished by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure enantiomers, or (3) enantiomers can be separated directly under chiral conditions. Under method (1), diastereomeric salts can be formed by reaction of enantiomerically pure chiral bases such as brucine, quinine, ephedrine, strychnine, a-methyl-b-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts. Alternatively, by method (2), the substrate to be resolved may be reacted with one enantiomer of a chiral compound to form a diastereomeric pair (Eliel, E. and Wilen, S. (1994) Stereochemistry of Organic Compounds, John Wiley & Sons, Inc., p. 322). Diastereomeric compounds can be formed by reacting asymmetric compounds with enantiomerically pure chiral derivatizing reagents, such as menthyl derivatives, followed by separation of the diastereomers and hydrolysis to yield the free, enantiomerically enriched xanthene. A method of determining optical purity involves making chiral esters, such as a menthyl ester or Mosher ester, a-methoxy-a-(trifluoromethyl)phenyl acetate (Jacob III. (1982) J. Org. Chem. 47:4165), of the racemic mixture, and analyzing the NMR spectrum for the presence of the two atropisomeric diastereomers. Stable diastereomers can be separated and isolated by normal- and reverse-phase chromatography following methods for separation of atropisomeric naphthyl-isoquinolines (Hoye, T., WO 96/15111). Under method (3), a racemic mixture of two asymmetric enantiomers is separated by chromatography using a chiral stationary phase. Suitable chiral stationary phases are, for example, polysaccharides, in particular cellulose or amylose derivatives. Commercially available polysaccharide based chiral stationary phases are ChiralCel™ CA, OA, OB5, OC5, OD, OF, OG, OJ and OK, and Chiralpak™ AD, AS, OP(+) and OT(+). Appropriate eluents or mobile phases for use in combination with said polysaccharide chiral stationary phases are hexane and the like, modified with an alcohol such as ethanol, isopropanol and the like. ("Chiral Liquid Chromatography" (1989) W. J. Lough, Ed. Chapman and Hall, New York; Okamoto, (1990) "Optical resolution of dihydropyridine enantiomers by High-performance liquid chromatography using phenylcarbamates of polysaccharides as a chiral stationary phase", J. of Chromatogr. 513:375-378).

The terms cis and trans are used herein in accordance with Chemical Abstracts nomenclature and include reference to the position of the substituents on a ring moiety. The absolute stereochemical configuration of the compounds of formula (1) may easily be determined by those skilled in the art while using well-known methods such as, for example, X-ray diffraction.

Metabolites

The present invention also provides the in vivo metabolic products of the compounds described herein, to the extent such products are novel and unobvious over the prior art. Such products may result for example from the oxidation, reduction, hydrolysis, amidation, esterification and the like of the administered compound, primarily due to enzymatic processes. Accordingly, the invention includes novel and unobvious compounds produced by a process comprising contacting a compound of this invention with a mammal for a period of time sufficient to yield a metabolic product thereof. Such products typically are identified by preparing a radiolabelled (e.g. C14 or H3) compound of the invention, administering it parenterally in a detectable dose (e.g. greater than about 0.5 mg/kg) to an animal such as rat, mouse, guinea pig, monkey, or to man, allowing sufficient time for metabolism to occur (typically about 30 seconds to 30 hours) and isolating its conversion products from the urine, blood or other biological samples. These products are easily isolated since they are labeled (others are isolated by the use of antibodies capable of binding epitopes surviving in the metabolite). The metabolite structures are determined in conventional fashion, e.g. by MS or NMR analysis. In general, analysis of metabolites is done in the same way as conventional drug metabolism studies well-known to those skilled in the art. The conversion products, so long as they are not otherwise found in vivo, are useful in diagnostic assays for therapeutic dosing of the compounds of the invention even if they possess no antiviral activity of their own.

Formulations

The compounds of the invention optionally are formulated with conventional pharmaceutical carriers and excipients, which will be selected in accord with ordinary practice. Tablets will contain excipients, glidants, fillers, binders and the like. Aqueous formulations are prepared in sterile form, and when intended for delivery by other than oral administration generally will be isotonic. Formulations optionally contain excipients such as those set forth in the "Handbook of Pharmaceutical Excipients" (1986) and include ascorbic acid and other antioxidants, chelating agents such as EDTA, carbohydrates such as dextrin, hydroxyalkylcellulose, hydroxyalkylmethylcellulose, stearic acid and the like.

Subsequently, the term "pharmaceutically acceptable carrier" as used herein means any material or substance with which the active ingredient is formulated in order to facilitate its application or dissemination to the locus to be treated, for instance by dissolving, dispersing or diffusing the said composition, and/or to facilitate its storage, transport or handling without impairing its effectiveness. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, suspensions, ointments, creams, tablets, pellets or powders.

Suitable pharmaceutical carriers for use in the said pharmaceutical compositions and their formulation are well known to those skilled in the art, and there is no particular restriction to their selection within the present invention. They may also include additives such as wetting agents, dispersing agents, stickers, adhesives, emulsifying agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals. The pharmaceutical compositions of the present invention may be prepared in any known manner, for instance by homogeneously mixing, coating and/or grinding the active ingredients, in a one-step or multi-steps procedure, with the selected carrier material. Where appropriate, the other additives such as surface-active agents are prepared by micronisation, for instance in view to obtain them in the form of microspheres usually having a diameter of about 1 to 10 gm, namely for the manufacture of microcapsules for controlled or sustained release of the active ingredients.

Suitable surface-active agents, also known as emulgent or emulsifier, to be used in the pharmaceutical compositions of the present invention are non-ionic, cationic and/or anionic materials having good emulsifying, dispersing and/or wetting properties. Suitable anionic surfactants include both water-soluble soaps and water-soluble synthetic surface-active agents. Suitable soaps are alkaline or alkaline-earth metal salts, unsubstituted or substituted ammonium salts of higher fatty acids ($C_{10}$-$C_{22}$), e.g. the sodium or potassium salts of oleic or stearic acid, or of natural fatty acid mixtures obtainable form coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylarylsulphonates are the sodium, calcium or alcoholamine salts of dodecylbenzene sulphonic acid or dibutyl-naphthalenesulphonic acid or a naphthalene-sulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardiolipin, dioctanylphosphatidyl-choline, dipalmitoylphosphatidyl-choline and their mixtures.

Suitable non-ionic surfactants include polyethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with poylypropylene glycol, ethylenediaminopolypropylene glycol containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants are nonylphenol-polyethoxyethanol, castor oil polyglycolic ethers, polypropylene/polyethylene oxide adducts, tributylphenoxypolyethoxyethanol, polyethyleneglycol and octylphenoxypolyethoxyethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants include quaternary ammonium salts, particularly halides, having 4 hydrocarbon radicals optionally substituted with halo, phenyl, substituted phenyl or hydroxy; for instance quaternary ammonium salts containing as N-substituent at least one $C_8$-$C_{22}$ alkyl radical (e.g. cetyl, lauryl, palmityl, myristyl, oleyl and the like) and, as further substituents, unsubstituted or halogenated lower alkyl, benzyl and/or hydroxy-lower alkyl radicals.

A more detailed description of surface-active agents suitable for this purpose may be found for instance in "McCutcheon's Detergents and Emulsifiers Annual" (MC Publishing Crop., Ridgewood, N.J., 1981), "Tensid-Taschenbucw', 2 d ed. (Hanser Verlag, Vienna, 1981) and "Encyclopaedia of Surfactants, (Chemical Publishing Co., New York, 1981).

Compounds of the invention and their physiologically acceptable salts (hereafter collectively referred to as the active ingredients) may be administered by any route appropriate to the condition to be treated, suitable routes including oral, rectal, nasal, topical (including ocular, buccal and sublingual), vaginal and parenteral (including subcutaneous, intramuscular, intravenous, intradermal, intrathecal and epidural). The preferred route of administration may vary with for example the condition of the recipient.

While it is possible for the active ingredients to be administered alone it is preferable to present them as pharmaceutical formulations. The formulations, both for veterinary and for human use, of the present invention comprise at least one active ingredient, as above described, together with one or more pharmaceutically acceptable carriers therefore and optionally other. therapeutic ingredients. The carrier(s) optimally are "acceptable" in the sense of being compatible with the other ingredients of the formulation and not deleterious to the recipient thereof. The formulations include those suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein. For infections of the eye or other external tissues e.g. mouth and skin, the formulations are optionally applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base. If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG400) and mixtures thereof. The topical formulations may desirably include a compound which enhances absorption or penetration of the active ingredient through the skin or other affected areas. Examples of such dermal penetration enhancers include dimethylsulfoxide and related analogs.

The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Optionally, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations.

The choice of suitable oils or fats for the formulation is based on achieving the desired cosmetic properties, since the solubility of the active compound in most oils likely to be used in pharmaceutical emulsion formulations is very low. Thus the cream should optionally be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. The active ingredient is optionally present in such formulations in a concentration of 0.5 to 20%, advantageously 0.5 to 10% particularly about 1.5% w/w. Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate. Formulations suitable for nasal administration wherein the carrier is a solid include a coarse powder having a particle size for example in the range 20 to 500 microns (including particle sizes in a range between 20 and 500 microns in increments of 5 microns such as 30 microns, 35 microns, etc), which is administered in the manner in which snuff is taken, i.e. by rapid inhalation through the nasal passage from a container of the powder held close up to the nose. Suitable formulations wherein the carrier is a liquid, for administration as for example a nasal spray or as nasal drops, include aqueous or oily solutions of the active ingredient. Formulations suitable for aerosol administration may be prepared according to conventional methods and may be delivered with other therapeutic agents.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavoring agents.

Compounds of the invention can be used to provide controlled release pharmaceutical formulations containing as active ingredient one or more compounds of the invention ("controlled release formulations") in which the release of the active ingredient can be controlled and regulated to allow less frequency dosing or to improve the pharmacokinetic or toxicity profile of a given invention compound. Controlled release formulations adapted for oral administration in which discrete units comprising one or more compounds of the invention can be prepared according to conventional methods.

Additional ingredients may be included in order to control the duration of action of the active ingredient in the composition. Control release compositions may thus be achieved by selecting appropriate polymer carriers such as for example polyesters, polyamino acids, polyvinyl pyrrolidone, ethylene-vinyl acetate copolymers, methylcellulose, carboxymethylcellulose, protamine sulfate and the like. The rate of drug release and duration of action may also be controlled by incorporating the active ingredient into particles, e.g. microcapsules, of a polymeric substance such as hydrogels, polylactic acid, hydroxymethylcellulose, polymethyl methacrylate and the other above-described polymers. Such methods include colloid drug delivery systems like liposomes, microspheres, microemulsions, nanoparticles, nanocapsules and so on. Depending on the route of administration, the pharmaceutical composition may require protective coatings. Pharmaceutical forms suitable for injectionable use include sterile aqueous solutions or dispersions and sterile powders for the extemporaneous preparation thereof. Typical carriers for this purpose therefore include biocompatible aqueous buffers, ethanol, glycerol, propylene glycol, polyethylene glycol and the like and mixtures thereof.

In view of the fact that, when several active ingredients are used in combination, they do not necessarily bring out their joint therapeutic effect directly at the same time in the mammal to be treated, the corresponding composition may also be in the form of a medical kit or package containing the two ingredients in separate but adjacent repositories or compartments. In the latter context, each active ingredient may therefore be formulated in a way suitable for an administration route different from that of the other ingredient, e.g. one of them may be in the form of an oral or parenteral formulation whereas the other is in the form of an ampoule for intravenous injection or an aerosol.

Suitable methods for drug delivery include colloid drug delivery systems like liposomes, microspheres, microemulsions, nanoparticles, nanocapsules and so on. Depending on the route of administration, the pharmaceutical composition may require protective coatings. Pharmaceutical forms suitable for injectionable use include sterile aqueous solutions or dispersions and sterile powders for the extemporaneous preparation thereof. Typical carriers for this purpose therefore include biocompatible aqueous buffers, ethanol, glycerol, propylene glycol, polyethylene glycol and the like and mixtures thereof.

Several active ingredients used in combination may not necessarily bring out their joint therapeutic effect directly at the same time in the mammal to be treated. Thus, the corresponding composition may also be in the form of a medical kit or package containing the two ingredients in separate but adjacent repositories or compartments. In the latter context, each active ingredient may therefore be formulated in a way suitable for an administration route different from that of the other ingredient, e.g. one of them may be in the form of an oral or parenteral formulation whereas the other is in the form of an ampoule for intravenous injection or an aerosol.

Exemplary Enumerated Compounds

By way of example and not limitation, embodiments of the invention are named below in tabular format (Table 7). Each embodiment of Table 7 is depicted as a substituted nucleus (Sc) in which the nucleus is designated by a number and each substituent is designated in order by further numbers. Table 1 is a schedule of nuclei used in forming the embodiments of Table 7. Each nucleus (Sc) is given a number designation from Table 1, and this designation appears first in each embodiment name. Similarly, Tables 2, 3, 4, 5 and 6 list the selected substituents, again by number designation.

Accordingly, each named embodiment of Table 7 is depicted by a number designating the nucleus from Table 1. If the nucleus is of formula 1 (from Table 1), then the letter and number substituents are in the order $R^1$ (Table 2), $R^3$ (Table 3), $R^4$ (Table 4), and X (Table 6). If the nucleus is of formula 2 (from Table 1), then the letter and number substituents are in the order $R^1$ (Table 2), $R^3$ (Table 3), 4 (Table 4), $R^{26}$ (Table 5), and X (Table 6). The same embodiments of the invention exist for the nucleus of formula 2 (Table 1) wherein the N at position 1 is substituted by $R^{25}$ (corresponding to the embodiments of $R^{26}$ of Table 5) and the single or double bonds in the imidazo pyridine ring are adjusted accordingly.

Each group is shown having one or more tildas ("~"). The tildas are the points of covalent attachment of the group.

TABLE 1

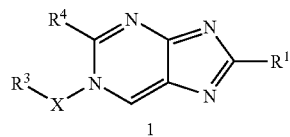

1

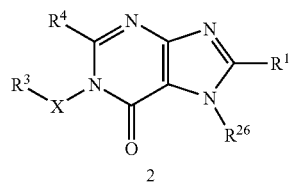

2

TABLE 2

R¹ Substituents

1: phenyl substituted with two $R^6$ groups (one on ring, one ortho)

2: phenyl substituted with two $R^6$ groups

3: phenyl substituted with Halo

4: phenyl substituted with Halo (ortho)

5: —5-membered benzoannellated ring having 1-2 nitrogen atoms and 1-2 $R^6$ groups 6: —6-membered benzoannellated ring having 1-2 nitrogen atoms and 1-2 $R^6$ groups 7: —napthyl having 1-2 $R^6$ groups

TABLE 3

R³ Substituents

1: phenyl substituted with two $R^{17}$ groups

2: phenyl substituted with $R^{17}$

3: isoxazole substituted with $R^{17}$

4: phenyl substituted with $R^{17}$ (para)

5: —HET—phenyl substituted with two $R^{19}$ groups; HET = heterocycle

6: isoxazole with phenyl substituted with two $R^{19}$ groups

TABLE 4
R⁴ Substituents
1
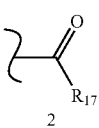
2
TABLE 5
R²⁶ Substituents
1
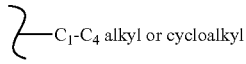
2
TABLE 6
X Substituents
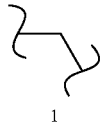
1
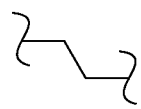
2
$\xi$—C₁-C₄ Alkylene—$\xi$,
$\xi$—C₁-C₂ Alkxoyalkylene—$\xi$, or
$\xi$—C₁-C₂ Thioalkylene—$\xi$
3
TABLE 7
Selected Embodiments of the Invention
Embodiments of Formula 1
1.1.1.1.1; 1.1.1.1.2; 1.1.1.1.3; 1.1.1.2.1; 1.1.1.2.2; 1.1.1.2.3; 1.1.2.1.1; 1.1.2.1.2; 1.1.2.1.3; 1.1.2.2.1; 1.1.2.2.2; 1.1.2.2.3; 1.1.3.1.1; 1.1.3.1.2; 1.1.3.1.3; 1.1.3.2.1; 1.1.3.2.2; 1.1.3.2.3; 1.1.4.1.1; 1.1.4.1.2; 1.1.4.1.3; 1.1.4.2.1; 1.1.4.2.2; 1.1.4.2.3; 1.1.5.1.1; 1.1.5.1.2; 1.1.5.1.3; 1.1.5.2.1; 1.1.5.2.2; 1.1.5.2.3; 1.1.6.1.1; 1.1.6.1.2; 1.1.6.1.3; 1.1.6.2.1; 1.1.6.2.2; 1.1.6.2.3; 1.2.1.1.1; 1.2.1.1.2; 1.2.1.1.3; 1.2.1.2.1; 1.2.1.2.2; 1.2.1.2.3; 1.2.2.1.1; 1.2.2.1.2; 1.2.2.1.3; 1.2.2.2.1; 1.2.2.2.2; 1.2.2.2.3; 1.2.3.1.1; 1.2.3.1.2; 1.2.3.1.3; 1.2.3.2.1; 1.2.3.2.2; 1.2.3.2.3; 1.2.4.1.1; 1.2.4.1.2; 1.2.4.1.3; 1.2.4.2.1; 1.2.4.2.2; 1.2.4.2.3; 1.2.5.1.1; 1.2.5.1.2; 1.2.5.1.3; 1.2.5.2.1; 1.2.5.2.2; 1.2.5.2.3; 1.2.6.1.1; 1.2.6.1.2; 1.2.6.1.3; 1.2.6.2.1; 1.2.6.2.2; 1.2.6.2.3; 1.3.1.1.1; 1.3.1.1.2; 1.3.1.1.3; 1.3.1.2.1; 1.3.1.2.2; 1.3.1.2.3; 1.3.2.1.1; 1.3.2.1.2; 1.3.2.1.3; 1.3.2.2.1; 1.3.2.2.2; 1.3.2.2.3; 1.3.3.1.1; 1.3.3.1.2; 1.3.3.1.3; 1.3.3.2.1; 1.3.3.2.2; 1.3.3.2.3; 1.3.4.1.1; 1.3.4.1.2; 1.3.4.1.3; 1.3.4.2.1; 1.3.4.2.2; 1.3.4.2.3; 1.3.5.1.1; 1.3.5.1.2; 1.3.5.1.3; 1.3.5.2.1; 1.3.5.2.2; 1.3.5.2.3; 1.3.6.1.1; 1.3.6.1.2; 1.3.6.1.3; 1.3.6.2.1; 1.3.6.2.2; 1.3.6.2.3; 1.4.1.1.1; 1.4.1.1.2; 1.4.1.1.3; 1.4.1.2.1; 1.4.1.2.2; 1.4.1.2.3; 1.4.2.1.1; 1.4.2.1.2; 1.4.2.1.3; 1.4.2.2.1; 1.4.2.2.2; 1.4.2.2.3; 1.4.3.1.1; 1.4.3.1.2; 1.4.3.1.3; 1.4.3.2.1; 1.4.3.2.2; 1.4.3.2.3; 1.4.4.1.1; 1.4.4.1.2; 1.4.4.1.3; 1.4.4.2.1; 1.4.4.2.2; 1.4.4.2.3; 1.4.5.1.1; 1.4.5.1.2; 1.4.5.1.3; 1.4.5.2.1; 1.4.5.2.2; 1.4.5.2.3; 1.4.6.1.1; 1.4.6.1.2; 1.4.6.1.3; 1.4.6.2.1; 1.4.6.2.2; 1.4.6.2.3; 1.5.1.1.1; 1.5.1.1.2; 1.5.1.1.3; 1.5.1.2.1; 1.5.1.2.2; 1.5.1.2.3; 1.5.2.1.1; 1.5.2.1.2; 1.5.2.1.3; 1.5.2.2.1; 1.5.2.2.2; 1.5.2.2.3; 1.5.3.1.1; 1.5.3.1.2; 1.5.3.1.3; 1.5.3.2.1; 1.5.3.2.2; 1.5.3.2.3; 1.5.4.1.1; 1.5.4.1.2; 1.5.4.1.3; 1.5.4.2.1; 1.5.4.2.2; 1.5.4.2.3; 1.5.5.1.1; 1.5.5.1.2; 1.5.5.1.3; 1.5.5.2.1; 1.5.5.2.2; 1.5.5.2.3; 1.5.6.1.1; 1.5.6.1.2; 1.5.6.1.3; 1.5.6.2.1; 1.5.6.2.2; 1.5.6.2.3; 1.6.1.1.1; 1.6.1.1.2; 1.6.1.1.3; 1.6.1.2.1; 1.6.1.2.2; 1.6.1.2.3; 1.6.2.1.1; 1.6.2.1.2; 1.6.2.1.3; 1.6.2.2.1; 1.6.2.2.2; 1.6.2.2.3; 1.6.3.1.1; 1.6.3.1.2; 1.6.3.1.3; 1.6.3.2.1; 1.6.3.2.2; 1.6.3.2.3; 1.6.4.1.1; 1.6.4.1.2; 1.6.4.1.3; 1.6.4.2.1; 1.6.4.2.2; 1.6.4.2.3; 1.6.5.1.1; 1.6.5.1.2; 1.6.5.1.3; 1.6.5.2.1; 1.6.5.2.2; 1.6.5.2.3; 1.6.6.1.1; 1.6.6.1.2; 1.6.6.1.3; 1.6.6.2.1; 1.6.6.2.2; 1.6.6.2.3; 1.7.1.1.1; 1.7.1.1.2; 1.7.1.1.3; 1.7.1.2.1; 1.7.1.2.2; 1.7.1.2.3; 1.7.2.1.1; 1.7.2.1.2; 1.7.2.1.3; 1.7.2.2.1; 1.7.2.2.2; 1.7.2.2.3; 1.7.3.1.1; 1.7.3.1.2; 1.7.3.1.3; 1.7.3.2.1; 1.7.3.2.2; 1.7.3.2.3; 1.7.4.1.1; 1.7.4.1.2; 1.7.4.1.3; 1.7.4.2.1; 1.7.4.2.2; 1.7.4.2.3; 1.7.5.1.1; 1.7.5.1.2; 1.7.5.1.3; 1.7.5.2.1; 1.7.5.2.2; 1.7.5.2.3; 1.7.6.1.1; 1.7.6.1.2; 1.7.6.1.3; 1.7.6.2.1; 1.7.6.2.2; 1.7.6.2.3.
Embodiments of Formula 2
2.1.1.1.1.1; 2.1.1.1.1.2; 2.1.1.1.1.3; 2.1.1.1.2.1; 2.1.1.1.2.2; 2.1.1.1.2.3; 2.1.1.2.1.1; 2.1.1.2.1.2; 2.1.1.2.1.3; 2.1.1.2.2.1; 2.1.1.2.2.2; 2.1.1.2.2.3; 2.1.2.1.1.1; 2.1.2.1.1.2; 2.1.2.1.1.3; 2.1.2.1.2.1; 2.1.2.1.2.2; 2.1.2.1.2.3; 2.1.2.2.1.1; 2.1.2.2.1.2; 2.1.2.2.1.3; 2.1.2.2.2.1; 2.1.2.2.2.2; 2.1.2.2.2.3; 2.1.3.1.1.1; 2.1.3.1.1.2; 2.1.3.1.1.3; 2.1.3.1.2.1; 2.1.3.1.2.2; 2.1.3.1.2.3; 2.1.3.2.1.1; 2.1.3.2.1.2; 2.1.3.2.1.3; 2.1.3.2.2.1; 2.1.3.2.2.2; 2.1.3.2.2.3; 2.1.4.1.1.1; 2.1.4.1.1.2; 2.1.4.1.1.3; 2.1.4.1.2.1; 2.1.4.1.2.2; 2.1.4.1.2.3; 2.1.4.2.1.1; 2.1.4.2.1.2; 2.1.4.2.1.3; 2.1.4.2.2.1; 2.1.4.2.2.2; 2.1.4.2.2.3; 2.1.5.1.1.1; 2.1.5.1.1.2; 2.1.5.1.1.3; 2.1.5.1.2.1; 2.1.5.1.2.2; 2.1.5.1.2.3; 2.1.5.2.1.1; 2.1.5.2.1.2; 2.1.5.2.1.3; 2.1.5.2.2.1; 2.1.5.2.2.2; 2.1.5.2.2.3; 2.1.6.1.1.1; 2.1.6.1.1.2; 2.1.6.1.1.3;

TABLE 7-continued

Selected Embodiments of the Invention 2.1.6.1.2.1; 2.1.6.1.2.2; 2.1.6.1.2.3; 2.1.6.2.1.1; 2.1.6.2.1.2; 2.1.6.2.1.3; 2.1.6.2.2.1;
2.1.6.2.2.2; 2.1.6.2.2.3; 2.2.1.1.1.1; 2.2.1.1.1.2; 2.2.1.1.1.3; 2.2.1.1.2.1; 2.2.1.1.2.2;
2.2.1.1.2.3; 2.2.1.2.1.1; 2.2.1.2.1.2; 2.2.1.2.1.3; 2.2.1.2.2.1; 2.2.1.2.2.2; 2.2.1.2.2.3;
2.2.2.1.1.1; 2.2.2.1.1.2; 2.2.2.1.1.3; 2.2.2.1.2.1; 2.2.2.1.2.2; 2.2.2.1.2.3; 2.2.2.2.1.1;
2.2.2.2.1.2; 2.2.2.2.1.3; 2.2.2.2.2.1; 2.2.2.2.2.2; 2.2.2.2.2.3; 2.2.3.1.1.1; 2.2.3.1.1.2;
2.2.3.1.1.3; 2.2.3.1.2.1; 2.2.3.1.2.2; 2.2.3.1.2.3; 2.2.3.2.1.1; 2.2.3.2.1.2; 2.2.3.2.1.3;
2.2.3.2.2.1; 2.2.3.2.2.2; 2.2.3.2.2.3; 2.2.4.1.1.1; 2.2.4.1.1.2; 2.2.4.1.1.3; 2.2.4.1.2.1;
2.2.4.1.2.2; 2.2.4.1.2.3; 2.2.4.2.1.1; 2.2.4.2.1.2; 2.2.4.2.1.3; 2.2.4.2.2.1; 2.2.4.2.2.2;
2.2.4.2.2.3; 2.2.5.1.1.1; 2.2.5.1.1.2; 2.2.5.1.1.3; 2.2.5.1.2.1; 2.2.5.1.2.2; 2.2.5.1.2.3;
2.2.5.2.1.1; 2.2.5.2.1.2; 2.2.5.2.1.3; 2.2.5.2.2.1; 2.2.5.2.2.2; 2.2.5.2.2.3; 2.2.6.1.1.1;
2.2.6.1.1.2; 2.2.6.1.1.3; 2.2.6.1.2.1; 2.2.6.1.2.2; 2.2.6.1.2.3; 2.2.6.2.1.1; 2.2.6.2.1.2;
2.2.6.2.1.3; 2.2.6.2.2.1; 2.2.6.2.2.2; 2.2.6.2.2.3; 2.3.1.1.1.1; 2.3.1.1.1.2; 2.3.1.1.1.3;
2.3.1.1.2.1; 2.3.1.1.2.2; 2.3.1.1.2.3; 2.3.1.2.1.1; 2.3.1.2.1.2; 2.3.1.2.1.3; 2.3.1.2.2.1;
2.3.1.2.2.2; 2.3.1.2.2.3; 2.3.2.1.1.1; 2.3.2.1.1.2; 2.3.2.1.1.3; 2.3.2.1.2.1; 2.3.2.1.2.2;
2.3.2.1.2.3; 2.3.2.2.1.1; 2.3.2.2.1.2; 2.3.2.2.1.3; 2.3.2.2.2.1; 2.3.2.2.2.2; 2.3.2.2.2.3;
2.3.3.1.1.1; 2.3.3.1.1.2; 2.3.3.1.1.3; 2.3.3.1.2.1; 2.3.3.1.2.2; 2.3.3.1.2.3; 2.3.3.2.1.1;
2.3.3.2.1.2; 2.3.3.2.1.3; 2.3.3.2.2.1; 2.3.3.2.2.2; 2.3.3.2.2.3; 2.3.4.1.1.1; 2.3.4.1.1.2;
2.3.4.1.1.3; 2.3.4.1.2.1; 2.3.4.1.2.2; 2.3.4.1.2.3; 2.3.4.2.1.1; 2.3.4.2.1.2; 2.3.4.2.1.3;
2.3.4.2.2.1; 2.3.4.2.2.2; 2.3.4.2.2.3; 2.3.5.1.1.1; 2.3.5.1.1.2; 2.3.5.1.1.3; 2.3.5.1.2.1;
2.3.5.1.2.2; 2.3.5.1.2.3; 2.3.5.2.1.1; 2.3.5.2.1.2; 2.3.5.2.1.3; 2.3.5.2.2.1; 2.3.5.2.2.2;
2.3.5.2.2.3; 2.3.6.1.1.1; 2.3.6.1.1.2; 2.3.6.1.1.3; 2.3.6.1.2.1; 2.3.6.1.2.2; 2.3.6.1.2.3;
2.3.6.2.1.1; 2.3.6.2.1.2; 2.3.6.2.1.3; 2.3.6.2.2.1; 2.3.6.2.2.2; 2.3.6.2.2.3; 2.4.1.1.1.1;
2.4.1.1.1.2; 2.4.1.1.1.3; 2.4.1.1.2.1; 2.4.1.1.2.2; 2.4.1.1.2.3; 2.4.1.2.1.1; 2.4.1.2.1.2;
2.4.1.2.1.3; 2.4.1.2.2.1; 2.4.1.2.2.2; 2.4.1.2.2.3; 2.4.2.1.1.1; 2.4.2.1.1.2; 2.4.2.1.1.3;
2.4.2.1.2.1; 2.4.2.1.2.2; 2.4.2.1.2.3; 2.4.2.2.1.1; 2.4.2.2.1.2; 2.4.2.2.1.3; 2.4.2.2.2.1;
2.4.2.2.2.2; 2.4.2.2.2.3; 2.4.3.1.1.1; 2.4.3.1.1.2; 2.4.3.1.1.3; 2.4.3.1.2.1; 2.4.3.1.2.2;
2.4.3.1.2.3; 2.4.3.2.1.1; 2.4.3.2.1.2; 2.4.3.2.1.3; 2.4.3.2.2.1; 2.4.3.2.2.2; 2.4.3.2.2.3;
2.4.4.1.1.1; 2.4.4.1.1.2; 2.4.4.1.1.3; 2.4.4.1.2.1; 2.4.4.1.2.2; 2.4.4.1.2.3; 2.4.4.2.1.1;
2.4.4.2.1.2; 2.4.4.2.1.3; 2.4.4.2.2.1; 2.4.4.2.2.2; 2.4.4.2.2.3; 2.4.5.1.1.1; 2.4.5.1.1.2;
2.4.5.1.1.3; 2.4.5.1.2.1; 2.4.5.1.2.2; 2.4.5.1.2.3; 2.4.5.2.1.1; 2.4.5.2.1.2; 2.4.5.2.1.3;
2.4.5.2.2.1; 2.4.5.2.2.2; 2.4.5.2.2.3; 2.4.6.1.1.1; 2.4.6.1.1.2; 2.4.6.1.1.3; 2.4.6.1.2.1;
2.4.6.1.2.2; 2.4.6.1.2.3; 2.4.6.2.1.1; 2.4.6.2.1.2; 2.4.6.2.1.3; 2.4.6.2.2.1; 2.4.6.2.2.2;
2.4.6.2.2.3; 2.5.1.1.1.1; 2.5.1.1.1.2; 2.5.1.1.1.3; 2.5.1.1.2.1; 2.5.1.1.2.2; 2.5.1.1.2.3;
2.5.1.2.1.1; 2.5.1.2.1.2; 2.5.1.2.1.3; 2.5.1.2.2.1; 2.5.1.2.2.2; 2.5.1.2.2.3; 2.5.2.1.1.1;
2.5.2.1.1.2; 2.5.2.1.1.3; 2.5.2.1.2.1; 2.5.2.1.2.2; 2.5.2.1.2.3; 2.5.2.2.1.1; 2.5.2.2.1.2;
2.5.2.2.1.3; 2.5.2.2.2.1; 2.5.2.2.2.2; 2.5.2.2.2.3; 2.5.3.1.1.1; 2.5.3.1.1.2; 2.5.3.1.1.3;
2.5.3.1.2.1; 2.5.3.1.2.2; 2.5.3.1.2.3; 2.5.3.2.1.1; 2.5.3.2.1.2; 2.5.3.2.1.3; 2.5.3.2.2.1;
2.5.3.2.2.2; 2.5.3.2.2.3; 2.5.4.1.1.1; 2.5.4.1.1.2; 2.5.4.1.1.3; 2.5.4.1.2.1; 2.5.4.1.2.2;
2.5.4.1.2.3; 2.5.4.2.1.1; 2.5.4.2.1.2; 2.5.4.2.1.3; 2.5.4.2.2.1; 2.5.4.2.2.2; 2.5.4.2.2.3;
2.5.5.1.1.1; 2.5.5.1.1.2; 2.5.5.1.1.3; 2.5.5.1.2.1; 2.5.5.1.2.2; 2.5.5.1.2.3; 2.5.5.2.1.1;
2.5.5.2.1.2; 2.5.5.2.1.3; 2.5.5.2.2.1; 2.5.5.2.2.2; 2.5.5.2.2.3; 2.5.6.1.1.1; 2.5.6.1.1.2;
2.5.6.1.1.3; 2.5.6.1.2.1; 2.5.6.1.2.2; 2.5.6.1.2.3; 2.5.6.2.1.1; 2.5.6.2.1.2; 2.5.6.2.1.3;
2.5.6.2.2.1; 2.5.6.2.2.2; 2.5.6.2.2.3; 2.6.1.1.1.1; 2.6.1.1.1.2; 2.6.1.1.1.3; 2.6.1.1.2.1;
2.6.1.1.2.2; 2.6.1.1.2.3; 2.6.1.2.1.1; 2.6.1.2.1.2; 2.6.1.2.1.3; 2.6.1.2.2.1; 2.6.1.2.2.2;
2.6.1.2.2.3; 2.6.2.1.1.1; 2.6.2.1.1.2; 2.6.2.1.1.3; 2.6.2.1.2.1; 2.6.2.1.2.2; 2.6.2.1.2.3;
2.6.2.2.1.1; 2.6.2.2.1.2; 2.6.2.2.1.3; 2.6.2.2.2.1; 2.6.2.2.2.2; 2.6.2.2.2.3; 2.6.3.1.1.1;
2.6.3.1.1.2; 2.6.3.1.1.3; 2.6.3.1.2.1; 2.6.3.1.2.2; 2.6.3.1.2.3; 2.6.3.2.1.1; 2.6.3.2.1.2;
2.6.3.2.1.3; 2.6.3.2.2.1; 2.6.3.2.2.2; 2.6.3.2.2.3; 2.6.4.1.1.1; 2.6.4.1.1.2; 2.6.4.1.1.3;
2.6.4.1.2.1; 2.6.4.1.2.2; 2.6.4.1.2.3; 2.6.4.2.1.1; 2.6.4.2.1.2; 2.6.4.2.1.3; 2.6.4.2.2.1;
2.6.4.2.2.2; 2.6.4.2.2.3; 2.6.5.1.1.1; 2.6.5.1.1.2; 2.6.5.1.1.3; 2.6.5.1.2.1; 2.6.5.1.2.2;
2.6.5.1.2.3; 2.6.5.2.1.1; 2.6.5.2.1.2; 2.6.5.2.1.3; 2.6.5.2.2.1; 2.6.5.2.2.2; 2.6.5.2.2.3;
2.6.6.1.1.1; 2.6.6.1.1.2; 2.6.6.1.1.3; 2.6.6.1.2.1; 2.6.6.1.2.2; 2.6.6.1.2.3; 2.6.6.2.1.1;
2.6.6.2.1.2; 2.6.6.2.1.3; 2.6.6.2.2.1; 2.6.6.2.2.2; 2.6.6.2.2.3; 2.7.1.1.1.1; 2.7.1.1.1.2;
2.7.1.1.1.3; 2.7.1.1.2.1; 2.7.1.1.2.2; 2.7.1.1.2.3; 2.7.1.2.1.1; 2.7.1.2.1.2; 2.7.1.2.1.3;
2.7.1.2.2.1; 2.7.1.2.2.2; 2.7.1.2.2.3; 2.7.2.1.1.1; 2.7.2.1.1.2; 2.7.2.1.1.3; 2.7.2.1.2.1;
2.7.2.1.2.2; 2.7.2.1.2.3; 2.7.2.2.1.1; 2.7.2.2.1.2; 2.7.2.2.1.3; 2.7.2.2.2.1; 2.7.2.2.2.2;
2.7.2.2.2.3; 2.7.3.1.1.1; 2.7.3.1.1.2; 2.7.3.1.1.3; 2.7.3.1.2.1; 2.7.3.1.2.2; 2.7.3.1.2.3;
2.7.3.2.1.1; 2.7.3.2.1.2; 2.7.3.2.1.3; 2.7.3.2.2.1; 2.7.3.2.2.2; 2.7.3.2.2.3; 2.7.4.1.1.1;
2.7.4.1.1.2; 2.7.4.1.1.3; 2.7.4.1.2.1; 2.7.4.1.2.2; 2.7.4.1.2.3; 2.7.4.2.1.1; 2.7.4.2.1.2;
2.7.4.2.1.3; 2.7.4.2.2.1; 2.7.4.2.2.2; 2.7.4.2.2.3; 2.7.5.1.1.1; 2.7.5.1.1.2; 2.7.5.1.1.3;
2.7.5.1.2.1; 2.7.5.1.2.2; 2.7.5.1.2.3; 2.7.5.2.1.1; 2.7.5.2.1.2; 2.7.5.2.1.3; 2.7.5.2.2.1;
2.7.5.2.2.2; 2.7.5.2.2.3; 2.7.6.1.1.1; 2.7.6.1.1.2; 2.7.6.1.1.3; 2.7.6.1.2.1; 2.7.6.1.2.2;
2.7.6.1.2.3; 2.7.6.2.1.1; 2.7.6.2.1.2; 2.7.6.2.1.3; 2.7.6.2.2.1; 2.7.6.2.2.2; 2.7.6.2.2.3.

General Methods and Materials for the Preparation of the Compounds of the Invention Synthetic Methods The compounds of the formulas of this invention are prepared using a series of chemical reactions well known to those skilled in the art, altogether making up the process for preparing said compounds and exemplified further. The processes described further are only meant as examples and by no means are meant to limit the scope of the present invention.

The invention also relates to methods of making the compositions of the invention. The compositions are prepared by any of the applicable techniques of organic synthesis. Many such techniques are well known in the art. However, many of the known techniques are elaborated in "Compendium of Organic Synthetic Methods" (John Wiley & Sons, New York), Vol. 1, Ian T. Harrison and Shuyen Harrison, 1971; Vol. 2, Ian T. Harrison and Shuyen Harrison, 1974; Vol. 3, Louis S. Hegedus and Leroy Wade, 1977; Vol. 4, Leroy G. Wade, Jr., 1980; Vol. 5, Leroy G. Wade, Jr., 1984; and Vol. 6, Michael B. Smith; as well as March, J., "Advanced Organic Chemistry, Third Edition", (John Wiley & Sons, New York, 1985), "Comprehensive Organic Synthesis. Selectivity, Strategy & Efficiency in Modern Organic Chemistry. In 9 Volumes", Barry M. Trost, Editor-in-Chief (Pergamon Press, New York, 1993 printing).

Exemplary methods for the preparation of the compositions of the invention are provided below. These methods are intended to illustrate the nature of such preparations, and are not intended to limit the scope of applicable methods.

Generally, the reaction conditions such as temperature, reaction time, solvents, workup procedures, and the like, will be those common in the art for the particular reaction to be performed. The cited reference material, together with material cited therein, contains detailed descriptions of such conditions. Typically the temperatures will be −100° C. to 200° C., solvents will be aprotic or protic, and reaction times will be 10 seconds to 10 days. Workup typically consists of quenching any unreacted reagents followed by partition between a water/organic layer system (extraction) and separating the layer containing the product.

Oxidation and reduction reactions are typically carried out at temperatures near room temperature (about 20° C.), although for metal hydride reductions frequently the temperature is reduced to 0° C. to −100° C., solvents are typically aprotic for reductions and may be either protic or aprotic for oxidations. Reaction times are adjusted to achieve desired conversions.

Condensation reactions are typically carried out at temperatures near room temperature, although for non-equilibrating, kinetically controlled condensations reduced temperatures (0° C. to −100° C.) are also common. Solvents can be either protic (common in equilibrating reactions) or aprotic (common in kinetically controlled reactions).

Standard synthetic techniques such as azeotropic removal of reaction by-products and use of anhydrous reaction conditions (e.g. inert gas environments) are common in the art and will be applied when applicable.

General aspects of these exemplary methods are described below. Each of the products of the following processes is optionally separated, isolated, and/or purified prior to its use in subsecquent processes.

The terms "treated", "treating", "treatment", and the like, mean contacting, mixing, reacting, allowing to react, bringing into contact, and other terms common in the art for indicating that one or more chemical entities is treated in such a manner as to convert it to one or more other chemical entities. This means that "treating compound one with compound two" is synonymous with "allowing compound one to react with compound two", "contacting compound one with compound two", "reacting compound one with compound two", and other expressions common in the art of organic synthesis for reasonably indicating that compound one was "treated", "reacted", "allowed to react", etc., with compound two.

"Treating" indicates the reasonable and usual manner in which organic chemicals are allowed to react. Normal concentrations (0.01M to 10M, typically 0.1M to 1M), temperatures (−100° C. to 250° C., typically −78° C. to 150° C., more typically −78° C. to 100° C., still more typically 0° C. to 100° C.), reaction vessels (typically glass, plastic, metal), solvents, pressures, atmospheres (typically air for oxygen and water insensitive reactions or nitrogen or argon for oxygen or water sensitive), etc., are intended unless otherwise indicated. The knowledge of similar reactions known in the art of organic synthesis is used in selecting the conditions and apparatus for "treating" in a given process. In particular, one of ordinary skill in the art of organic sysnthesis selects conditions and apparatus reasonably expected to successfully carry out the chemical reactions of the described processes based on the knowledge in the art.

Modification of the exemplified schemes and examples leads to various analogs of the specific exemplary materials produced above. The above citations describing suitable methods of organic synthesis are applicable to such modifications.

In the exemplary schemes it may be advantageous to separate reaction products from one another and/or from starting materials. The desired products of each step or series of steps is separated and/or purified (hereinafter separated) to the desired degree of homogeneity by the techniques common in the art. Typically such separations involve multiphase extraction, crystallization from a solvent or solvent mixture, distillation, sublimation, or chromatography. Chromatography can involve any number of methods including, for example, size exclusion or ion exchange chromatography, high, medium, or low pressure liquid chromatography, small scale and preparative thin or thick layer chromatography, as well as techniques of small scale thin layer and flash chromatography. Such separations are desireable if addition reactions place substituents at both of the pyrimidine nitrogen atoms. Separation of these isomers is well within the skill of the artisan.

Another class of separation methods involves treatment of a mixture with a reagent selected to bind to or render otherwise separable a desired product, unreacted starting material, reaction by product, or the like. Such reagents include adsorbents or absorbents such as activated carbon, molecular sieves, ion exchange media, or the like. Alternatively, the reagents can be acids in the case of a basic material, bases in the case of an acidic material, binding reagents such as antibodies, binding proteins, selective chelators such as crown ethers, liquid/liquid ion extraction reagents (LIX), or the like.

Selection of appropriate methods of separation depends on the nature of the materials involved. For example, boiling point, and molecular weight in distillation and sublimation, presence or absence of polar functional groups in chromatography, stability of materials in acidic and basic media in multiphase extraction, and the like. One skilled in the art will apply techniques most likely to achieve the desired separation.

A synthetic route to 5-benzyl-2-phenyl-5H-imidazo[4,5-d]pyrimidine and analogues is shown in Scheme A.

Scheme A:

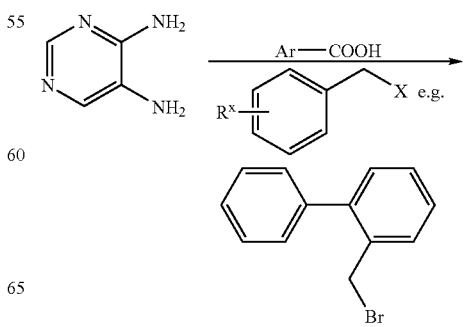

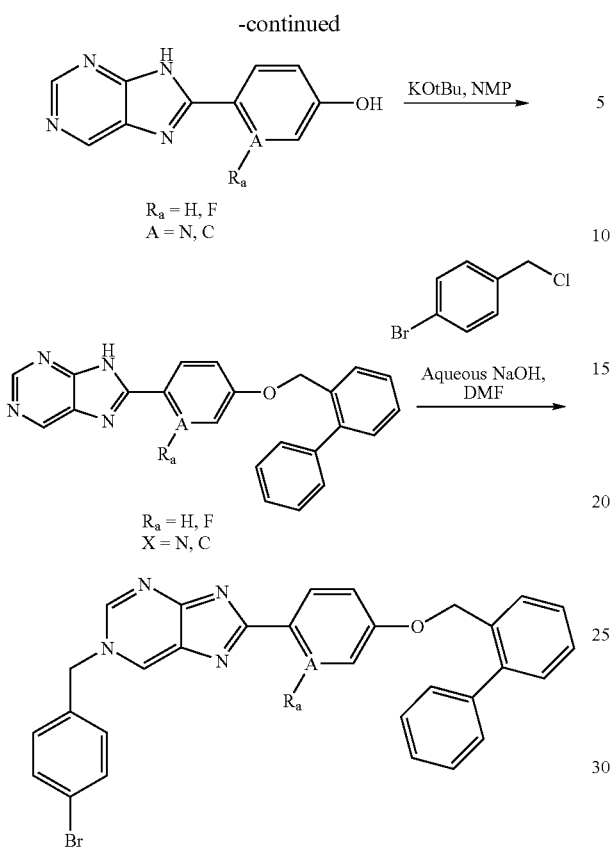

$R_a$ = H, F
A = N, C $R_a$ = H, F
X = N, C

Exemplary ArCOOH reactants are

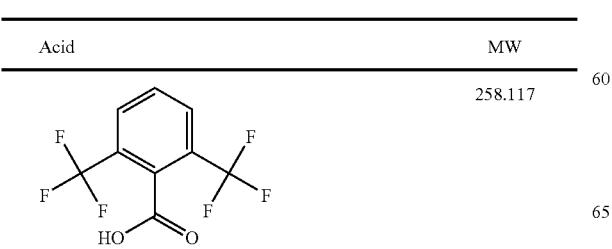

The following list includes additional carboxylic acid reactants which may be employed in the condensation, ring closure reaction of Scheme A. The compounds so produced will bear the residue of the acid at the site of $YR^1$. Optionally, the remainder of the molecule will be for example as in any of the compounds exemplified below.

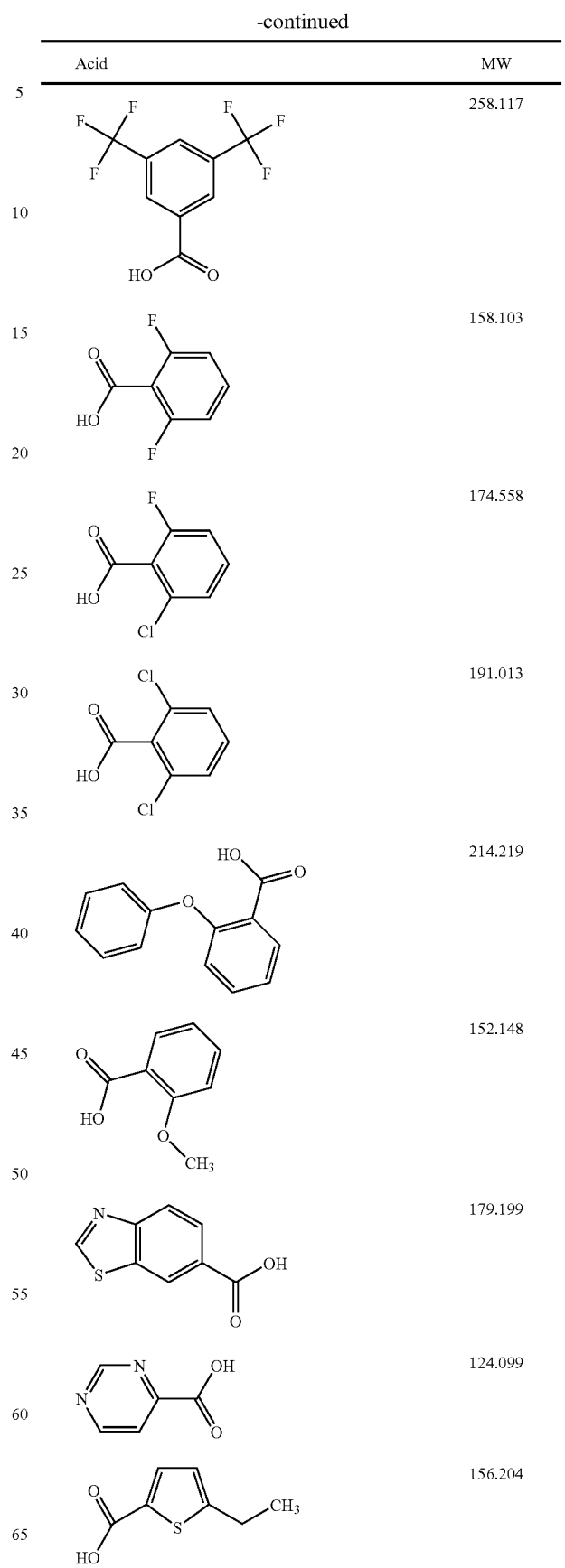

| -continued | |
|---|---|
| Acid | MW |
| 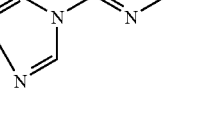 | 189.173 |
| 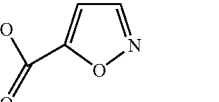 | 113.072 |
| 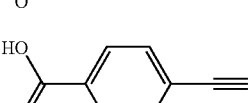 | 146.144 |
| 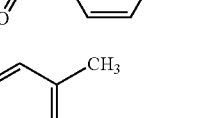 | 137.137 |
| 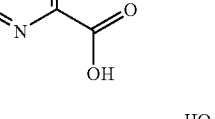 | 244.22 |
| 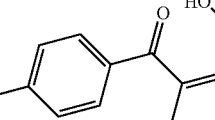 | 164.159 |
| 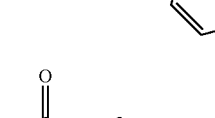 | 190.12 |
| 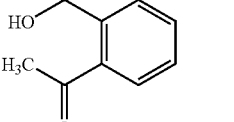 | 191.013 |
| 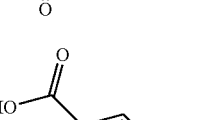 | 165.191 |
| -continued | |
|---|---|
| Acid | MW |
|  | 214.219 |
| 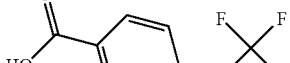 | 206.118 |
| 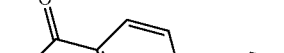 | 194.229 |
| 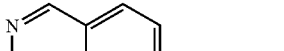 | 174.158 |
| 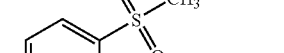 | 200.213 |
|  | 200.213 |
| 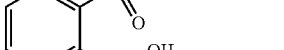 | 252.272 |
|  | 250.256 |

-continued

| Acid | MW |
|---|---|
| 2'-fluoro-biphenyl-4-carboxylic acid | 216.21 |
| 4'-fluoro-biphenyl-3-carboxylic acid | 216.21 |
| 4'-bromo-biphenyl-4-carboxylic acid | 277.116 |
| 4-acetylbenzoic acid | 164.159 |
| 4-tert-butylbenzoic acid | 178.23 |
| 1-methyl-1H-pyrrole-2-carboxylic acid | 125.126 |
| furan-2-carboxylic acid | 112.084 |
| thiophene-3-carboxylic acid | 128.151 |
| pyrazine-2-carboxylic acid | 124.099 |
| 4-(methylsulfonyl)benzoic acid | 200.213 |
| 2-fluoro-4-(trifluoromethyl)benzoic acid | 201.201 |
| 1H-pyrazole-4-carboxylic acid | 112.088 |

-continued

| Acid | MW |
|---|---|
| 4-(2,5-dimethyl-1H-pyrrol-1-yl)benzoic acid | 215.251 |
| 3-(2,5-dimethyl-1H-pyrrol-1-yl)benzoic acid | 215.251 |
| 1-methyl-1H-pyrazole-5-carboxylic acid | 126.114 |
| thiazole-4-carboxylic acid | 129.139 |
| 4-methylthiazole-5-carboxylic acid | 143.165 |
| pyrimidine-5-carboxylic acid | 124.099 |
| 5-methylisoxazole-4-carboxylic acid | 127.099 |
| 1-methyl-1H-imidazole-5-carboxylic acid | 126.114 |
| 5-(4-fluorophenyl)thiophene-2-carboxylic acid | 222.238 |
| pyridazine-4-carboxylic acid | 124.099 |

-continued

| Acid | MW |
|---|---|
| quinoxaline-2-carboxylic acid | 174.158 |
| 2-(4-methylbenzoyl)benzoic acid | 240.257 |
| 2-methoxy-4-methylbenzoic acid | 166.175 |
| 6-methylpyridine-2-carboxylic acid | 137.137 |
| 4-cyclohexylbenzoic acid | 204.267 |
| 2-fluoronicotinic acid | 141.101 |
| pyrido[2,3-b]pyrazine-6-carboxylic acid | 174.158 |
| 2,5-dimethyl-1-(pyridin-4-ylmethyl)-1H-pyrrole-3-carboxylic acid | 230.266 |

-continued

| Acid | MW |
|---|---|
| 2,5-dimethyl-1-(thiophen-2-yl)-1H-pyrrole-3-carboxylic acid | 221.279 |
| 5-bromobenzo[b]thiophene-2-carboxylic acid | 257.107 |
| 3-(2-chlorophenyl)isoxazole-5-carboxylic acid | 223.614 |
| 1-ethyl-1H-pyrazole-3-carboxylic acid | 140.141 |
| 3-oxo-2,3-dihydro-1H-indene-5-carboxylic acid | 176.17 |
| 2-fluoro-3-methylbenzoic acid | 154.139 |
| quinoline-7-carboxylic acid | 173.17 |
| quinoline-8-carboxylic acid | 173.17 |
| benzo[b]thiophene-2-carboxylic acid | 178.21 |
| 2-(1H-pyrrol-1-yl)benzoic acid | 187.197 |

| Acid | MW |
|---|---|
| (isoquinoline-3-carboxylic acid) | 173.17 |
| (3-fluoro-2-methylbenzoic acid) | 154.139 |
| (2,4-difluoro-3-methoxybenzoic acid) | 188.128 |
| (2-(3,5-difluorobenzoyl)benzoic acid) | 262.21 |
| (3-(1H-pyrrol-1-yl)benzoic acid) | 187.197 |
| (5-(1H-pyrrol-1-yl)-1,2,4-triazole-3-carboxylic acid) | 178.15 |
| (2-(prop-2-yn-1-yloxy)benzoic acid) | 176.17 |
| (3-chloroisonicotinic acid) | 157.556 |

| Acid | MW |
|---|---|
| (3',4'-difluorobiphenyl-3-carboxylic acid) | 234.2 |
| (1H-pyrazole-3-carboxylic acid) | 112.088 |
| (5-methoxybenzofuran-2-carboxylic acid) | 192.169 |
| (4-(1H-pyrrol-1-yl)benzoic acid) | 187.197 |
| (2-fluoro-3-methoxybenzoic acid) | 170.138 |

The following list includes alkylating reagents which may be employed in the pyridyl alkylation reaction of Scheme A. Here, the residue of the alkylating agent is located at the X R³ site of the compound of this invention. Optionally, the remainder of the compound will be as found in any of the compounds of examples.

| Alkylating reagent | MW |
|---|---|
| (2,4-dichlorobenzyl chloride) | 195.475 |

-continued
| Alkylating reagent | MW |
|---|---|
| 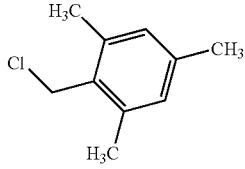 | 168.666 |
| 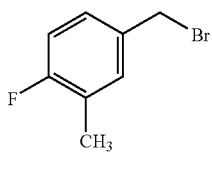 | 203.053 |
| 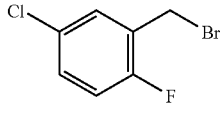 | 223.471 |
| 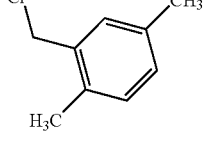 | 154.639 |
| 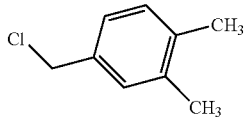 | 154.639 |
| 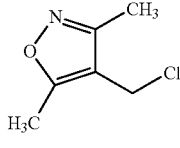 | 145.588 |
| 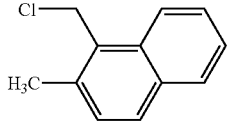 | 190.672 |
| 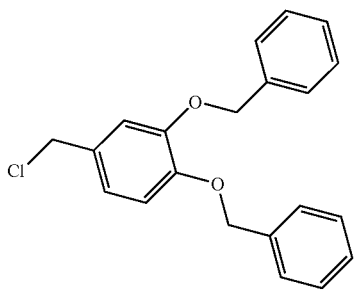 | 338.832 |
| 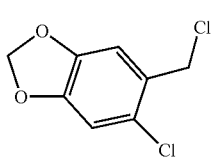 | 205.039 |
-continued
| Alkylating reagent | MW |
|---|---|
| 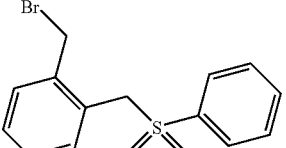 | 325.225 |
| 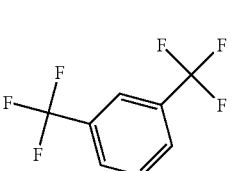 | 262.579 |
| 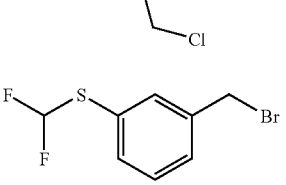 | 253.109 |
| 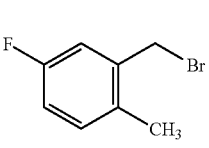 | 203.053 |
| 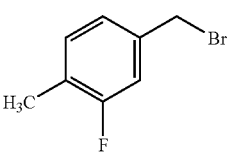 | 203.053 |
| 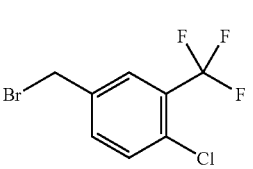 | 273.478 |
| 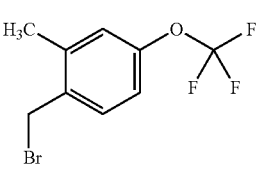 | 269.059 |
| 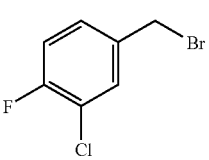 | 223.471 |
| 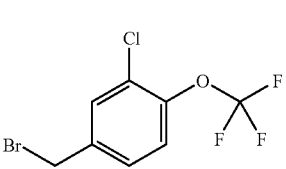 | 289.478 |

-continued
| Alkylating reagent | MW |
|---|---|
| 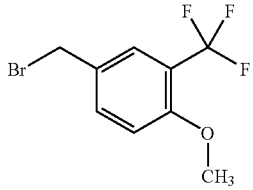 | 269.059 |
| 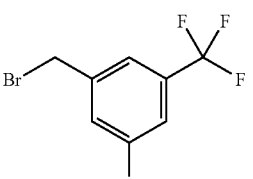 | 228.721 |
| 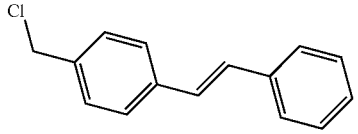 | 207.016 |
| 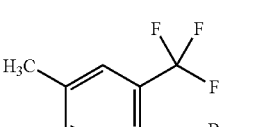 | 307.03 |
| 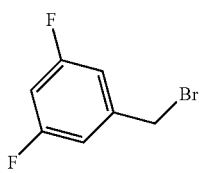 | 199.09 |
| 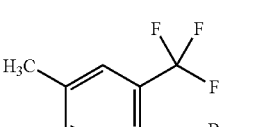 | 175.057 |
| 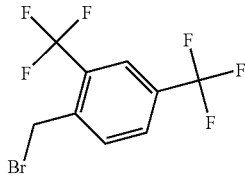 | 154.639 |
| 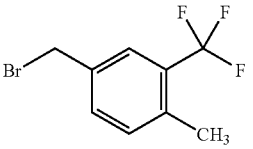 | 216.663 |
| 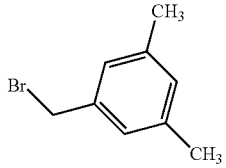 | 218.682 |
-continued
| Alkylating reagent | MW |
|---|---|
| 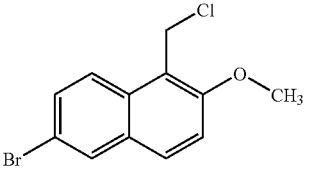 | 253.06 |
| 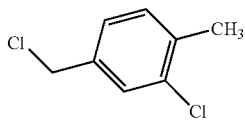 | 253.06 |
| 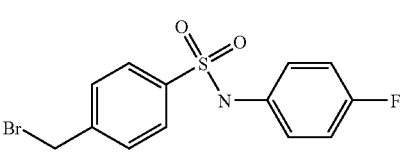 | 253.06 |
|  | 221.043 |
| 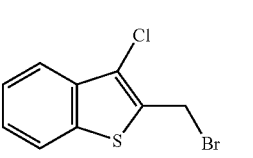 | 285.567 |
| 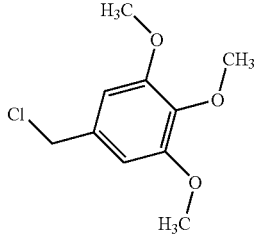 | 344.203 |
| 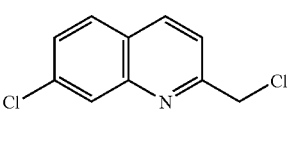 | 261.569 |
| 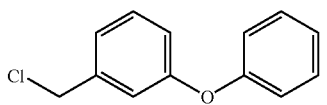 | 212.078 |
| 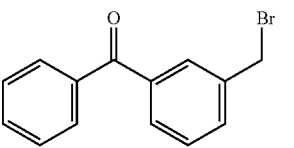 | 275.144 |

-continued
| Alkylating reagent | MW |
|---|---|
| 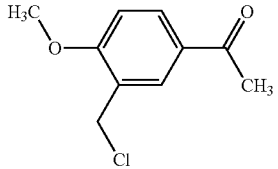 | 198.648 |
| 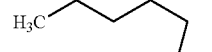 | 294.907 |
| 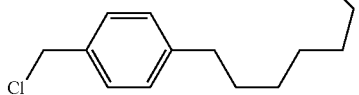 | 244.144 |
| 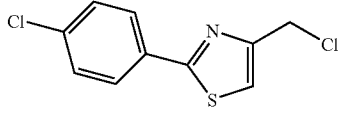 | 222.084 |
| 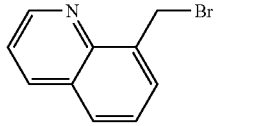 | 152.623 |
| 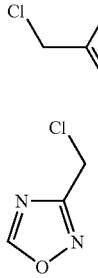 | 118.523 |
| 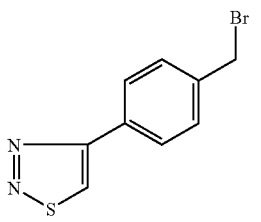 | 255.138 |
|  | 195.57 |
| 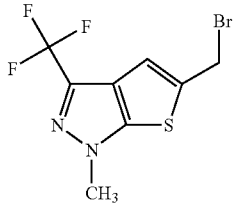 | 299.113 |
-continued
| Alkylating reagent | MW |
|---|---|
| 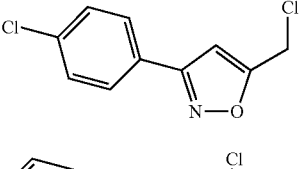 | 228.077 |
| 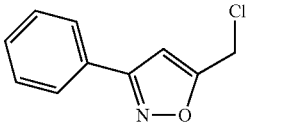 | 193.632 |
| 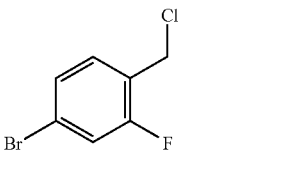 | 223.471 |
| 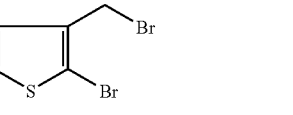 | 255.961 |
| 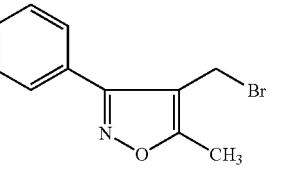 | 252.11 |
| 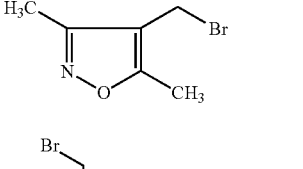 | 190.039 |
| 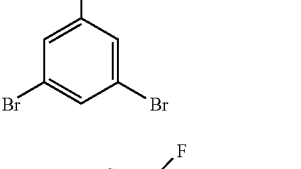 | 328.828 |
| 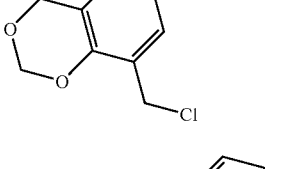 | 202.611 |
| 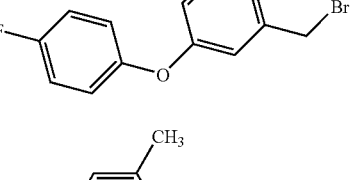 | 281.123 |
| 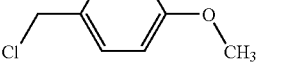 | 170.638 |

-continued
| Alkylating reagent | MW |
|---|---|
| 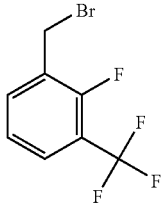 | 257.023 |
| 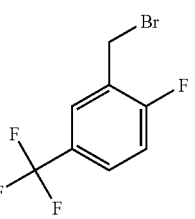 | 176.012 |
| 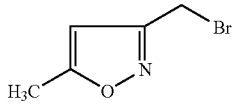 | 237.099 |
| 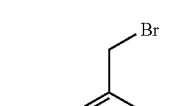 | 238.087 |
| 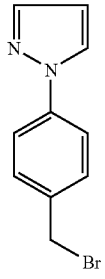 | 239.623 |
| 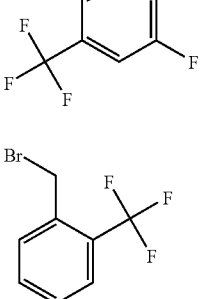 | 198.648 |
| 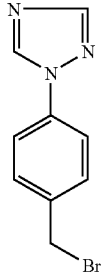 | 257.023 |
-continued
| Alkylating reagent | MW |
|---|---|
| 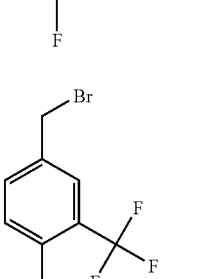 | 257.023 |
| 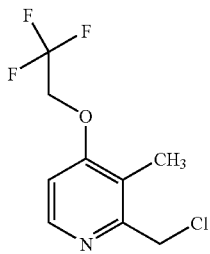 | 257.023 |
| 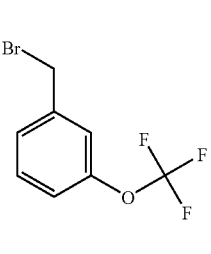 | 257.023 |
| 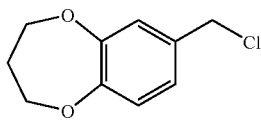 | 257.023 |
| 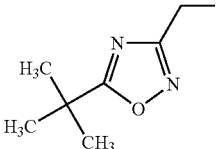 | 255.032 |
| 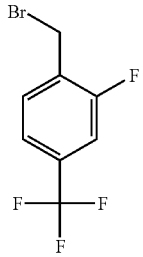 | 174.63 |
| 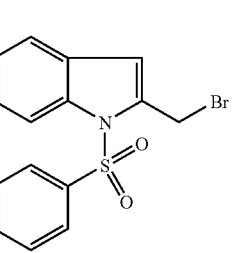 | 50.235 |

| Alkylating reagent | MW |
|---|---|
|  | 252.11 |
|  | 236.111 |
|  | 320.206 |
| 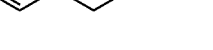 | 228.995 |
| 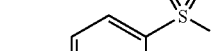 | 273.478 |
| 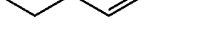 | 203.053 |
| 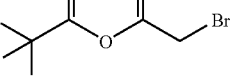 | 186.637 |
|  | 247.134 |
| Alkylating reagent | MW |
|---|---|
| 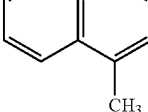 | 190.672 |
| 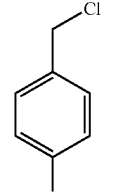 | 204.676 |
| 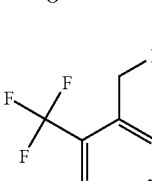 | 257.023 |
|  | 262.579 |
| 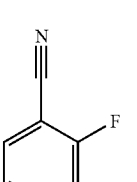 | 214.036 |
| 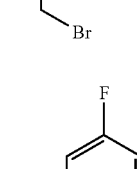 | 203.053 |
| 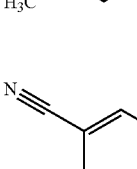 | 214.036 |

-continued
| Alkylating reagent | MW |
|---|---|
| 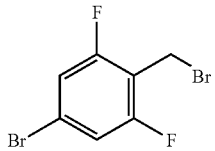 | 285.913 |
| 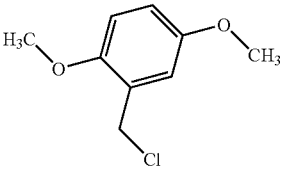 | 241.462 |
| 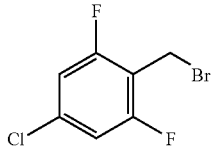 | 283.251 |
| 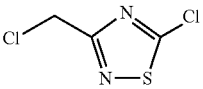 | 224.646 |
| 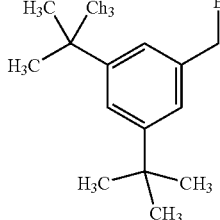 | 194.62 |
| 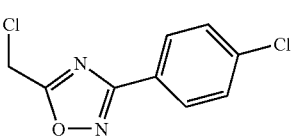 | 262.617 |
| 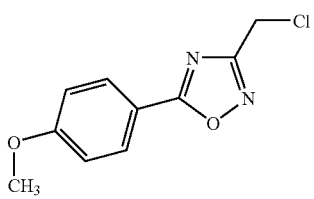 | 237.042 |
| 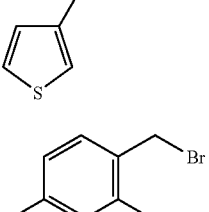 | 275.144 |
-continued
| Alkylating reagent | MW |
|---|---|
| 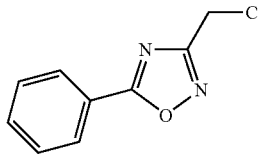 | 186.637 |
| 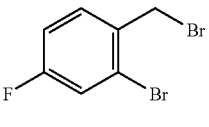 | 169.035 |
| 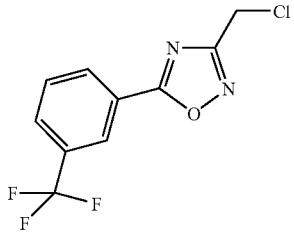 | 229.065 |
| 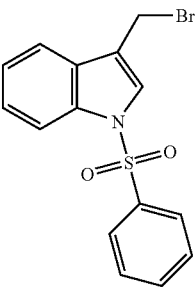 | 177.064 |
| 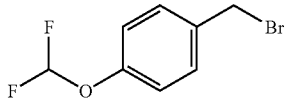 | 267.922 |
| 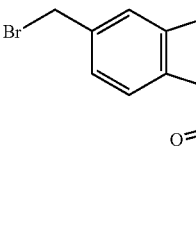 | 350.235 |
| 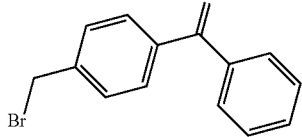 | 350.235 |
| 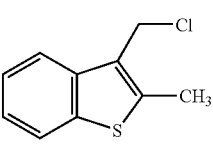 | 196.7 |
| 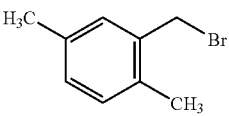 | 199.09 |

-continued
| Alkylating reagent | MW |
|---|---|
| 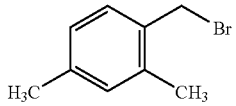 | 199.09 |
| 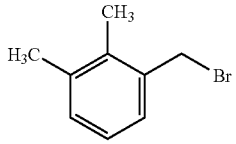 | 199.09 |
| 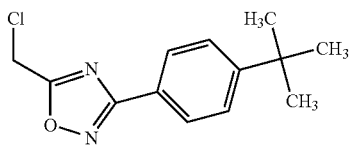 | 250.727 |
| 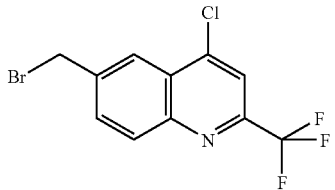 | 324.526 |
| 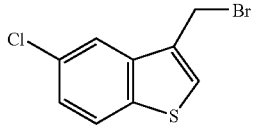 | 261.569 |
| 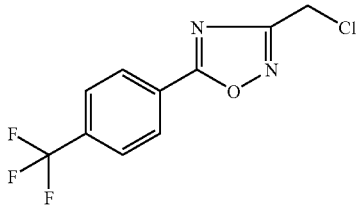 | 262.617 |
| 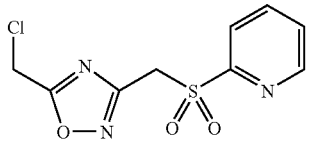 | 273.699 |
| 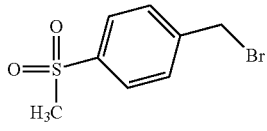 | 249.127 |
| 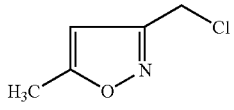 | 131.561 |
| 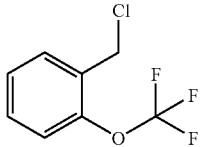 | 210.581 |
-continued
| Alkylating reagent | MW |
|---|---|
| 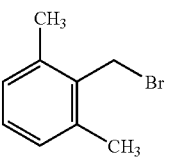 | 199.09 |
| 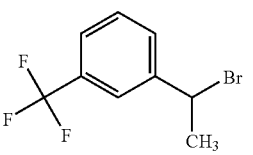 | 253.06 |
| 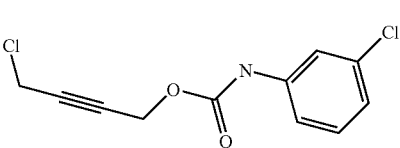 | 258.103 |
| 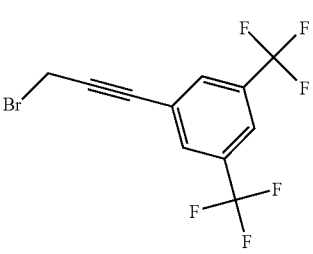 | 331.052 |
| 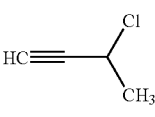 | 88.5365 |
| 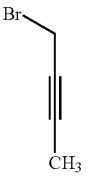 | 132.988 |
| 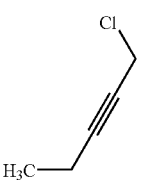 | 102.563 |
| 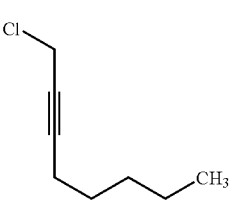 | 144.644 |

|  -continued  |  |
| --- | --- |
| Alkylating reagent | MW |
| 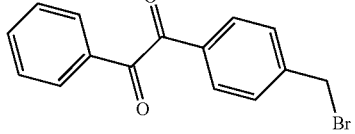 | 303.154 |
| 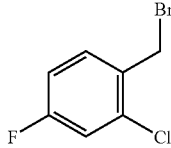 | 223.471 |
| 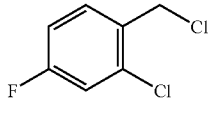 | 179.02 |
| 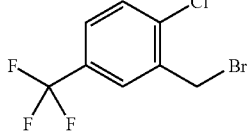 | 273.478 |
|  | 257.023 |
| 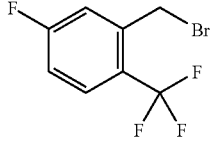 | 257.023 |
| ClH<br>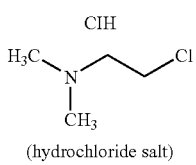<br>(hydrochloride salt) | 144.044 |
| 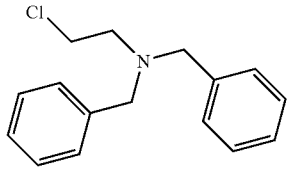 | 296.239 |
| ClH<br>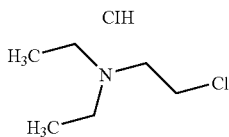 | 172.098 |
| ClH<br>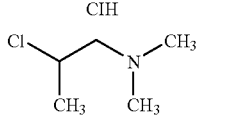 | 158.071 |
|  -continued  |  |
| --- | --- |
| Alkylating reagent | MW |
| ClH<br>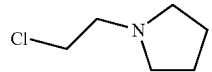 | 170.082 |
| ClH<br>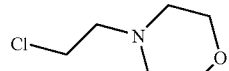 | 186.081 |
| 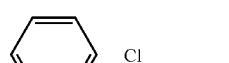 | 241.12 |
| 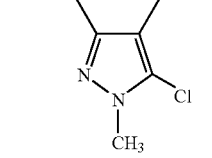 | 166.61 |
| 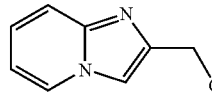 | 205.995 |
| 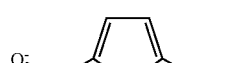 | 188.613 |
|  | 277.696 |
| 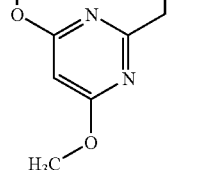 | 133.602 |
| ClH<br>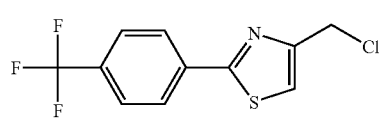 | 184.109 |
|  | 149.663 |

| Alkylating reagent | MW |
|---|---|
| 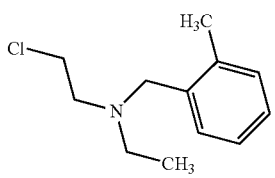 ClH | 248.195 |
| 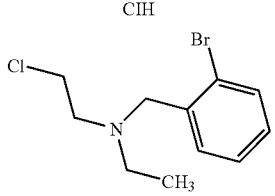 ClH | 313.064 |
| 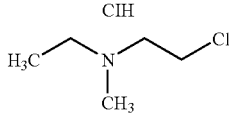 ClH | 158.071 |
| 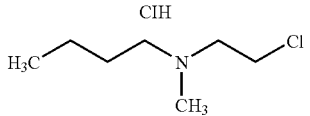 ClH | 186.124 |
| 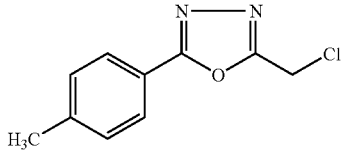 | 208.647 |
| 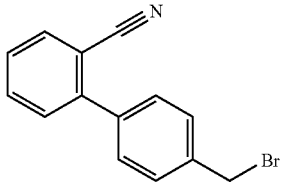 | 272.144 |
| 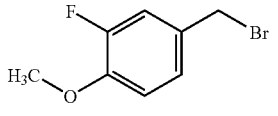 | 219.052 |
| 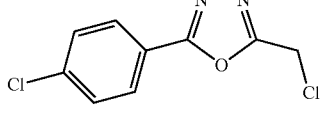 | 229.065 |
| 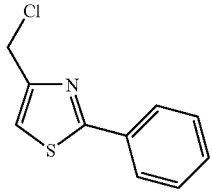 | 209.699 |
| Alkylating reagent | MW |
|---|---|
| 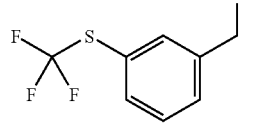 | 226.648 |
| 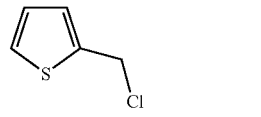 | 132.613 |
| 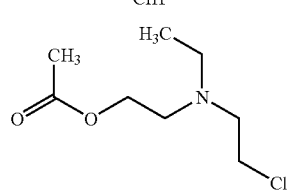 ClH | 230.133 |
| 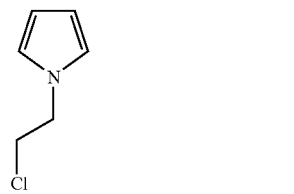 | 129.589 |
| 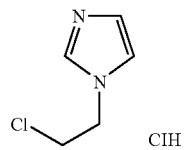 ClH | 167.038 |
| 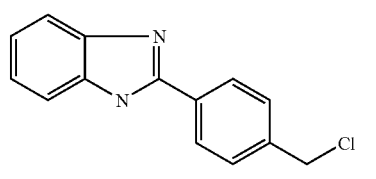 | |
| 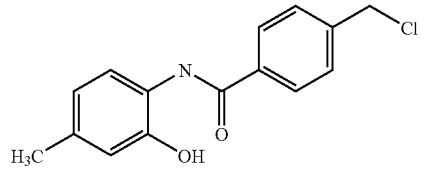 | |
| 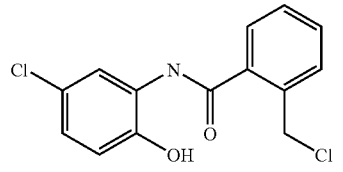 | |
| 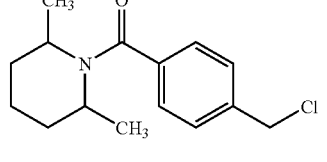 | |

-continued
| Alkylating reagent | MW |
|---|---|
| 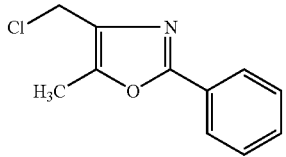 | 207.659 |
| 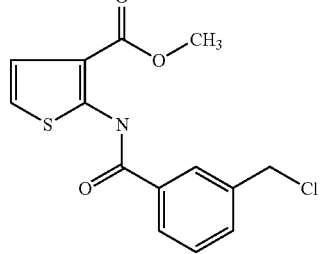 | 223.471 |
| 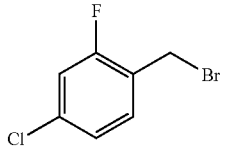 | 276.549 |
| 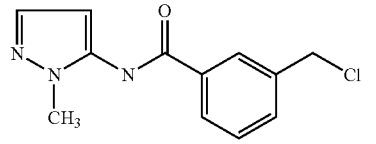 | 168.047 |
| 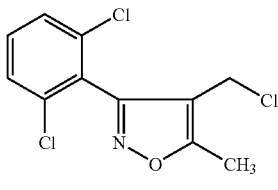 | 162.566 |
| 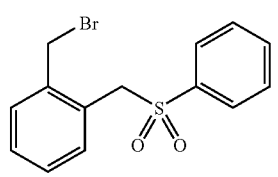 | 224.646 |
| 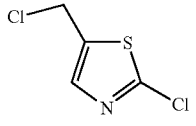 | 186.637 |
| 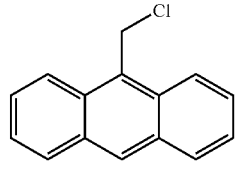 | |
-continued
| Alkylating reagent | MW |
|---|---|
| 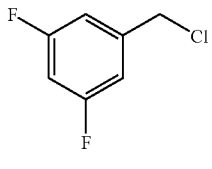 | |
| 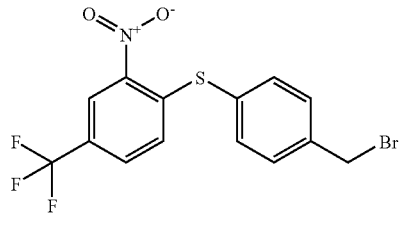 | |
| 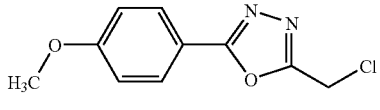 | |
| 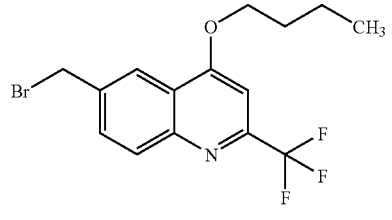 | |
| 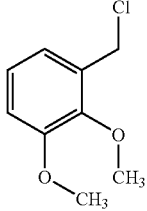 | |
| 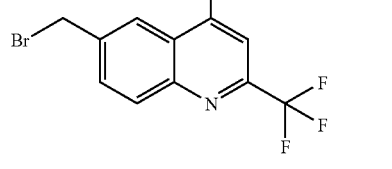 | |
| 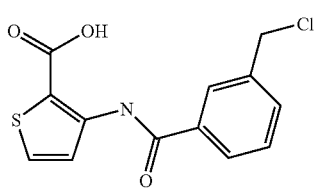 | 154.639 |

| Alkylating reagent | MW |
|---|---|
| (3-benzyloxybenzyl bromide) | 277.16 |
| (2-phenoxybenzyl bromide) | 263.133 |
| (3,5-dimethoxybenzyl bromide) | 231.088 |
| (5-(2-thienyl)-3-(chloromethyl)-1,2,4-oxadiazole) | 200.648 |
| (4-(chloromethyl)-2-(2-thienyl)thiazole) | 215.727 |
| (3-fluoro-4-chloro-2-(trifluoromethyl)benzyl bromide) | 291.469 |
| (4-chloro-2-(trifluoromethyl)benzyl bromide) | 273.478 |
| (1-(chloromethyl)naphthalene) | |

| Alkylating reagent | MW |
|---|---|
| (2-chloro-4-fluorobenzyl chloride) | |
| (2,6-dichloro-styryl-4-bromomethylbenzene) | |
| (6-methyl-2-(3-(chloromethyl)phenyl)-4H-benzo[d][1,3]oxazin-4-one) | |
| (7-chloro-2-(3-(chloromethyl)phenyl)-4H-benzo[d][1,3]oxazin-4-one) | |
| (2-(2-(chloromethyl)phenyl)-7-chloro-4H-benzo[d][1,3]oxazin-4-one) | |
| (6,7-dichloro-8-(chloromethyl)-4H-benzo[d][1,3]dioxine) | |
| (N-(5-methylisoxazol-3-yl)-4-(chloromethyl)benzamide) | |
| (2-fluoro-3-chloro-6-methylbenzyl bromide) | 237.498 |

-continued

| Alkylating reagent | MW |
|---|---|
| 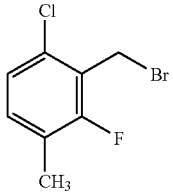 | 237.498 |
| 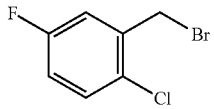 | 223.471 |
| 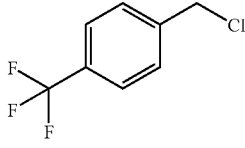 | |
| 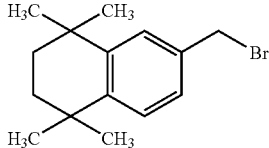 | |

Scheme B shows a synthetic route to additional imidazopyrimidines.

Scheme B:

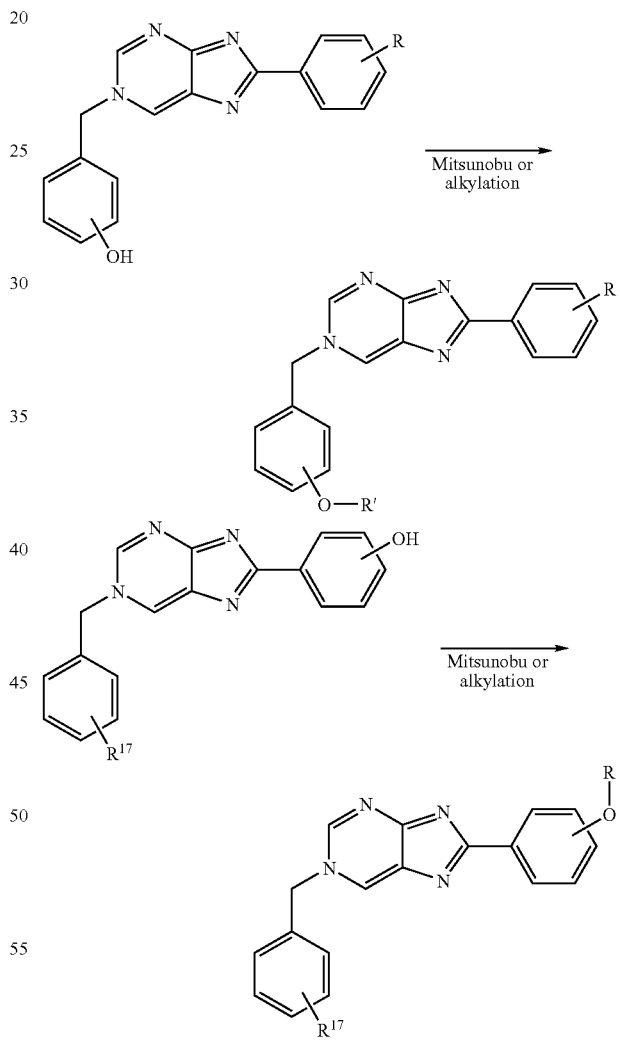

-continued

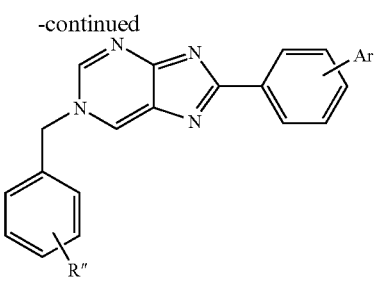

Scheme C shows a synthetic route to the compounds of this invention. R, R', and R" can be any alkyl, benzylic or heterobenzylic groups.

Scheme C:

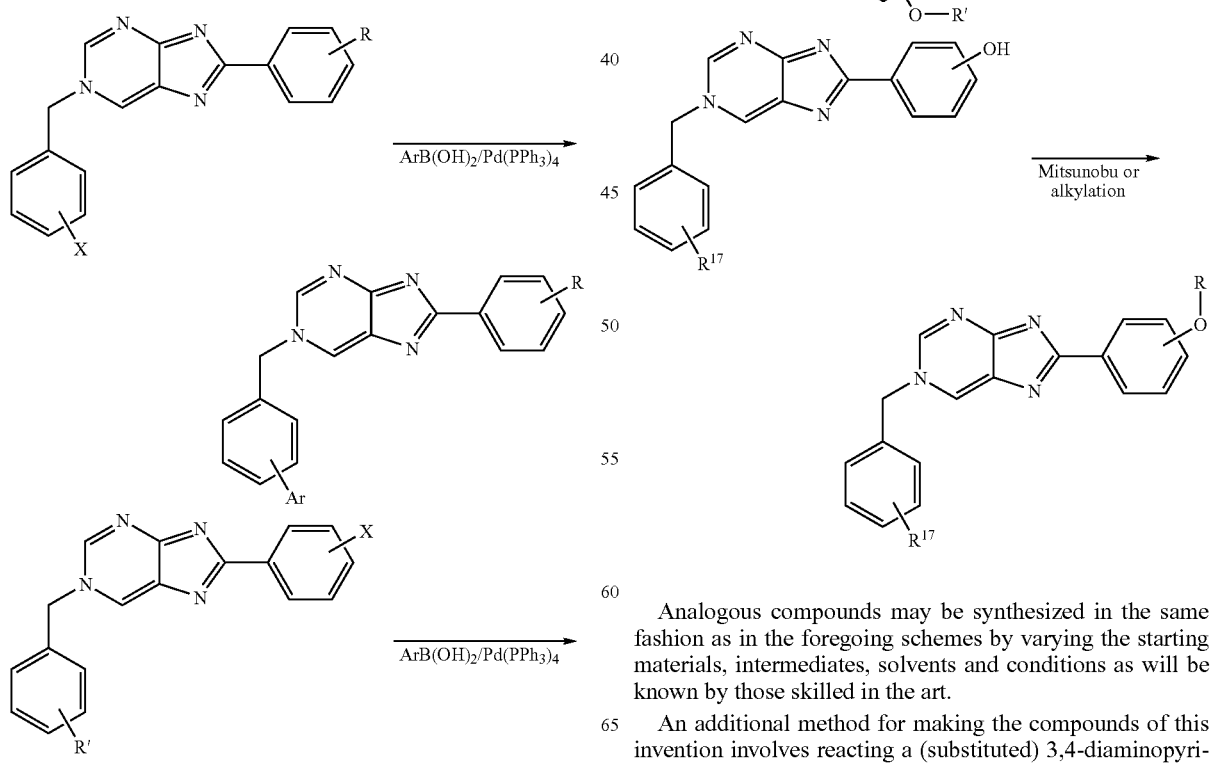

Analogous compounds may be synthesized in the same fashion as in the foregoing schemes by varying the starting materials, intermediates, solvents and conditions as will be known by those skilled in the art.

An additional method for making the compounds of this invention involves reacting a (substituted) 3,4-diaminopyrimidine (A) with B (Y—$R^1$) to give imidazo[4,5-d]pyrimidines (C); introducing further substituents (R², R⁴ and/or R⁵≠H) either a) by cylization of an appropriately substituted 3,4-diaminopyrimidine (A) or b)) by introduction of the substituent(s) onto the imidazo[4,5-d]pyrimidine (C); reacting the imidazo[4,5-c]pyrimidine (C) with an alkylating agent (D) (R³—X—R⁶) in an appropriate solvent under addition of a base at ambient temperature; and optionally, in the case of hydroxy, mercapto or amino substituents in position 4 or 6 of the imidazopyrimidine (Z=O, S or NR); introducing a further substituent (R²⁵ or R²⁶) at position 1 or 3 of the imidazo[4,5-d]pyrimidine.

Compounds of the invention also are conveniently prepared by a two step process. First, a (substituted) 3,4-diaminopyrimidine (A) is reacted with B to give imidazo[4,5-d] pyrimidines C (Scheme 1). If Y is COOH, then the cyclization is carried out under acidic catalysis (preferably in polyphosphoric acid at a temperature between 90 and 200° C.); other methods include reaction in 4N hydrochloric acid at reflux temperature or neat at a temperature between 90 and 180° C. (for aliphatic carboxylic acids). In the case of acid-sensitive groups like alkoxy or thiophene, the reaction can be carried out in phosphorus oxychloride at a temperature between 70 and 120° C. Alternatively, reaction with aldehydes (Y=CHO) or their bisulfite adducts under oxidative conditions (nitrobenzene, DDQ, copper(II)acetate, O₂ sulfur etc.) gives imidazo[4,5-d]pyrimidines C. Other methods are the reaction of (substituted) 3,4-diaminopyrimidines (A) with orthoesters (Y=C(OR)₃), anhydrides (Y=OCOOR) or acid halogenides (Y=COX), etc.

Further methods for the preparation of the compounds of the invention are set forth in Schemes 1-5 below.

Scheme 1:

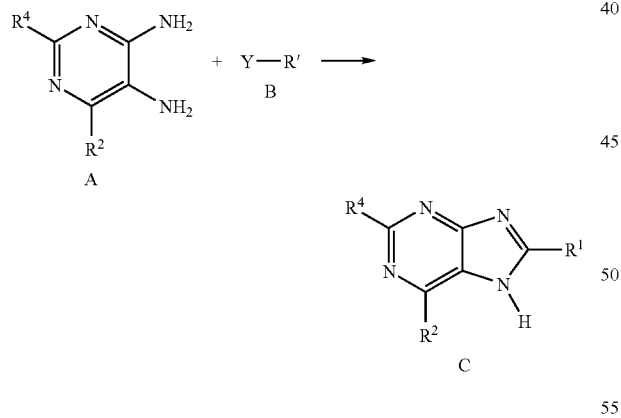

The imidazo[4,5-d]pyrimidines C are present in four tautomeric forms (1H, 3H, 4H, 6H).

Substituents, for example R² and R⁴, are introduced by two ways: i) by cylization of an appropiately substituted 3,4-diaminopyrimidine or ii) by introduction of the substituent(s) onto the imidazo[4,5-d]pyrimidine. Nitroamino pyrimidines are commercially available. Reduction of the nitro group with iron in a mixture of concentrated hydrochloric acid and ethanol gives the desired substituted 3,4-diaminopyrimidine starting materials.

Scheme 2:

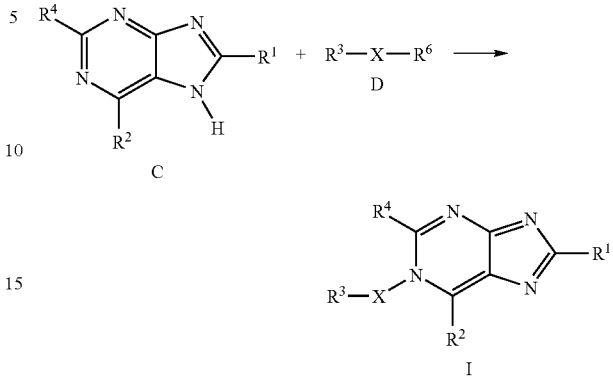

This reaction gives mixtures of four alkylation products. For example, reaction of imidazo[4,5-d]pyrimidine C(R¹=2, 6-difluorophenyl, R²=R⁴=H) with 2,6-difluorobenzyl bromide would be expected to give the following mixture.

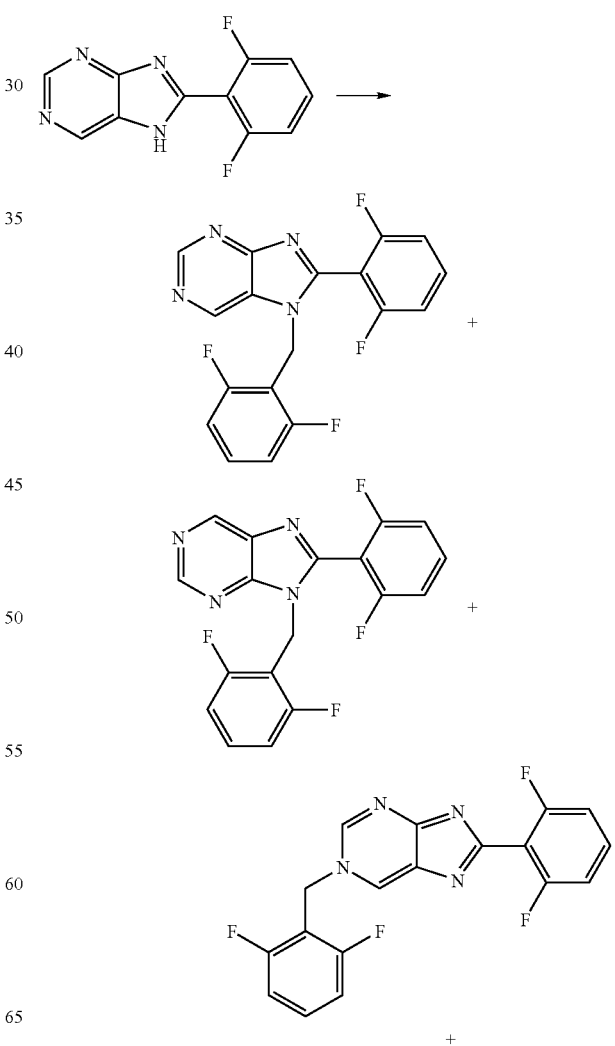

-continued

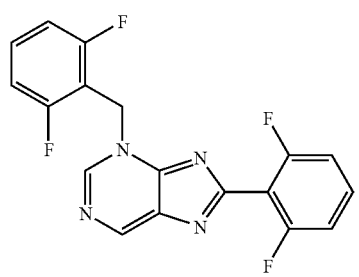

This mixture can be separated by column chromatography (silica gel, eluent: mixture of dichloromethane and methanol). The structures of the isolated components can then be assigned by NMR spectroscopy by single crystal x-ray analysis.

Alternatively, the crude reaction mixture can be recrystallized from an appropiate solvent (mixture), e.g. from a mixture of diisopropyl ether and ethyl acetate, to give the pure alkylated products.

E
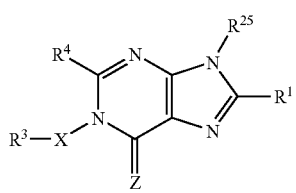

F
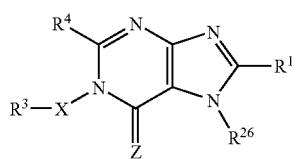

G
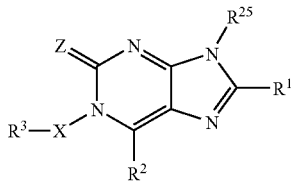

H
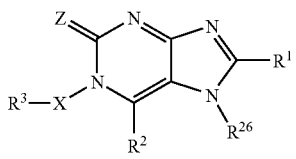

Compounds of general structure E, F, G and H can be prepared by alkylation (for example with (cyclo)alkylbromide or (cyclo)alkyliodide etc.) of the corresponding compounds where Z=O, Z=S or Z=NR or their isomers. The resulting mixtures can be separated by column chromatography. The required starting materials are, for example, prepared from the corresponding chloro-analogues by nucleophilic substitution, or by ether cleavage of the corresponding alkoxy analogues.

Scheme 3
Isoxazole Telescoping Scheme

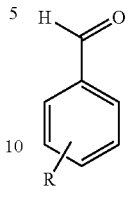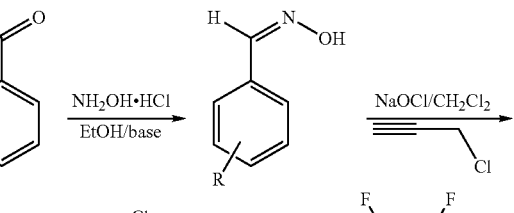

R = R$^{19}$; further embodiments comprise replacing phe-R with other R$^{17}$.

Scheme 4
Preparation of Pyridazine Phenyl Alkoxy Array

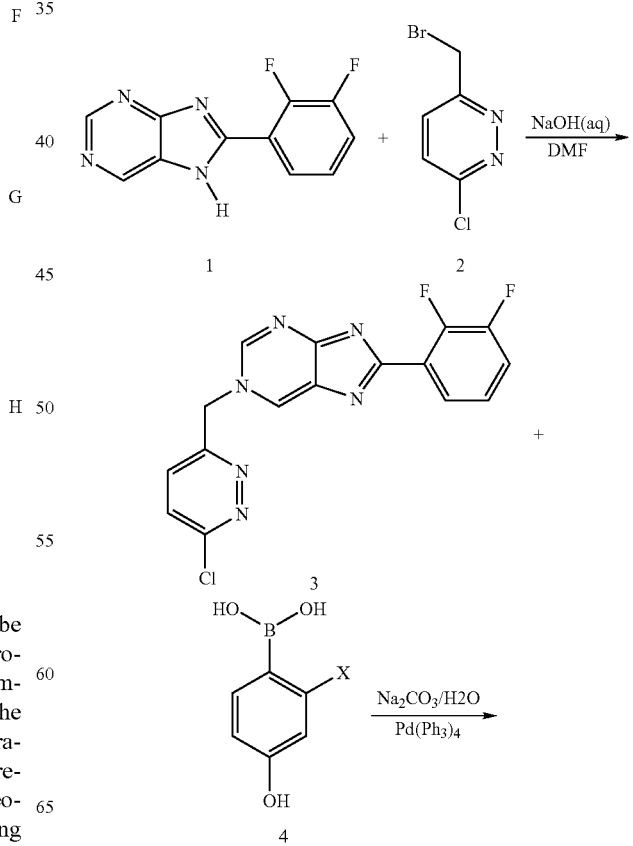

-continued

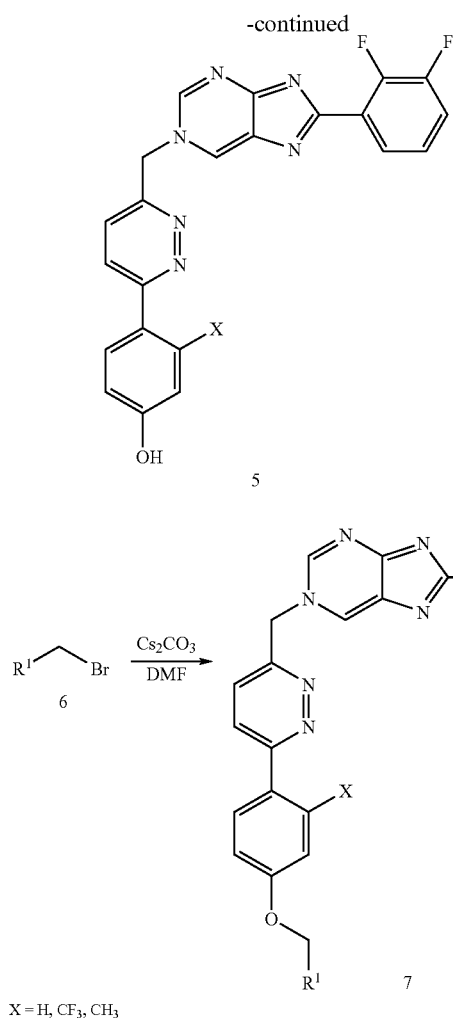

X = H, CF₃, CH₃

Further embodiments: Replace 2 with other bromides consistent with R³, replace 4 with other R¹⁷ precursors.

Scheme 5 shows further examples for the synthesis of compounds with a substituted (het)aryl of the imidazo[4,5-d]pyrimidine ring system.

Scheme 5:

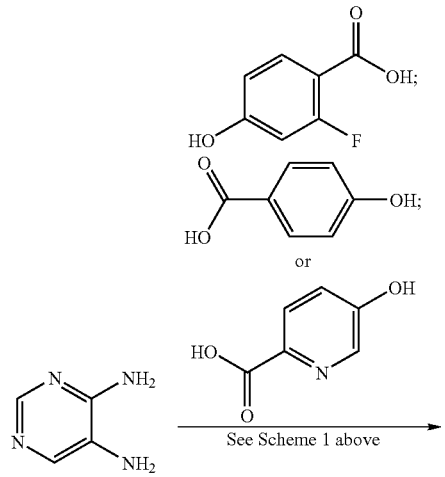

-continued

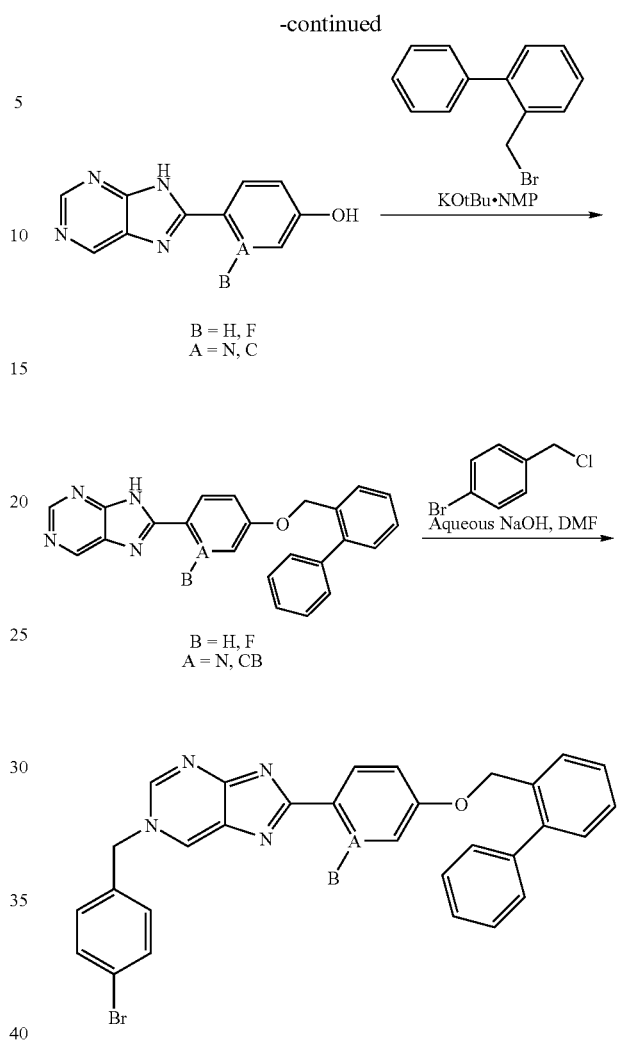

Analogous compounds are synthesized in the same fashion as in the foregoing schemes and the following examples by varying the starting materials, intermediates, solvents and conditions as will be known by those skilled in the art.

Example 1

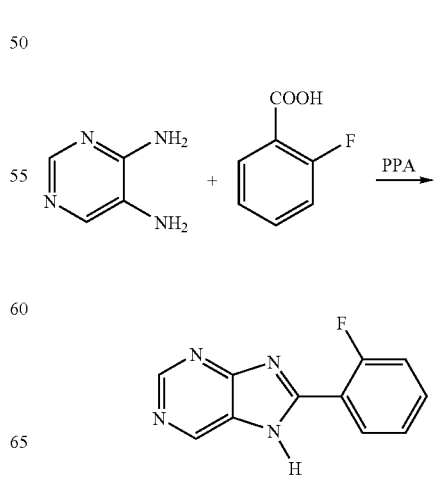

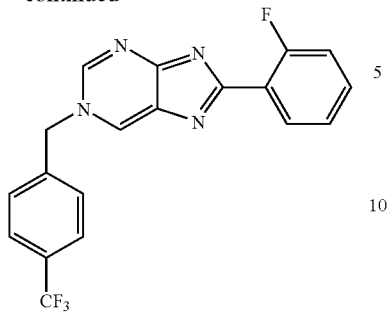

A 8-(2-Fluorophenyl)-purine

A mixture of 4,5-diaminopyrimidine (0.500 g), 2-fluorobenzoic acid (0.700 g) and polyphosphoric acid (25 mL) was heated at 180° C. for 3 hours. Then the reaction mixture was cooled and poured into water (500 mL). The solution was adjusted to pH=8-9 by addition of solid NaOH and the resulting precipitate was collected by filtration, washed with water and dried to give 8-(2-fluorophenyl)-purine (off-white powder, 88.5%).

$^1$H NMR (200 MHz, DMSO-$d_6$) δ 13.79 (br s, 1H, NH), 9.14 (s, 1H, purine-H), 8.95 (s, 1H, purine-H), 8.23 (m, 1H, phenyl-H), 7.73-7.41 (m, 3H, phenyl-H).

B 8-(2-Fluorophenyl)-1-[(4-trifluoromethyl)phenylmethyl]-1H-purine 8-(2-Fluorophenyl)-purine (430 mg) was dissolved in dry DMF (4 mL), aqueous 30% NaOH solution (400 mg) was added and the resulting mixture was stirred for 30 minutes. Then, 4-(trifluoromethyl)benzyl chloride (469 mg) was added and the resulting mixture was stirred for 1 day at ambient temperature. Water (200 mL) was and the resulting solution was extracted with ethyl acetate (3×70 mL). The combined ethyl acetate phases were dried (Na$_2$SO$_4$) and evaporated. The residue was recrystallized from a mixture of diisopropyl ether (10 mL) and ethyl acetate (30 mL) to give 8-(2-fluorophenyl)-1-[(4-trifluoromethyl)phenylmethyl]-1H-purine (GPJN-179) as an off-white powder (yield: 18.9%, m.p.: 251-256° C.).

$^1$H NMR (200 MHz, DMSO-$d_6$) δ 9.25 (d, 1H, purine-H, J=2.0 Hz), 9.14 (d, 1H, purine-H, J=2.0 Hz), 8.33 (m, 1H, phenyl-H), 7.83-7.65 (AA'BB', 4H, benzyl-H), 7.53 (m, 1H, phenyl-H); 7.38-7.27 (m, 2H, phenyl-H), 5.78 (s, 2H, CH$_2$).

Example 2

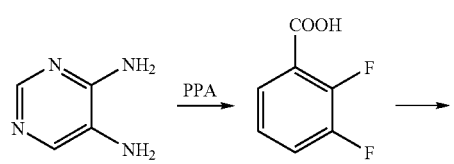

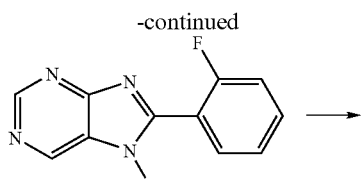

A 8-(2,3-Difluorophenyl)-purine

Synthesized as described above for 8-(2-fluorophenyl)-purine, except that 2,3-difluorobenzoic acid was used instead of 2-fluorobenzoic acid (white powder, yield: 45.7%)

$^1$H NMR (200 MHz, DMSO-$d_6$) δ 13.70 (br s, 1H, NH), 9.18 (s, 1H, purine-H), 8.97 (s, 1H, purine-H), 8.04-7.96 (m, 1H, phenyl-H), 7.78-7.64 (m, 1H, phenyl-H), 7.52-7.40 (m, 1H, phenyl-H).

B 8-(2,3-Difluorophenyl)-1-[(4-trifluoromethyl)phenylmethyl]-1H-purine

Synthesized as described above for Example 1, except that 8-(2,3-difluorophenyl)-purine was used instead of 8-(2-fluorophenyl)-purine (white powder, yield: 9.4%, m.p.: 267-271° C.).

$^1$H NMR (200 MHz, DMSO-$d_6$) δ 9.33 (d, 1H, purine-H, J=2.0 Hz), 9.17 (d, 1H, purine-H, J=2.0 Hz), 8.14 (m, 1H, phenyl-H), 7.82-7.67 (AA'BB',4H, benzyl-H), 7.62-7.49 (m, 1H, phenyl-H), 7.40-7.28 (m, 1H, phenyl-H), 5.79 (s, 2H, CH$_2$).

Example 3

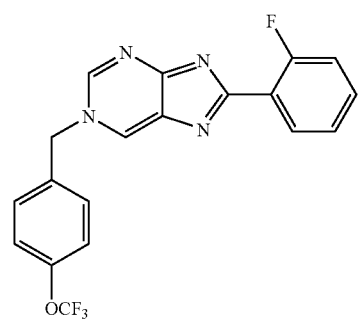

Synthesized as described above for Example 1, except that 4-(trifluoromethoxy)benzyl bromide was used instead of 4-(trifluoromethyl)benzyl chloride (white powder, yield: 11.2%, m.p.: 224-228° C.).

$^1$H NMR (200 MHz, DMSO-d$_6$) δ 9.24 (d, 1H, purine-H, J=2.0 Hz), 9.13 (d, 1H, purine-H, J=2.0 Hz), 8.31 (m, 1H, phenyl-H), 7.66-7.26 (m, 6H, 4 benzyl-H, 2 phenyl-H), 5.69 (s, 2H, CH$_2$).

Example 4

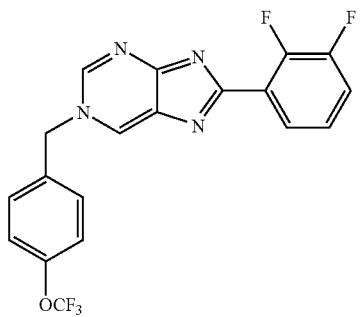

Synthesized as described above for Example 2, except that 4-(trifluoromethoxy)benzyl bromide was used instead of 4-(trifluoromethyl)benzyl chloride (gray powder, yield: 21.5%, m.p.: 254-258° C.).

$^1$H NMR (200 MHz, DMSO-d$_6$) δ 9.34 (d, 1H, purine-H, J=2.0 Hz), 9.19 (d, 1H, purine-H, J=2.0 Hz), 8.14 (m, 1H, phenyl-H), 7.68-7.41 (AA'BB', 4H, benzyl-H), 7.59-7.29 (m, 2H, phenyl-H), 5.72 (s, 2H, CH$_2$).

Example 5

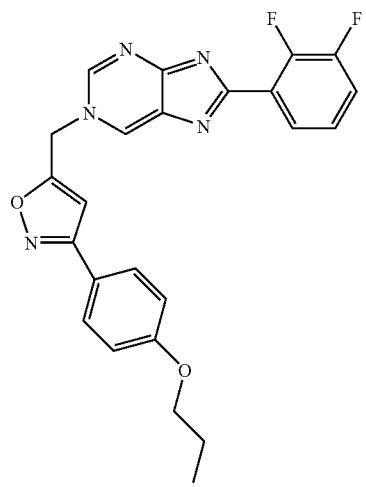

Synthesized as described above for Example 2, except that 5-chloromethyl-3-(4-propoxyphenyl)-isoxazole was used instead of 4-(trifluoromethyl)benzyl chloride. Purified by column chromatography (silica gel, eluent: dichloromethane:methanol=20:1), followed by recrystallization (diisopropyl ether/ethyl acetate). Colourless crystals, yield: 7.4%, m.p.: 228-231° C.).

$^1$H NMR (200 MHz, DMSO-d$_6$) δ 9.34 (d, 1H, purine-H, J=2.0 Hz), 9.15 (d, 1H, purine-H, J=2.0 Hz), 8.17 (m, 1H, phenyl-H), 7.88-7.08 (AA'BB', 4H, benzyl-H), 7.63-7.48 (m, 1H, phenyl-H), 7.41-7.30 (m, 1H, phenyl-H), 7.01 (s, 1H, isoxazole-H), 5.98 (s, 2H, CH$_2$), 3.98 (t, 2H, OCH$_2$, J=6.6 Hz), 1.73 (hex, 2H, CH$_2$, J=6.6 Hz), 0.97 (t, 3H, CH$_3$, J=6.6 Hz).

Example 6

Preparation of 1-((3-(4-chlorophenyl)isoxazol-5-yl)methyl)-8-(2,3-difluorophenyl)-1H-purine

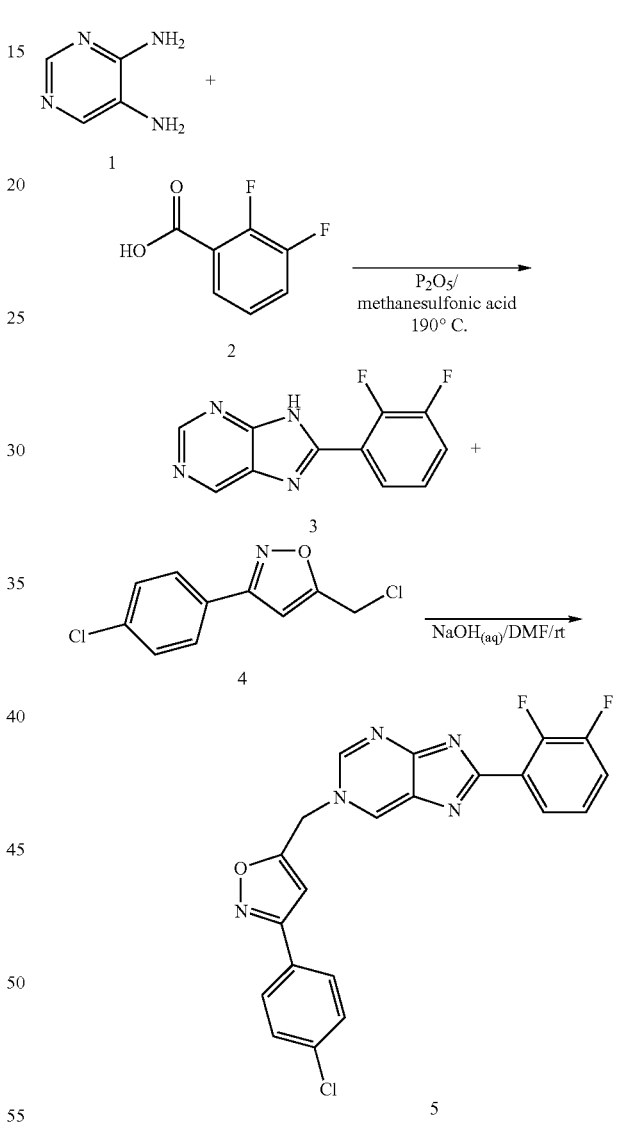

4,5-Diaminopyrimidine (1) (4.5 g, 0.04 moles) and 2,3-difluorobenzoic acid (2) (6.95 g, 0.044 moles) were suspended in 100 mL of Eaton's Acid. The reaction mixture was heated in an oil bath at 190° C. for 2 hours and then poured into 800 mL ice/water. Solid sodium hydroxide was added (59 g, 1.5 moles) to adjust to pH 5, which resulted in the product precipitating from solution. The product was filtered and washed twice with deionized water and air dried. The crude product was recrystallized from water/ethanol resulting in 8 g of pure product (3) (M+1=233).

Purine (3) (500 mg, 2.15 mmoles) was dissolved in 10 mL of anhydrous DMF and 1.1 mL of sodium hydroxide solution (10% w/v) was added. 5-(Chloromethyl)-3-(4-chlorophenyl) isoxazole (4) (587 mg, 2.6 mmoles) was added to the above reaction mixture and the solution was stirred at room temperature overnight. The crude product was triturated from water followed by recrystallization from hot ethyl acetate. The precipitate was filtered to yield 30 mg of the gold colored solid 1-((3-(4-chlorophenyl)isoxazol-5-yl)methyl)-8-(2,3-difluorophenyl)-1H-purine 5) in high purity as determined by analytical LC/MS (M+1=429) and $^1$H NMR (400 MHz, DMSO-$d_6$) δ 5.99 (s, 2H), 7.17 (s, 1H), 7.34 (m, 1H), 7.55 (s, 1H), 7.56 (d, 2H), 7.87 (d, 2H), 8.14 (m, 1H), 9.14 (s, 1H), 9.32 (s, 1H).

Example 7

Determination of Antiviral (EC50) and Cytostatic Activity (CC50)

Cells and Viruses

Madin-Darbey Bovine Kidney (MDBK) cells were maintained in Dulbecco's modified Eagle medium (DMEM) supplemented with BVDV-free 5% fetal calf serum (DMEME-FCS) at 37° C. in a humidified, 5% $CO_2$ atmosphere.

Determination of Cytostatic Effect on MDBK Cells

The effect of the drugs on exponentially growing MDBK cells was assessed as follows. Cells were seeded at a density of 5000 cell/well in 96 well plates in MEM medium (Gibco) supplemented with 10% fetal calf serum, 2 mM L-glutamine (Life Technologies) and bicarbonate (Life Technologies). Cells were cultured for 24 hr after which serial dilutions of the test compounds were added. Cultures were then again further incubated for 3 days after which the effect on cell growth was quantified by means of the MTS method (Promega). The concentration that results in 50% inhibition of cell growth is defined as the 50% cytostatic concentration ($CC_{50}$).

Anti-HCV Assay/Replicon Assay

Huh-5-2 cells [a cell line with a persistent HCV replicon I389luc-ubi-neo/NS3-3'/5.1; replicon with firefly luciferase-ubiquitin-neomycin phosphotransferase fusion protein and EMCV-IRES driven NS3-5B HCV polyprotein] was cultured in RPMI medium (Gibco) supplemented with 10% fetal calf serum, 2 mM L-glutamine (Life Technologies), 1× non-essential amino acids (Life Technologies); 100 IU/ml penicillin and 100 ug/ml streptomycin and 250 ug/ml G418 (Geneticin, Life Technologies). Cells were seeded at a densitiy of 7000 cells per well in 96 well View Plate™ (Packard) in medium containing the same components as described above, except for G418. Cells were allowed to adhere and proliferate for 24 hr. At that time, culture medium was removed and serial dilutions of the test compounds were added in culture medium lacking G418. Interferon alfa 2a (500 IU) was included as a positive control. Plates were further incubated at 37° C. and 5% $CO_2$ for 72 hours. Replication of the HCV replicon in Huh-5 cells results in luciferase activity in the cells. Luciferase activity is measured by adding 50 µl of 1×Glo-lysis buffer (Promega) for 15 minutes followed by 50 ul of the Steady-Glo Luciferase assay reagent (Promega). Luciferase activity is measured with a luminometer and the signal in each individual well is expressed as a percentage of the untreated cultures. Parallel cultures of Huh-5-2 cells, seeded at a density of 7000 cells/well of classical 96-well cel culture plates (Becton-Dickinson) are treated in a similar fashion except that no Glo-lysis buffer or Steady-Glo Luciferase reagent is added. Instead the density of the culture is measured by means of the MTS method (Promega).

Quantitative Analysis of HCV RNA by Taqman Real-Time RT-PCR

Replicon cells were plated at $7.5\times10^3$ cells per well in a 96-well plate plates at 37° C. and 5% $CO_2$ in Dulbecco's modified essential medium containing 10% fetal calf serum, 1% nonessential amino acids and 1 mg/ml Geneticin. After allowing 24 h for cell attachment, different dilutions of compound were added to the cultures. Plates were incubated for 5 days, at which time RNA was extracted using the Qiamp Rneazyi Kit (Qiagen, Hilden, Germany). A 50 µL PCR reaction contained TaqMan EZ buffer (50 mmol/L Bicine, 115 mmol/L potassium acetate, 0.01 mmol/L EDTA, 60 nmol/L 6-carboxy-X-rhodamine, and 8% glycerol, pH 8.2; Perkin Elmer Corp./Applied Biosystems), 300 µmol/L deoxyadenosine triphosphate, 300 µmol/L deoxyguanosine triphosphate, 300 µmol/L deoxycytidine triphosphate, 600 mmol/L deoxyuridine triphosphate, 200 µmol/L forward primer [5'-ccg gcT Acc Tgc ccA TTc], 200 mmol/L reverse primer [ccA GaT cAT ccT gAT cgA cAA G], 100 µmol/L TaqMan probe [6-FAM-AcA Tcg cAT cgA gcg Agc Acg TAc-TAMRA], 3 mmol/L manganese acetate, 0.5 U AmpErase uracil-N-glycosylase, 7.5 U rTth DNA polymerase, and 10 µl of RNA elution. After initial activation of uracil-N-glycosylase at 50° C. for 2 minutes, RT was performed at 60° C. for 30 minutes, followed by inactivation of uracil-N-glycosylase at 95° C. for 5 minutes. Subsequent PCR amplification consisted of 40 cycles of denaturation at 94° C. for 20 seconds and annealing and extension at 62° C. for 1 minute in an ABI 7700 sequence detector. For each PCR run, negative template and positive template samples were used. The cycle threshold value (Ct-value) is defined as the number of PCR cycles for which the signal exceeds the baseline, which defines a positive value. The sample was considered to be positive if the Ct-value was <50. Results are expressed as genomic equivalents (GE).

Example 8

Assay Results

All of the compounds of examples 1-6 exhibited excellent anti-HCV antiviral activity and low toxicity.

We claim:
1. A compound of formula (A)

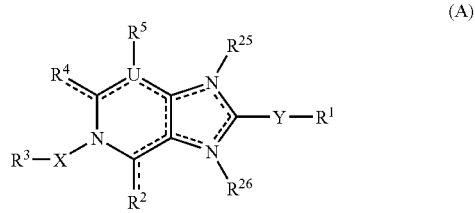

wherein:
the dotted lines represent optional double bonds, provided that no two double bonds are adjacent to one another, and that the dotted lines represent at least 3, optionally 4 double bonds;
U is N;
$R^1$ is selected from hydrogen, aryl, heterocycle, $C_1$-$C_{10}$ alkoxy, $C_1$-$C_{10}$ alkyl-amino, $C_1$-$C_{10}$ dialkyl-amino, $C_{3-10}$ cycloalkyl, $C_{4-10}$ cycloalkenyl, and $C_{4-10}$ cycloalkynyl, wherein each are optionally substituted with 1 or more $R^6$;

Y is selected from a single bond, O, S(O)m (where m is an integer from 0 to 2), $NR^{11}$, $C_{1-10}$ alkylene, $C_{2-10}$ alkenylene, and $C_{2-10}$ alkynylene, or $C_{1-10}$ alkylene, $C_{2-20}$ alkenylene or $C_{2-10}$ alkynylene, wherein 1 to 3 methylene groups optionally are independently replaced by 1 to 3 heteroatoms selected from O, S or $NR^{11}$, provided that when Y is a single bond, $R^1$ is not hydrogen;

$R^2$ and $R^4$ are independently selected from hydrogen, $C_{1-18}$ alkyl, $C_{2-18}$ alkenyl, $C_{2-18}$ alkynyl, $C_{1-18}$ alkoxy, $C_{1-18}$ alkylthio, halogen, —OH, —CN, —$NO_2$, —$NR^7R^8$, haloalkyloxy, haloalkyl, —C(=O)$R^9$, —C(=S)$R^9$, SH, aryl, aryloxy, arylthio, arylalkyl, $C_{1-18}$ hydroxyalkyl, $C_{3-10}$ cycloalkyl, $C_{3-10}$ cycloalkyloxy, $C_{3-10}$ cycloalkylthio, $C_{3-10}$ cycloalkenyl, $C_{7-10}$ cycloalkynyl, and heterocycle, provided that when one of $R^{25}$ or $R^{26}$ is present, then either $R^4$ is selected from =O, =S, or =$NR^{27}$ or $R^2$ is selected from =S or =$NR^{27}$;

X is selected from $C_1$-$C_{10}$ alkylene, $C_{2-10}$ alkenylene or $C_{2-10}$ alkynylene;

$R^3$ is selected from aryl, aryloxy, arylthio, cycloalkyl, cycloalkenyl, cycloalkynyl, aryl-N($R^{10}$)—, or heterocycle, where each said substituent is optionally substituted with at least one $R^{17}$, provided that for cycloalkenyl the double bond is not adjacent to a nitrogen;

$R^5$ independently is absent or is selected from hydrogen, $C_{1-18}$ alkyl, $C_{2-18}$ alkenyl, $C_{2-18}$ alkynyl, $C_{1-18}$ alkoxy, $C_{1-18}$ alkylthio, halogen, —OH, —CN, —$NO_2$, —$NR^7R^8$, haloalkyloxy, haloalkyl, —C(=O)$R^9$, —C(=O)O$R^9$, —C(=S)$R^9$, SH, aryl, aryloxy, arylthio, arylalkyl, $C_{1-18}$ hydroxyalkyl, $C_{3-10}$ cycloalkyl, $C_{3-10}$ cycloalkyloxy, $C_{3-10}$ cycloalkylthio, $C_{3-10}$ cycloalkenyl, $C_{7-10}$ cycloalkynyl, and heterocycle;

$R^6$ is selected from hydrogen, $C_{1-18}$ alkyl, $C_{2-18}$ alkenyl, $C_{2-18}$ alkynyl, $C_{1-18}$ alkoxy, $C_{1-18}$ alkylthio, $C_{1-18}$ alkylsulfoxide, $C_{1-18}$ alkylsulfone, $C_{1-18}$ halo-alkyl, $C_{2-18}$ halo-alkenyl, $C_{2-18}$ halo-alkynyl, $C_{1-18}$ halo-alkoxy, $C_{1-18}$ halo-alkylthio, $C_{3-10}$ cycloalkyl, $C_{3-10}$ cycloalkenyl, $C_{7-10}$ cycloalkynyl, halogen, OH, CN, cyanoalkyl, —$CO_2R^{18}$, $NO_2$, —$NR^7R^8$, $C_{1-18}$ haloalkyl, C(=O)$R^{18}$, C(=S)$R^{18}$, SH, aryl, aryloxy, arylthio, arylsulfoxide, arylsulfone, arylsulfonamide, aryl($C_{1-18}$)alkyl, aryl($C_{1-18}$)alkyloxy, aryl($C_{1-18}$)alkylthio, heterocycle, and $C_{1-18}$ hydroxyalkyl, where each may be optionally substituted with at least 1 $R^{19}$;

$R^7$ and $R^8$ are independently selected from hydrogen, $C_{1-18}$ alkyl, $C_{1-18}$ alkenyl, aryl, $C_{3-10}$ cycloalkyl, $C_{4-10}$ cycloalkenyl, heterocycle, —C(=O)$R^{12}$; —C(=S)$R^{12}$, an amino acid residue linked through a carboxyl group thereof, and the group formed when $R^7$ and $R^8$ are taken together with the nitrogen to form a heterocycle;

$R^9$ and $R^{18}$ are independently selected from hydrogen, OH, $C_{1-18}$ alkyl, $C_{2-18}$ alkenyl, $C_{3-10}$ cycloalkyl, $C_{4-10}$ cycloalkenyl, $C_{1-18}$ alkoxy, —$NR^{15}R^{16}$, aryl, an amino acid residue linked through an amino group of the amino acid, $CH_2OCH(=O)R^{9a}$, and $CH_2OC(=O)OR^{9a}$ where $R^{9a}$ is $C_1$-$C_{12}$ alkyl, $C_6$-$C_{20}$ aryl, $C_6C_7$-$C_{20}$ alkylaryl or $C_7$-$C_{20}$ aralkyl;

$R^{10}$ and $R^{11}$ are independently selected from the group consisting of hydrogen, $C_{1-18}$ alkyl, $C_{2-18}$ alkenyl, $C_{3-10}$ cycloalkyl, $C_{4-10}$ cycloalkenyl, aryl, —C(=O)$R^{12}$, heterocycle, and an amino acid residue linked through an amino group or carboxyl group of the amino acid;

$R^{12}$ is selected from the group consisting of hydrogen, $C_{1-18}$ alkyl, $C_{2-18}$ alkenyl, aryl, $C_{3-10}$ cycloalkyl, $C_{4-10}$ cycloalkenyl, and an amino acid residue linked through an amino group or carboxyl group of the amino acid;

$R^{15}$ and $R^{16}$ are independently selected from hydrogen, $C_{1-48}$ alkyl, $C_{2-18}$ alkenyl, $C_{2-18}$ alkynyl, aryl, arylalkyl (unsubstituted, or substituted with C(O)O$R^{18}$), $C_{3-10}$ cycloalkyl, $C_{4-10}$ cycloalkenyl, and an amino acid residue linked through an amino group or carboxyl group of the amino acid;

$R^{17}$ is independently selected from the group consisting of
(a) hydrogen, $C_{1-18}$ alkyl, $C_{2-18}$ alkenyl, $C_{2-18}$ alkynyl, $C_{1-18}$ alkoxy, $C_{1-48}$ alkylthio, $C_{1-18}$ alkylsulfoxide, $C_{1-18}$ alkylsulfone, $C_{1-18}$ halogenated alkyl, $C_{2-18}$ halogenated alkenyl, $C_{2-48}$ halogenated alkynyl, $C_{1-48}$ halogenated alkoxy, $C_{1-18}$ halogenated alkylthio, $C_{3-10}$ cycloalkyl, $C_{3-10}$ cycloalkenyl, $C_{7-10}$ cycloalkynyl, halogen, OH, CN, $CO_2H$, $CO_2R^{18}$, $NO_2$, $NR^7R^8$, haloalkyl, C(=O)$R^{18}$, C(=S)$R^{18}$, SH, aryl, heterocycle, aryloxy, arylthio, arylsulfoxide, arylsulfone, arylsulfonamide, arylalkyl, arylalkyloxy, arylalkylthio, heterocycle and $C_{1-18}$ hydroxyalkyl, where each of said aryl, aryloxy, arylthio, arylsulfoxide, arylsulfone, arylsulfonamide, arylalkyl, arylalkyloxy, arylalkylthio, heterocycle, or $C_{1-18}$ hydroxyalkyl is optionally substituted with 1 or more $R^{19}$, and (b) M-Q- wherein M is a ring optionally substituted with 1 or more $R^{19}$, and Q is a bond or a linking group connecting M to $R^3$ having 1 to 10 atoms selected from C and optionally 1 or more O, N or S atoms and optionally substituted with 1 or more $R^{19}$;

$R^{19}$ is selected from
(a) H;
(b) $NO_2$, SH, $NR^{20}R^{21}$, OH, halogen and CN;
(c) $C_{1-18}$ alkyl, $C_{2-18}$ alkenyl and $C_{2-18}$ alkynyl;
(d) $C_{1-18}$ alkyl, $C_{2-18}$ alkenyl and $C_{2-18}$ alkynyl wherein 1 or more methylene are replaced by 1 or more O, S, $NR^{20}$, or $N(R^{20})C(O)$;
(e) Substituents c), or d) substituted further by $C_{3-10}$ cycloalkyl, $C_{4-10}$ cycloalkenyl, $C_{4-10}$ cycloalkynyl, aryl or heterocycle;
(f) $C_{3-10}$ cycloalkyl, $C_{4-10}$ cycloalkenyl, $C_{4-10}$ cycloalkynyl, aryl and heterocycle, or said groups substituted with $C_{1-6}$ alkyl, C(O)O$R^{12}$=O, halogen, CN, C(O)$NR^{20}R^{21}$, C(O)$R^{18}$ or OC(O)$R^{18}$;
(g) C(O)$R^{18}$, C(O)O$R^{18}$, OC(O)$R^{18}$, C(S)$R^{18}$ and C(O)N($R^{12}$)$_2$;
(h) Substituents c) or d) substituted with =O, CN, halogen, C(O)$R^{18}$, C(O)$NR^{20}R^{21}$, OC(O)$R^{18}$, heterocycle, and heterocycle substituted with $C_1$-$C_6$ alkyl, C(O)O$R^{12}$, =O, CN, halogen, OC(O)$R^{18}$ or C(O)$NR^{20}R^{21}$; and
(i) Substituents e) or f) substituted further with $C_{1-18}$ alkyl, =O, $NR^{20}R^{21}$, CN, $C_{1-18}$ alkoxy, heterocycle, $C_{1-18}$ haloalkyl, heterocyclealkyl or halogen;

$R^{20}$ and $R^{21}$ are independently selected from hydrogen, $C_{1-18}$ alkyl, $C_{2-18}$ alkenyl, $C_{2-18}$ alkynyl, aryl, heterocycle, $C_{3-10}$ cycloalkyl, $C_{4-10}$ cycloalkenyl, —C(=O)$R^{12}$, and —C(=S)$R^{12}$;

$R^{25}$ is not present or is selected from hydrogen, $C_{3-10}$ cycloalkyl, aryl and heterocycle, where each is optionally independently substituted with 1 to 4 of $C_{1-6}$ alkyl, $C_{1-8}$ alkoxy, halo, $CH_2OH$, and benzyloxy;

$R^{26}$ is not present or is selected from hydrogen, $C_{1-18}$ alkyl, $C_{3-10}$ cycloalkyl, aryl and heterocycle, where each is optionally independently substituted with 1 to 4 of $C_{1-6}$ alkyl, $C_{1-6}$ alkoxy, halo, $CH_2OH$, and benzyloxy;

$R^{27}$ is selected from hydrogen, $C_{1-18}$ alkyl, $C_{3-10}$ cycloalkyl, ($C_{3-10}$ cycloalkyl)-$C_{1-6}$ alkyl, aryl, and aryl$C_{1-18}$ alkyl; and salts, tautomers, polymorphs, and stereoisomers thereof.

2. The compound of claim 1 wherein $R^1$ is haloaryl, X is methylene, $R^3$ is heterocycle substituted with 1 or 2 $R^{17}$.

3. The compound of claim 1 wherein $R^1$ is an aryl or aromatic heterocycle substituted with 1 or 2 $R^6$.

4. The compound of claim 1 wherein $R^3$ is heterocycle.

5. The compound of claim 1 wherein $YR^1$ is haloaryl.

6. The compound of claim 5 wherein haloaryl is ortho-fluorophenyl.

7. The compound of claim 1 wherein $R^3$ is isoxazolyl substituted with 1 $R^{17}$.

8. The compound of claim 2 wherein $R^{17}$ is aryl or an aromatic heterocycle, wherein each of said aryl and aromatic heterocycle is substituted with 1, 2 or 3 $R^{19}$.

9. The compound of claim 1 wherein $YR^1$ is none of hydrogen, $C_{3-10}$ cycloalkyl, or $C_{1-6}$ alkyl.

10. The compound of claim 1 wherein $YR^1$ is not hydrogen or $C_{1-6}$ alkyl.

11. The compound of claim 1 wherein $R^{19}$ is trihalomethyl, trihalomethoxy, alkoxy or halogen.

12. The compound of claim 1 wherein $R^1$ is aryl or aromatic heterocyle substituted with 1, 2 or 3 $R^6$ wherein $R^6$ is halogen, $C_{1-18}$ alkoxy; or $C_{1-18}$ haloalkyl.

13. The compound of claim 12 wherein $R^1$ is phenyl substituted with 1, 2 or 3 halogens.

14. The compound of claim 13 wherein halogen is fluoro.

15. The compound of claim 1 wherein Y is a single bond, O, $C_{1-6}$ alkylene, $C_{2-6}$ alkenylene, $C_{2-6}$ alkynylene or one of said groups containing 1 to 3 heteroatoms selected from O, S or $NR^{11}$.

16. The compound of claim 15 wherein Y is —O(CH$_2$)$_{1-5}$—, —(CH$_2$)$_{1-4}$—O—(CH$_2$)$_{1-4}$—, —S—(CH$_2$)$_{1-5}$—, —(CH$_2$)$_{1-4}$—S—(CH$_2$)$_{1-4}$—, —NR$^{11}$—(CH$_2$)$_{1-5}$—, —(CH$_2$)$_{1-4}$—NR$^{11}$—(CH$_2$)$_{1-4}$ or $C_{3-10}$ cycloalkylidene.

17. The compound of claim 15 wherein Y is —OCH$_2$—, —CH$_2$O—, $C_{1-2}$ alkylene, $C_{2-3}$ alkenylene, $C_{2-3}$ alkynylene, O or a bond.

18. The compound of claim 15 wherein Y is a bond.

19. The compound of claim 1 wherein $YR^1$ is a single ring aromatic carbocycle or a heterocycle containing 1 or 2 N, S or O atoms in the ring.

20. The compound of claim 19 wherein the carbocycle or heterocycle contains 4 to 6 ring atoms.

21. The compound of claim 1 wherein $YR^1$ is halo- or halomethyl-substituted phenyl.

22. The compound of claim 1 wherein aryl or heteroaryl are substituted ortho or meta with halo- or halomethyl.

23. The compound of claim 1 wherein X is alkylene.

24. The compound of claim 1 wherein X is selected from the group consisting of —CH$_2$—, —CH(CH$_3$)—, —CH$_2$—CH$_2$—, —CH$_2$—CH$_2$—CH$_2$—, —CH$_2$—CH$_2$—CH$_2$—CH$_2$, $C_{3-10}$ cycloalkylidene, $C_{2-6}$ alkenylene and $C_{2-6}$ alkynylene.

25. The compound of claim 1 wherein X is methylene.

26. The compound of claim 1 wherein $R^3$ is aryl or a heterocycle substituted with 0 to 3 $R^{17}$.

27. The compound of claim 26 wherein the heterocycle is an aromatic heterocycle.

28. The compound of claim 27 wherein the heterocycle contains 1, 2 or 3 N, S or O atoms in the ring, is linked to X through a ring carbon atom and contains 4 to 6 total ring atoms.

29. The compound of claim 28 wherein $R^3$ is isoxazolyl substituted with 1 to 3 $R^{17}$.

30. The compound of claim 1 wherein $R^{17}$ is aryl or a heterocycle further substituted with 1 to 3 $R^{19}$.

31. The compound of claim 1 wherein M is aryl or aromatic heterocycle.

32. The compound of claim 1 wherein Q contains 0 to 20 atoms selected from C, O, S, N and H.

33. The compound of claim 1 wherein M is selected from the group consisting of $C_{3-10}$ cycloalkyl, $C_{3-10}$ cycloalkenyl, $C_{7-10}$ cycloalkynyl, aryl and heterocycle.

34. The compound of claim 1 wherein $R^{17}$ is selected from the group consisting of $C_{3-10}$ cycloalkyl, $C_{3-10}$ cycloalkenyl, $C_{7-10}$ cycloalkynyl, halogen, aryl, aryloxy, arylthio, arylsulfoxide, arylsulfone, arylsulfonamide, arylalkyl; arylalkyloxy; arylalkylthio; heterocycle; $C_{1-18}$ hydroxyalkyl, each of said $C_{3-10}$ cycloalkyl, $C_{3-10}$ cycloalkenyl, $C_{7-10}$ cycloalkynyl, halogen, aryl, aryloxy, arylthio, arylsulfoxide, arylsulfone, arylsulfonamide, arylalkyl; arylalkyloxy; arylalkylthio; heterocycle; and $C_{1-18}$ hydroxyalkyl is unsubstituted or is substituted 1 or more $R^{19}$.

35. The compound of claim 1 wherein $R^{17}$ is selected from the group consisting of aryl and heterocycle, and where said aryl or heterocycle is optionally substituted with 1 or more $R^{19}$.

36. The compound of claim 1 wherein $R^9$ and $R^{18}$ are H, OH or alkyl.

37. The compound of claim 1 wherein $R^5$ is H.

38. The compound of claim 1 wherein $R^6$ is halogen.

39. The compound of claim 1 wherein $R^7$, $R^8$, $R^{10}$, $R^{11}$, $R^{15}$, $R^{16}$, $R^{20}$, and $R^{21}$ are independently H or $C_{1-18}$ alkyl.

40. The compound of claim 1 wherein $R^{12}$ is OH or alkyl.

41. The compound of claim 1 wherein $R^{19}$ is selected from the group consisting of H; $C_{1-18}$ alkyl; $C_{2-18}$ alkenyl; $C_{2-18}$ alkynyl; $C_{1-18}$ alkoxy; alkenyloxy; alkynyloxy; $C_{1-18}$ alkylthio; $C_{3-10}$ cycloalkyl; $C_{4-10}$ cycloalkenyl; $C_{4-10}$ cycloalkynyl; halogen; OH; CN; cyanoalkyl; NO$_2$; NR$^{20}$R$^{21}$; haloalkyl; haloalkyloxy; C(=O)R$^{18}$; C(=O)OR$^{18}$; OalkenylC(=O)OR$^{18}$; —OalkylC(=O)NR$^{20}$R$^{21}$; aryl; heterocycle; —OalkylOC(=O)R$^{18}$; C(=O)N(C$_{1-6}$alkyl), N(H)S(O)(O)(C$_{1-6}$ alkyl); arylalkyloxy; aryloxy; arylalkyloxy; and arylalkyl.

42. The compound of claim 41 wherein $R^{19}$ is independently selected from the group consisting of halogen, N(R$^{20}$R$^{21}$), alkoxy, halo-substituted alkyl and halo-substituted alkoxy.

43. The compound of claim 1 wherein $R^{25}$ and $R^{26}$ are not present.

44. The compound of claim 1 which is not substituted at $R^{25}$ but is substituted at $R^{26}$, and either $R^2$ or $R^4$ is selected from (=O), (=S), and (=NR$^{27}$).

45. The compound of claim 1 wherein haloalkyl or haloalkyloxy is —CF$_3$ or —OCF$_3$.

46. A compound having the general formula (A), wherein:
the dotted lines represent optional double bonds, provided that no two double bonds are adjacent to one another, and that the dotted lines represent at least 3, optionally 4 double bonds;
$R^1$ is selected from hydrogen, aryl, heterocycle (other than piperazinyl, piperidinyl, or either substituted with 1 or more $R^6$), $C_1$-$C_{10}$ alkoxy, $C_1$-$C_{10}$ alkyl-amino, $C_1$-$C_{10}$ dialkyl-amino, $C_{3-10}$ cycloalkyl, $C_{4-10}$ cycloalkenyl, and $C_{4-10}$ cycloalkynyl, wherein each are optionally substituted with 1 or more $R^6$;

Y is selected from a single bond, $S(O)_m$ (where m is an integer from 0 to 2), $NR^{11}$, $C_{1-10}$ alkylene, $C_{2-10}$ alkenylene, $C_{2-10}$ alkynylene, or $C_{1-10}$ alkylene, $C_{2-20}$ alkenylene or $C_{2-10}$ alkynylene wherein 1 to 3 methylene groups optionally are independently replaced by 1 to 3 heteroatoms selected from O, S or $NR^{11}$; provided, however, that $YR^1$ is not H;

$R^2$ and $R^4$ are independently selected from hydrogen, $C_{1-18}$ alkyl, $C_{2-18}$ alkenyl, $C_{2-18}$ alkynyl, $C_{1-18}$ alkoxy, $C_{1-18}$ alkylthio, halogen, —OH, —CN, —$NO_2$, —$NR^7R^8$, haloalkyloxy, haloalkyl, —C(=O)$R^9$, —C(=S)$R^9$, SH, aryl, aryloxy, arylthio, arylalkyl, $C_{1-18}$ hydroxyalkyl, $C_{3-10}$ cycloalkyl, $C_{3-10}$ cycloalkyloxy, $C_{3-10}$ cycloalkylthio, $C_{3-10}$ cycloalkenyl, $C_{7-10}$ cycloalkynyl, or heterocycle, provided that when one of $R^{25}$ or $R^{26}$ is present, then either $R^4$ is selected from (=O), (=S), and =$NR^{27}$ or $R^2$ is selected from =S or =$NR^{27}$; and further provided that not both of $R^2$ and $R^4$ is OH, SH, thio or oxo;

X is selected from $C_1$-$C_{10}$ alkylene, $C_{2-10}$ alkenylene or $C_{2-10}$ alkynylene;

$R^3$ is selected from aryl, aryloxy, arylthio, cycloalkyl, cycloalkenyl, cycloalkynyl, aryl-N($R^{10}$)—, or heterocycle, where each said substituent may be optionally substituted with at least one $R^{17}$, provided that for cycloalkenyl the double bond is not adjacent to a nitrogen;

$R^5$ independently is absent or is selected from hydrogen, $C_{1-18}$ alkyl, $C_{2-18}$ alkenyl, $C_{2-18}$ alkynyl, $C_{1-18}$ alkoxy, $C_{1-18}$ alkylthio, halogen, —OH, —CN, —$NO_2$, —$NR^7R^8$, haloalkyloxy, haloalkyl, —C(=O)$R^9$, —C(=O)$OR^9$, —C(=S)$R^9$, SH, aryl, aryloxy, arylthio, arylalkyl, $C_{1-18}$ hydroxyalkyl, $C_{3-10}$ cycloalkyl, $C_{3-10}$ cycloalkyloxy, $C_{3-10}$ cycloalkylthio, $C_{3-10}$ cycloalkenyl, $C_{7-10}$ cycloalkynyl, or heterocycle;

$R^6$ is selected from hydrogen, $C_{1-18}$ alkyl, $C_{2-18}$ alkenyl, $C_{2-18}$ alkynyl, $C_{1-18}$ alkoxy, $C_{1-18}$ alkylthio, $C_{1-18}$ alkylsulfoxide, $C_{1-18}$ alkylsulfone, $C_{1-18}$ halo-alkyl, $C_{2-18}$ halo-alkenyl, $C_{2-18}$ halo-alkynyl, $C_{1-18}$ halo-alkoxy, $C_{1-18}$ halo-alkylthio, $C_{3-10}$ cycloalkyl, $C_{3-10}$ cycloalkenyl, $C_{7-10}$ cycloalkynyl, halogen, OH, CN, cyanoalkyl, —$CO_2R^{18}$, $NO_2$, —$NR^7R^8$, $C_{1-18}$ haloalkyl, C(=O)$R^{18}$, C(=S)$R^{18}$, SH, aryl, aryloxy, arylthio, arylsulfoxide, arylsulfone, arylsulfonamide, aryl($C_{1-18}$)alkyl, aryl($C_{1-18}$)alkyloxy, aryl($C_{1-18}$)alkylthio, heterocycle, $C_{1-18}$ hydroxyalkyl, where each may be optionally substituted with at least 1 $R^{19}$;

$R^7$ and $R^8$ are independently selected from hydrogen, $C_{1-18}$ alkyl, $C_{1-18}$ alkenyl, aryl, $C_{3-10}$ cycloalkyl, $O_{4-10}$ cycloalkenyl, heterocycle, —C(=O)$R^{12}$; —C(=S)$R^{12}$, an amino acid residue linked through a carboxyl group thereof, or where $R^7$ and $R^8$ together with the nitrogen form a heterocycle;

$R^9$ and $R^{18}$ are independently selected from hydrogen, OH, $C_{1-18}$ alkyl, $C_{2-18}$ alkenyl, $C_{3-10}$ cycloalkyl, $C_{4-10}$ cycloalkenyl, $C_{1-18}$ alkoxy, —$NR^{15}R^{16}$aryl, an amino acid residue linked through an amino group of the amino acid, $CH_2OCH(=O)R^{9a}$, or $CH_2OC(=O)OR^{9a}$ where $R^{9a}$ is $C_1$-$C_{12}$ alkyl, $C_6$-$C_{20}$ aryl, $C_7$-$C_{20}$ alkylaryl or $C_7$-$C_{20}$ aralkyl;

$R^{10}$ and $R^{11}$ are independently selected from the group consisting of hydrogen, $C_{1-18}$ alkyl, $C_{2-18}$ alkenyl, $C_{3-10}$ cycloalkyl, $C_{4-10}$ cycloalkenyl, aryl, —C(=O)$R^{12}$, heterocycle, or an amino acid residue linked through an amino group or carboxyl group of the amino acid;

$R^{12}$ is selected from the group consisting of hydrogen, $C_{1-18}$ alkyl, $C_{2-18}$ alkenyl, aryl, $C_{3-10}$ cycloalkyl, $C_{4-10}$ cycloalkenyl, or an amino acid residue linked through an amino group or carboxyl group of the amino acid;

$R^{15}$ and $R^{16}$ are independently selected from hydrogen, $C_{1-18}$ alkyl, $C_{2-18}$ alkenyl, $C_{2-18}$ alkynyl, aryl, $C_{3-10}$ cycloalkyl, $C_{4-10}$ cycloalkenyl, or an amino acid residue linked through an amino group or carboxyl group of the amino acid;

$R^{17}$ is independently M-Q- wherein M is a ring optionally substituted with 1 or more $R^{19}$, and Q is a bond or a linking group connecting M to $R^3$ having 1 to 10 atoms selected from C and optionally 1 or more O, N or S atoms and optionally substituted with 1 or more $R^{19}$;

$R^{19}$ is selected from (a) H;

(b) $NO_2$, SH, $NR^{20}R^{21}$, OH, halogen and CN;

(c) $C_{1-18}$ alkyl, $C_{2-18}$ alkenyl and $C_{2-18}$ alkynyl;

(d) $C_{1-18}$ alkyl, $C_{2-18}$ alkenyl and $C_{2-18}$ alkynyl wherein 1 or more methylene are replaced by 1 or more O, S, $NR^{20}$, or N($R^{20}$)C(O);

(e) Substituents c), or d) substituted further by $C_{3-10}$ cycloalkyl, $C_{4-10}$ cycloalkenyl, $C_{4-10}$ cycloalkynyl, aryl or heterocycle;

(f) $C_{3-10}$ cycloalkyl, $C_{4-10}$ cycloalkenyl, $C_{4-10}$ cycloalkynyl, aryl and heterocycle, or said groups substituted with $C_{1-6}$ alkyl, C(O)O$R^{12}$=O, halogen, CN, C(O)N$R^{20}R^{21}$, C(O)$R^{18}$ or OC(O)$R^{18}$;

(g) C(O)$R^{18}$, C(O)O$R^{18}$, OC(O)$R^{18}$, C(S)$R^{18}$ and C(O)N($R^{12}$)$_2$;

(h) Substituents c) or d) substituted with =O, CN, halogen, C(O)$R^{18}$, C(O)N$R^{20}R^{21}$, OC(O)$R^{18}$, heterocycle and heterocycle substituted with $C_1$-$C_6$ alkyl, C(O)O$R^{12}$, =O, CN, halogen, OC(O)$R^{18}$ or C(O)N$R^{20}R^{21}$; and (i) Substituents e) or f) substituted further with $C_{1-18}$ alkyl, =O, $NR^{20}R^{21}$, CN, $C_{1-18}$ alkoxy, heterocycle, $C_{1-18}$ haloalkyl, heterocyclealkyl or halogen;

$R^{20}$ and $R^{21}$ are independently selected from hydrogen, $C_{1-18}$ alkyl, $C_{2-18}$ alkenyl, $C_{2-18}$ alkynyl, aryl, heterocycle, $C_{3-10}$ cycloalkyl, $C_{4-10}$ cycloalkenyl, —C(=O)$R^{12}$, or —C(=S)$R^{12}$;

$R^{25}$ and $R^{26}$ are independently not present or are selected from hydrogen, $C_{1-18}$ alkyl, $C_{3-10}$ cycloalkyl, aryl and heterocycle, where each is optionally independently substituted with 1 to 4 of $C_{1-6}$ alkyl, $C_{1-6}$ alkoxy, halo, $CH_2OH$, and benzyloxy; and $R^{27}$ is selected from hydrogen, $C_{1-18}$ alkyl, $C_{3-10}$ cycloalkyl, ($C_{3-10}$ cycloalkyl)-$C_{1-6}$ alkyl, aryl, and aryl $C_{1-18}$ alkyl, and salts, tautomers, polymorphs, and stereoisomers thereof.

47. The compound of claim 46 wherein Y is a single bond, and $R^1$ is aryl or aromatic heterocycle which is unsubstituted or substituted with one or more $R^6$.

48. The compound of claim 46 wherein X is $C_1$-$C_{10}$ alkylene, $C_{2-10}$ alkenylene or $C_{2-10}$ alkynylene.

49. The compound of claim 46 wherein $R^3$ is heterocyle.

50. The compound of claim 46 wherein $R^3$ is heterocycle substituted with $R^{17}$ where Q is a bond and M is aryl substituted with 1 or 2 $R^{19}$.

51. The compound of claim 46 wherein Y is a single bond, and $R^1$ is phenyl.

52. The compound of claim 46 wherein $R^3$ is isoxazole substituted with $R^{17}$ where Q is a bond and M is aryl substituted with 1 or 2 $R^{19}$.

53. The compound of claim 46 wherein $R^3$ is isoxazole substituted with $R^{17}$ where Q is a bond and M is phenyl substituted with 1 or 2 $R^{19}$.

54. A compound having the structure

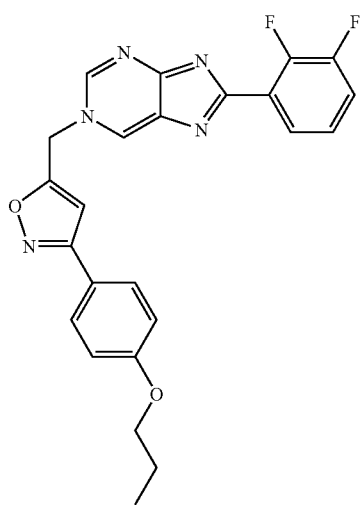

and its salts, tautomers, and polymorphs.

55. 8-(2-Fluorophenyl)-1-[(4-trifluoromethyl)phenylmethyl]-1H-purine and its salts, tautomers, and polymorphs.

56. 1-((3-(4-chlorophenyl)isoxazol-5-yl)methyl)-8-(2,3-difluorophenyl)-1H-purine and its salts, tautomers, and polymorphs.

57. The compound

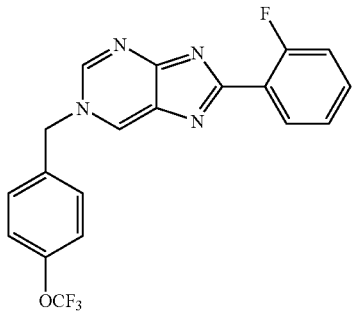

and its salts, tautomers, and polymorphs.

58. A compound of the structure

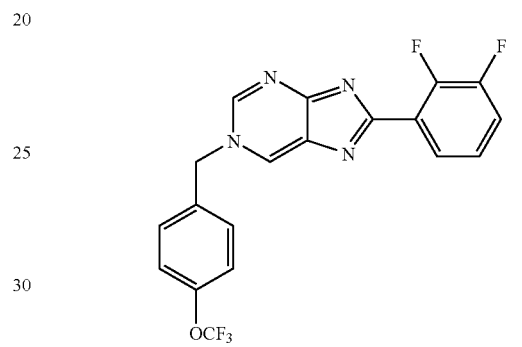

and its salts, tautomers, and polymorphs.

59. 1-((3-(4-chlorophenyl)isoxazol-5-yl)methyl)-8-(2,3-difluorophenyl)-1H-purine and its salts, tautomers, and polymorphs.

60. A composition comprising a pharmaceutically acceptable excipient and a compound of claim 1, 46, and or 54-59.

61. A method comprising administering to a subject in need of treatment of an HCV infection an amount of a composition of claim 60 that is effective to treat the HCV infection.

62. The method of claim 61 further comprising administering at least one additional antiviral therapy to the subject.

63. The method of claim 62 wherein the additional therapy is selected from the group consisting of an interferon alpha and ribavirin.

* * * * *